(12) United States Patent
Feldberg et al.

(10) Patent No.: US 11,746,089 B2
(45) Date of Patent: Sep. 5, 2023

(54) COMPOUNDS AND METHODS FOR TREATING ALCOHOL DISORDER

(71) Applicant: SOPHROSYNE PHARMACEUTICALS LIMITED, George Town (KY)

(72) Inventors: Lewis Feldberg, Montclair, NJ (US); Akram Sabouni, Cary, NC (US); Vincent Wing-Fai Tai, Cary, NC (US)

(73) Assignee: SOPHROSYNE PHARMACEUTICALS LIMITED, George Town (KY)

( * ) Notice: Subject to any disclaimer, the term of this patent is extended or adjusted under 35 U.S.C. 154(b) by 0 days.

(21) Appl. No.: 18/152,375

(22) Filed: Jan. 10, 2023

(65) Prior Publication Data

US 2023/0159461 A1    May 25, 2023

Related U.S. Application Data

(63) Continuation of application No. 17/538,250, filed on Nov. 30, 2021.

(60) Provisional application No. 63/202,424, filed on Jun. 10, 2021, provisional application No. 63/119,211, filed on Nov. 30, 2020.

(51) Int. Cl.
| | | |
|---|---|---|
| *C07D 211/46* | (2006.01) | |
| *C07C 333/04* | (2006.01) | |
| *C07C 333/20* | (2006.01) | |
| *A61P 25/32* | (2006.01) | |

(52) U.S. Cl.
CPC ............ *C07D 211/46* (2013.01); *A61P 25/32* (2018.01); *C07C 333/04* (2013.01); *C07C 333/20* (2013.01)

(58) Field of Classification Search
CPC ... C07D 211/46; C07C 333/04; C07C 333/20; A61P 25/32
See application file for complete search history.

(56) References Cited

U.S. PATENT DOCUMENTS

| | | | |
|---|---|---|---|
| 3,896,169 A | 7/1975 | Tiles et al. | |
| 3,897,492 A | 7/1975 | Tiles et al. | |
| 4,383,025 A | 5/1983 | Green et al. | |
| 5,153,219 A | * 10/1992 | Faiman | A61P 25/32 424/10.1 |
| 7,250,401 B2 | 7/2007 | Schloss | |
| 2022/0169610 A1 | 6/2022 | Feldberg et al. | |

FOREIGN PATENT DOCUMENTS

| | | |
|---|---|---|
| EP | 0062876 A1 | 10/1982 |
| WO | 2022115742 A1 | 6/2022 |

OTHER PUBLICATIONS

Yan et al., "Improving the Solubility of Agomelatine via Cocrystals", Crystal Growth & Decision, 2012, pp. 2226-2233.
International Search Report and Written Opinion Issued in PCT/US2021/061098 dated Apr. 13, 2022.
Notice of Allowance for U.S. Appl. No. 17/860,913 dated Sep. 15, 2022.
PUBCHEM 319089572 deposited Nov. 29, 2016, pp. 1-5.
PUBCHEM 431811781 deposited on Aug. 14, 2020, pp. 1-6.
Fukte et al., "Coformer Selection: An Important Tool in Cocrystal Formation", International Journal of Pharmacy and Pharmaceutical Sciences, 2014, vol. 6, Issue 7, pp. 9-14.
Mays et al., "Inhibition of Recombinant Human Mitochondrial Aldehyde Dehydrogenase by Two Intermediate Metabolites of Disulfiram", Biochemical Pharmacology, 1998, vol. 55, pp. 1099-1103.
International Search Report and Written Opinion Issued in PCT/US2022/33012 dated Nov. 13, 2022.
Non-Final Office Action dated Jan. 20, 2023 in U.S. Appl. No. 17/538,250.

\* cited by examiner

*Primary Examiner* — Timothy R Rozof
(74) *Attorney, Agent, or Firm* — GOODWIN PROCTER, LLP

(57) ABSTRACT

The disclosure is directed to, in part, compounds, or pharmaceutically acceptable salts or solvates thereof, for modulating the activity of aldehyde dehydrogenase such as ALDH2 and/or methods for treating and/or preventing an alcohol related disorder such as alcohol use disorder, alcohol induced disorder, alcohol abuse, alcohol dependence, alcohol intoxication, alcohol withdrawal, and the like and/or methods for reducing the amount of alcohol consumed, reducing alcoholic cravings, or increasing the percentage of no heavy drinking days for a subject with alcohol use disorder.

10 Claims, 15 Drawing Sheets

ALDH$_2$ Inhibition, 10 Day Rat Pharmacology Study

Peak 1: Example 1-2A
Peak 2: Example 1-2B

COMPOUNDS AND METHODS FOR TREATING ALCOHOL DISORDER

CROSS REFERENCE TO RELATED APPLICATIONS

This application is a continuation of U.S. application Ser. No. 17/538,250, filed Nov. 30, 2021, which claims priority to U.S. Provisional Application No. 63/119,211, filed Nov. 30, 2020 and U.S. Provisional Application No. 63/202,424, filed Jun. 10, 2021, each of which are hereby incorporated by reference in their entirety.

FIELD

Embodiments disclosed herein are directed, in part, to compounds, or pharmaceutically acceptable salts or solvates thereof, for modulating the activity of aldehyde dehydrogenase such as ALDH2 and/or methods for treating and/or preventing an alcohol related disorder such as, but not limited to, alcohol use disorder, alcohol induced disorder, alcohol abuse, alcohol dependence, alcohol intoxication, alcohol withdrawal, and the like and/or methods for reducing the amount of alcohol consumed, reducing alcoholic cravings, or increasing the percentage of no heavy drinking days for a subject with alcohol use disorder.

BACKGROUND

Aldehyde dehydrogenase (ALDH) is a polymorphic enzyme converting aldehydes to carboxylic acids through oxidation. ALDH1 and ALDH2 are the most important enzymes for aldehyde oxidation, and both are tetrameric enzymes composed of 54 kDa subunits. Aldehyde dehydrogenase, mitochondrial (ALDH2) is an enzyme that in humans is encoded by the ALDH2 gene located on chromosome 12. ALDH2 plays a crucial role in maintaining low blood levels of acetaldehyde during alcohol oxidation.

Aldehyde dehydrogenase, mitochondrial (ALDH2) has long been of interest as a target for potential treatments for alcohol abuse. Recent evidence suggests that modulating the activity of ALDH2 such as ALDH2 inhibition, may be beneficial in the treatment of a variety of an alcohol related disorder, such alcohol use disorder, alcohol induced disorder, alcohol abuse, alcohol dependence, alcohol intoxication, alcohol withdrawal, and the like. Thus, there is a need to identify an ALDH2 modulator for the treatment of these and other conditions. The present embodiments described herein fulfill these needs and others.

SUMMARY

Figure 1:
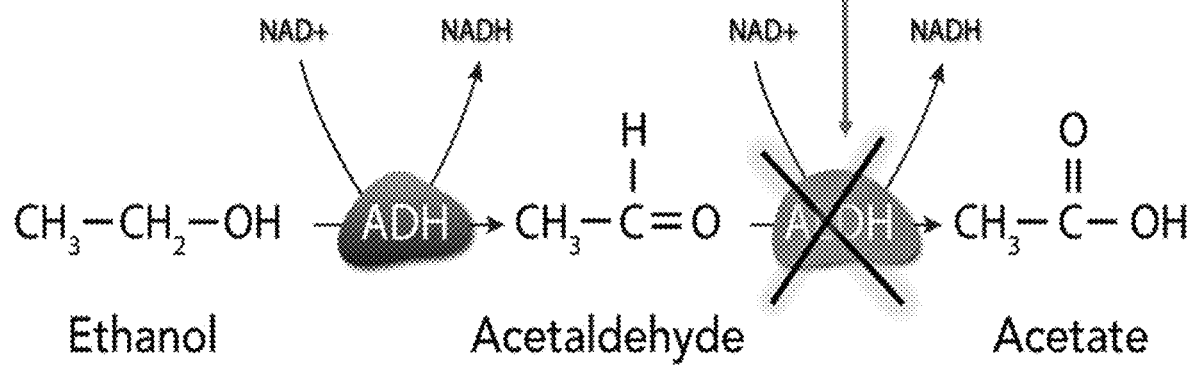
FIG. 1 illustrates the ethanol metabolism and the role of Example 1-2 or analogs thereof in inhibiting/preventing ALDH2 from metabolizing acetaldehyde into acetic acid.

The disclosure is directed to compounds, or pharmaceutically acceptable salts or solvates thereof, or pharmaceutical compositions thereof, which, in part, modulate the activity of the ALDH2. The compounds can have, for example, a formula as described herein. In some embodiments, the compound is selected from a compound described herein. In some embodiments, methods of treating and/or preventing the conditions described herein are provided. In some embodiments, the condition is an alcohol related disorder such as, but not limited to, alcohol use disorder, alcohol induced disorder, alcohol abuse, alcohol dependence, alcohol intoxication, alcohol withdrawal, and the like.

In some embodiments, the compound has a formula of Formula (I), Formula (I-a), Formula (I-b), or Formula (III):

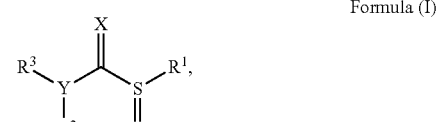

Formula (I)

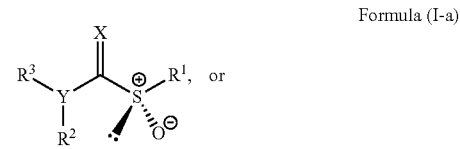

Formula (I-a)

Formula (I-b)

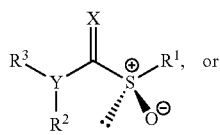

or

Formula (III)

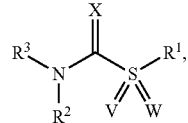

or a pharmaceutically acceptable salt or solvate thereof, wherein X, Y, R$^1$, R$^2$, and R$^3$ are as provided for herein and, for example, can be selected from the respective groups of chemical moieties described herein. Also provided are processes for preparing these compounds.

In some embodiments, the compound has a formula of Formula (XIII), Formula (XIII-a), or Formula (XIII-b):

Formula (XIII)

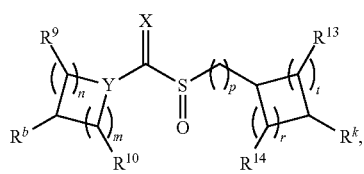

Formula (XIII-a)

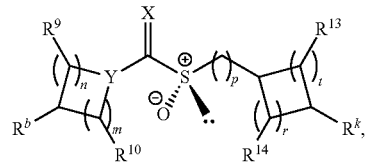

Formula (XIII-b)

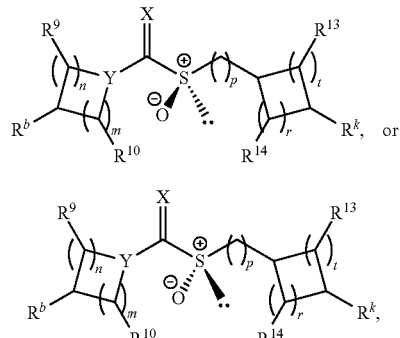

a pharmaceutically acceptable salt or solvate thereof, wherein X, Y, m, n, R$^9$, R$^{10}$, R$^{13}$, R$^{14}$, R$^k$, and R$^b$ are as provided for herein and, for example, can be selected from the respective groups of chemical moieties described herein. Also provided are processes for preparing these compounds.

In some embodiments, the compound has a formula of Formula (IV), Formula (V), Formula (VI), or Formula (VII):

Formula (IV)

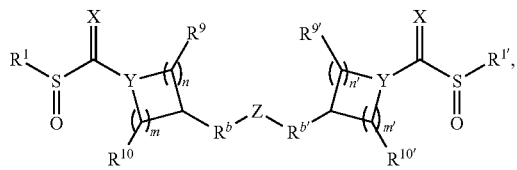

Formula (V)

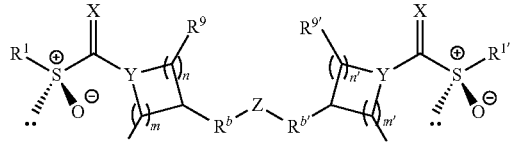

Formula (VI)

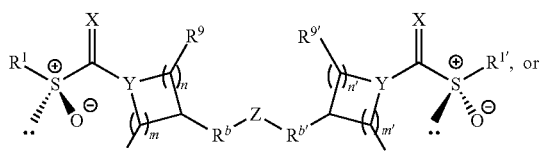

Formula (VII)

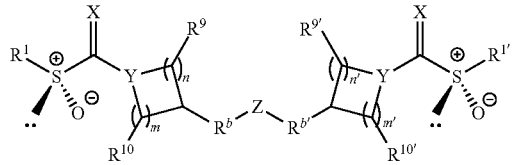

or a pharmaceutically acceptable salt or solvate thereof, wherein X, Y, Z, n, m, n', m', R$^1$, R$^b$, R$^{b'}$, R$^9$, R$^{10}$, R$^{9'}$, R$^{10'}$, and R$^{1'}$ are as provided for herein and, for example, can be selected from the respective groups of chemical moieties described herein. Also provided are processes for preparing these compounds.

In some embodiments, the compound has a formula of Formula (VIII), Formula (IX), Formula (X), or Formula (XI):

Formula (VIII)

Formula (IX)

Formula (X)

Formula (XI)

or a pharmaceutically acceptable salt or solvate thereof, wherein X, U, j, j', R$^2$, R$^3$, R$^{2'}$, R$^{3'}$, R$^{15}$, and R$^{15'}$ are as provided for herein and, for example, can be selected from the respective groups of chemical moieties described herein. Also provided are processes for preparing these compounds.

In some embodiments, also provided are pharmaceutical compositions comprising one or more compounds as described herein, which can also comprise a pharmaceutically acceptable carrier. In some embodiments, the compounds described herein can be provided in any form, such as, but not limited to, a solid or solution (e.g., aqueous solution), as described herein. The compounds described herein, for example, can be obtained and employed in lyophilized form alone or with suitable additives.

Also provided are methods for treating and/or preventing alcohol related disorder in a subject or a subject in need thereof. In some embodiments, the alcohol related disorder is associated with aberrant ALDH2 activity as described herein. In some embodiments, the methods comprise administering one or more compounds or a pharmaceutical composition as described herein to a subject or a subject in need thereof.

In some embodiments, methods of reducing the amount of alcohol consumed in a subject with alcohol use disorder are provided. In some embodiments, the methods comprise administering one or more compounds or a pharmaceutical composition as described herein to a subject or a subject in need thereof.

In some embodiments, methods of reducing alcoholic cravings in a subject with alcohol use disorder are provided. In some embodiments, the methods comprise administering one or more compounds or a pharmaceutical composition as described herein to a subject or a subject in need thereof.

In some embodiments, methods of increasing the percentage of no heavy drinking days for a subject with alcohol use disorder are provided. In some embodiments, the methods comprise administering one or more compounds or a pharmaceutical composition as described herein to a subject or a subject in need thereof.

Stereoisomers of the compounds of the various formula provided herein, and pharmaceutical salts and solvates thereof, are also contemplated, described, and encompassed herein. Methods of using compounds of the formula provided herein are described, as well as pharmaceutical compositions including the compounds of the formula provided herein.

DETAILED DESCRIPTION

The disclosure may be more fully appreciated by reference to the following description, including the following definitions and examples. Certain features of the disclosed compositions and methods that are described herein in the context of separate aspects may also be provided in combination in a single aspect. Alternatively, various features of the disclosed compositions and methods that are, for brevity, described in the context of a single aspect, may also be provided separately or in any subcombination.

At various places in the present specification, substituents of compounds are disclosed in groups or in ranges. It is specifically intended that the embodiments include each and every individual subcombination of the members of such groups and ranges. For example, the term "$C_{1-6}$ alkyl" or "$C_1$-$C_6$ alkyl" is specifically intended to individually disclose methyl, ethyl, $C_3$ alkyl, $C_4$ alkyl, $C_5$ alkyl, and $C_6$ alkyl.

It is further appreciated that certain embodiments, which are, for clarity, described in the context of separate embodiments, can also be provided in combination in a single embodiment. Conversely, various features of the embodiments, which are, for brevity, described in the context of a single embodiment, can also be provided separately or in any suitable sub-combination.

All percentages and ratios used herein, unless otherwise indicated, are by weight.

The term "alkyl," when used alone or as part of a substituent group, refers to a straight- or branched-chain hydrocarbon group, a spirocyclic group, or a fused or bridged bicyclic group, each of which has from 1 to 12 carbon atoms ("$C_1$-$C_{12}$"), or 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like. The term "spirocyclic group" refers to spirocyclic compounds in which the two rings share only one single atom, the spiro atom, which is usually a quaternary carbon. Examples of spirocyclic compounds are spiro[2,3]undecane, spiro[3,3]heptane, and spiro[5,5]undecane. The term "fused bicyclic group" refers to fused bicyclic compounds, in which two rings share two adjacent atoms. Examples of fused bicyclic compounds include bicyclo[4.4.0]decane, α-thujene and decalin, and the like. The term "bridged bicyclic group" refers to bridged bicyclic compounds, in which the two rings share three or more atoms, separating the two bridgehead atoms by a bridge containing at least one atom. Examples of bridged bicyclic compounds include bicyclo[2.2.1]heptane, bicyclo[1,1,1]pentane, bicyclo[2.2.1]heptane, bicyclo[2.2.2]octane, bicyclo[3.3.1]nonane, bicyclo[3.3.3]undecane, and the like. The term "haloalkyl," when used alone or as part of a substituent group, refers to a straight- or branched-chain hydrocarbon group having from 1 to 12 carbon atoms ("$C_1$-$C_{12}$"), or 1 to 6 carbons atoms ("$C_1$-$C_6$"), in the group, wherein one or more of the hydrogen atoms in the group have been replaced by a halogen atom. Examples of haloalkyl groups include trifluoromethyl (—$CF_3$, $C_1$haloalkyl), trifluoroethyl (—$CH_2CF_3$, $C_2$haloalkyl), and the like.

The term "halo" or "halogen" refers to chloro, fluoro, bromo, or iodo.

The term "oxo" refers to an oxygen atom (i.e., =O) as a divalent substituent, forming a carbonyl group when attached to a carbon (e.g. C=O), or attached to a nitrogen or sulfur heteroatom forming a nitroso, sulfinyl or sulfonyl.

The term "cycloalkyl" when used alone or as part of a substituent group refers to monocyclic, bicyclic, or tricyclic, non-aromatic hydrocarbon groups having from 3 to 10 carbon atoms ("$C_3$-$C_{10}$"), or from 3 to 6 carbon atoms ("$C_3$-$C_6$"), or from 3 to 7 carbon atoms ("$C_3$-$C_7$"). Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "heterocycloalkyl" when used alone or as part of a substituent group refers to any three to fourteen membered monocyclic, bicyclic, or tricyclic saturated ring structure containing at least one heteroatom selected from the group consisting of O, N, and S. Heterocycloalkyl groups may be described with respect to the number of atoms in the group, or with respect to the number of carbon atoms in the group. The term "bicyclic" ring structure refers to a spirocyclic, fused bicyclic, or bridged bicyclic ring. For example, the term "4-10 membered heterocycloalkyl" refers to a heterocycloalkyl group containing between 4 and 10 ring atoms. The term —$C_4$-$C_6$ heterocycloalkyl, for example, refers to a heterocycloalkyl group containing four to six carbon atoms. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, Decahydroquinoline, 2-azaspiro[5.5]undecane, 6-oxa-3-azabicyclo[3.1.1]heptane, and the like.

The term "aryl" when used alone or as part of a substituent group refers to a mono- or bicyclic-aromatic hydrocarbon ring structure having 6 or 10 carbon atoms in the ring system. Examples of aryl groups are phenyl and naphthyl.

The term "heteroaryl" when used alone or as part of a substituent group refers to a mono-, bi- or tricyclic-aromatic ring structure including carbon atoms as well as up to four heteroatoms selected from nitrogen, oxygen, and sulfur. Heteroaryl rings can include a total of 5, 6, 9, 10, or 14 ring atoms. Heteroaryl groups may be described with respect to the number of atoms in the group, or with respect to the number of carbon atoms in the group. Thus, the term "5-14 membered heteroaryl" refers to a heteroaryl group containing between 5 and 14 ring atoms. The term $—C_4-C_6$ heteroaryl, for example, refers to a heteroaryl group containing four to six carbon atoms. Examples of heteroaryl groups include but are not limited to, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like.

When a range of carbon atoms is used herein, for example, $C_1-C_6$ all ranges, as well as individual numbers of carbon atoms are encompassed. For example, "$C_1-C_3$" includes $C_1-C_3$, $C_1-C_2$, $C_2-C_3$, $C_1$, $C_2$, and $C_3$. The range of carbon atoms may be expressed with alternative expressions. For example, the term "$C_{1-6}$" is an alternative expression of "$C_1-C_6$".

When a ring system is described herein as having a range of members, for example, "5-14-membered", all ranges, as well as individual numbers of atoms are encompassed. For example, "5-14-membered" includes 5-6-membered, 5-10-membered, 6-9-membered, 5-membered, 6-membered, 7-membered, 8-membered, and the like.

As used herein, "alkoxy" refers to an —O-alkyl group. Example alkoxy groups include methoxy, ethoxy, propoxy (e.g., n-propoxy and isopropoxy), t-butoxy, and the like.

The term "alkenyl" when used alone or as part of a substituent group refers to a straight- or branched-chain group having from 2 to 12 carbon atoms ("$C_2-C_{12}$"), or 2 to 6 carbons atoms ("$C_{2-6}$"), in the group, wherein the group includes at least one carbon-carbon double bond of alkenyl groups include vinyl (—CH=CH$_2$; $C_2$alkenyl), allyl (—CH$_2$— CH=CH$_2$; $C_3$alkenyl), propenyl (—CH=CHCH$_3$; $C_3$alkenyl); isopropenyl (—C(CH$_3$)=CH$_2$; $C_3$alkenyl), butenyl (—CH=CHCH$_2$CH$_3$; $C_4$alkenyl), sec-butenyl (—C(CH$_3$)=CHCH$_3$; $C_4$alkenyl), iso-butenyl (—CH=C(CH$_3$)$_2$; $C_4$alkenyl), 2-butenyl (—CH$_2$CH=CHCH$_3$; $C_4$alkyl), pentenyl (CH=CHCH$_2$CH$_2$CH$_3$ or CH$_2$=CHCH$_2$CH$_2$—; $C_5$alkenyl), and the like.

The term "alkynyl" when used alone or as part of a substituent group refers to a straight- or branched-chain group having from 2 to 12 carbon atoms ("$C_2-C_{12}$"), or 2 to 6 carbons atoms ("$C_2-C_6$"), in the group, wherein the group includes at least one carbon-carbon triple bond. Examples of alkynyl groups include ethynyl (—C≡CH; $C_2$alkynyl), propargyl (—CH$_2$— CH≡CH; $C_3$alkynyl), and the like.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Geometric isomers of olefins, C=N double bonds, and the like can also be present in the compounds described herein, and all such stable isomers are contemplated in the present embodiments. Geometric isomers of the compounds of the present embodiments are described and may be isolated as a mixture of isomers or as separated isomeric forms.

Compounds provided herein may also include tautomeric forms. All tautomeric forms are encompassed.

In some embodiments, the compounds may exist as rotational isomers. In some embodiments, the compounds exist as mixtures of rotational isomers in any proportion. In other embodiments, the compounds exist as particular rotational isomers, substantially free of other rotational isomers.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, and salts thereof, are substantially isolated. By "substantially isolated" is meant that the compound is at least partially or substantially separated from the environment in which is formed or detected. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as, but not limited to, amines; alkali or organic salts of acidic residues such as, but not limited to, carboxylic acids; and the like. The pharmaceutically acceptable salts include, but are not limited to, the conventional non-toxic salts of the parent compound formed, for example, from non-toxic inorganic or organic acids. The pharmaceutically acceptable salts can be synthesized from the parent compound, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are can be used. Lists of suitable salts are found in *Remington's Pharmaceutical Sciences,* 17$^{th}$ ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound provided herein with one or more solvent molecules.

"Subject" includes humans. The terms "human," "patient," and "subject" are used interchangeably herein.

As used herein, the phrase "in need thereof" means that the animal or mammal (subject) has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. In some embodiments, the subject in need thereof is suspected of having the condition that needs to be treated.

"Treating" or "treatment" of any disease or disorder refers, in some embodiments, to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder. In some embodiments, the disease or disorder is alcohol related disorder.

As used herein, the phrase "integer from X to Y" means any integer that includes the endpoints. For example, the phrase "integer from X to Y" or "1-5" or "1 to 5" means 1, 2, 3, 4, or 5 or any value therein if not modified by the term "integer."

Additionally, unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting essentially of", "consisting of" or "consists." Further, it should be understood that the order of steps or order for performing certain actions are immaterial so long as the process remains operable. Moreover, two or more steps or actions can be conducted simultaneously.

"Compounds of the present disclosure," "compounds as described herein" and equivalent expressions, are meant to embrace compounds of any formula or structural representation as described herein, as well as their subgenera, which expression includes the stereoisomers (e.g., enantiomers, diastereomers) and constitutional isomers (e.g., tautomers) of the various compounds and formula provided for herein as well as pharmaceutically acceptable salts or solvates thereof, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well known in the art.

In some embodiments, compounds having Formula (I), Formula (I-a), Formula (I-b), or Formula (III), or pharmaceutically acceptable salts or solvates thereof.

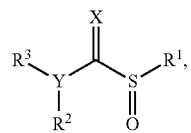

Formula (I)

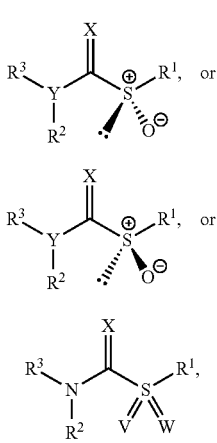

Formula (I-a)

Formula (I-b)

Formula (III)

In some embodiments, the disclosure is directed to compounds of Formula (I).

In some embodiments, the disclosure is directed to pharmaceutically acceptable salts or solvates of compounds of Formula (I).

In other embodiments, the disclosure is directed to compounds of Formula (I-a).

In some embodiments, the disclosure is directed to pharmaceutically acceptable salts or solvates of compounds of Formula (I-a).

In other embodiments, the disclosure is directed to compounds of Formula (I-b).

In some embodiments, the disclosure is directed to pharmaceutically acceptable salts or solvates of compounds of Formula (I-b).

In some embodiments, the disclosure is directed to compounds of Formula (III).

In some embodiments, the disclosure is directed to pharmaceutically acceptable salts or solvates of compounds of Formula (III).

In some embodiments, X in the compounds of Formula (I), Formula (I-a), Formula (I-b), and Formula (III) is O, S, or N—$R^4$. In some embodiments, X is O. In some embodiments, X is S. In some embodiments, X is N—$R^4$.

In some embodiments, Y in the compounds of Formula (I), Formula (I-a), and Formula (I-b) and Formula (III) is N or C—$R^5$. In some embodiments, Y is N. In some embodiments, Y is C—$R^5$.

In some embodiments, V is absent or O. In some embodiments, V is absent. In some embodiments, V is O.

In some embodiments, W is absent or O. In some embodiments, W is absent. In some embodiments, W is O.

In some embodiments, $R^1$, $R^2$, $R^3$, $R^4$, and $R^5$ are each independently H, D, halo, oxo, alkyl, alkoxy, alkenyl, alkynyl, haloalkyl, haloalkoxy, aryl, cycloalkyl, heteroaryl, heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$; In some embodiments, when $R^1$, $R^2$, $R^3$, $R^4$, or $R^5$ is alkyl, alkoxy, alkenyl, alkynyl, haloalkyl, haloalkoxy, aryl, cycloalkyl, heteroaryl, heterocycloalkyl, then $R^1$, $R^2$, $R^3$, $R^4$, or $R^5$ is optionally substituted with at least one $R^b$ substituent; In some embodiments, $R^1$, $R^2$, $R^3$, $R^4$, and $R^5$ are each independently H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^a$-$C(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$;

In some embodiments, when $R^1$, $R^2$, $R^3$, $R^4$, or $R^5$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^1$, $R^2$, $R^3$, $R^4$, or $R^5$ is optionally substituted with 1, 2, 3, 4 or 5 independently selected $R^b$ substituents.

In some embodiments, $R^1$ is $C_{1-6}$alkyl, for example, $C_6$ alkyl, $C_5$ alkyl, $C_4$ alkyl, $C_3$ alkyl, $C_2$ alkyl, $C_1$ alkyl, methyl, ethyl, isopropyl, and the like, wherein $R^1$ is optionally substituted with 1, 2, 3, 4, or 5 independently selected $R^b$ substituents.

In some embodiments, $R^1$ is $C_{1-6}$ alkoxy, for example, $C_6$ alkoxy, $C_5$ alkoxy, $C_4$ alkoxy, $C_3$ alkoxy, $C_2$ alkoxy, $C_1$ alkoxy, methoxy, ethoxy, isopropoxy, and the like, wherein $R^1$ is optionally substituted with 1, 2, 3, 4, or 5 independently selected $R^b$ substituents.

In some embodiments, $R^1$ is $C_{2-6}$ alkenyl, for example, $C_6$ alkenyl, $C_5$ alkenyl, $C_4$ alkenyl, $C_3$ alkenyl, $C_2$ alkenyl, ethenyl, propenyl, isopropenyl, and the like, wherein $R^1$ is optionally substituted with 1, 2, 3, 4, or 5 independently selected $R^b$ substituents.

In some embodiments, $R^1$ is $C_{2-6}$ alkynyl, for example, $C_6$ alkynyl, $C_5$ alkynyl, $C_4$ alkynyl, $C_3$ alkynyl, $C_2$ alkynyl, ethynyl, 2-propynyl (i.e., propargyl), and the like, substituted with 1, 2, 3, 4, or 5 independently selected $R^b$ substituents.

In some embodiments, $R^1$ is $C_{6-10}$ aryl, for example, $C_6$ aryl, $C_7$ aryl, $C_8$ aryl, $C_9$ aryl, $C_{10}$ aryl, phenyl, naphthyl, and the like, optionally substituted with 1, 2, 3, 4, or 5 independently selected $R^b$ substituents.

In some embodiments, $R^1$ is $C_{3-10}$cycloalkyl, for example, $C_{10}$cycloalkyl, $C_9$cycloalkyl, $C_8$cycloalkyl, $C_7$cycloalkyl, $C_6$ cycloalkyl, $C_5$ cycloalkyl, $C_4$ cycloalkyl, $C_3$ cycloalkyl, cyclopropyl, cyclobutyl, cyclopentyl, cyclohexyl, cycloheptyl and the like, optionally substituted with 1, 2, 3, 4, or 5 independently selected $R^b$ substituents. In some embodiments, $R^1$ is cyclopropyl, optionally substituted with 1, 2, 3, 4, or 5 independently selected $R^b$ substituents. In some embodiments, $R^1$ is cyclobutyl, optionally substituted with 1, 2, 3, 4, or 5 independently selected $R^b$ substituents.

In other embodiments, $R^1$ is a 5-14 membered heteroaryl, for example, 5 membered heteroaryl, 6 membered heteroaryl, 7 membered heteroaryl, 8 membered heteroaryl, 9 membered heteroaryl, 10 membered heteroaryl, 11 membered heteroaryl, 12 membered heteroaryl, 13 membered heteroaryl, 14 membered heteroaryl, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like, optionally substituted with 1, 2, 3, 4, or 5 independently selected $R^b$ substituents.

In other embodiments, $R^1$ is 4-10 membered heterocycloalkyl, for example, 10 membered heterocycloalkyl, 9 membered heterocycloalkyl, 8 membered heterocycloalkyl; 7 membered heterocycloalkyl, 6 membered heterocycloalkyl, 5 membered heterocycloalkyl, 4 membered heterocycloalkyl, piperidinyl, pyrrolidinyl, tetrahydropyranyl, tetrahydrofuranyl, oxetanyl, and the like, optionally substituted with 1, 2, 3, 4, or 5 independently selected $R^b$ substituents.

In other embodiments, $R^1$ is $C_{6-10}$ aryl-$C_{1-4}$ alkyl, for example, $C_{6-10}$ aryl-$C_1$ alkyl, $C_{6-10}$ aryl-$C_2$ alkyl, $C_{6-10}$ aryl-$C_3$ alkyl, $C_{6-10}$ aryl-$C_4$ alkyl, $C_6$ aryl-$C_1$ alkyl, $C_6$ aryl-$C_2$ alkyl, $C_6$ aryl-$C_3$ alkyl, $C_6$ aryl-$C_4$ alkyl, $C_{10}$ aryl-$C_1$ alkyl, $C_{10}$ aryl-$C_2$ alkyl, $C_{10}$ aryl-$C_3$ alkyl, $C_{10}$ aryl-$C_4$ alkyl, —$CH_2$-phenyl, —$CH_2CH_2$-phenyl, —$CH_2$-naphthyl, —$CH_2CH_2$-naphthyl, and the like, optionally substituted with 1, 2, 3, 4, or 5 independently selected $R^b$ substituents.

In other embodiments, $R^1$ is $C_{3-10}$ cycloalkyl-$C_{1-4}$ alkyl, for example, $C_{3-10}$ cycloalkyl-$C_1$ alkyl, $C_{3-10}$ cycloalkyl-$C_2$ alkyl, $C_{3-10}$ cycloalkyl-$C_3$ alkyl, $C_{3-10}$ cycloalkyl-$C_4$ alkyl, $C_{3-6}$ cycloalkyl-$C_1$ alkyl, $C_{3-6}$ cycloalkyl-$C_2$ alkyl, $C_{3-6}$ cycloalkyl-$C_3$ alkyl, $C_{3-6}$ cycloalkyl-$C_4$ alkyl, $C_5$-6 cycloalkyl-$C_1$ alkyl, $C_{5-6}$ cycloalkyl-$C_2$ alkyl, $C_{5-6}$ cycloalkyl-$C_3$ alkyl, $C_{5-6}$ cycloalkyl-$C_4$ alkyl, and the like, optionally substituted with 1, 2, 3, 4, or 5 independently selected $R^b$ substituents. In some embodiments, $R^1$ is cyclopropylmethyl, optionally substituted with 1, 2, 3, 4, or 5 independently selected $R^b$ substituents. In some embodiments, $R^1$ is cyclobutylmethyl, optionally substituted with 1, 2, 3, 4, or 5 independently selected $R^b$ substituents.

In other embodiments, $R^1$ is a 5-14 membered heteroaryl, for example, 5 membered heteroaryl, 6 membered heteroaryl, 7 membered heteroaryl, 8 membered heteroaryl, 9 membered heteroaryl, 10 membered heteroaryl, 11 membered heteroaryl, 12 membered heteroaryl, 13 membered heteroaryl, 14 membered heteroaryl, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like, optionally substituted with 1, 2, 3, 4, or 5 independently selected $R^b$ substituents.

In other embodiments, $R^1$ is 4-10 membered heterocycloalkyl, for example, 10 membered heterocycloalkyl, 9 membered heterocycloalkyl, 8 membered heterocycloalkyl; 7 membered heterocycloalkyl, 6 membered heterocycloalkyl, 5 membered heterocycloalkyl, 4 membered heterocycloalkyl, piperidinyl, pyrrolidinyl, tetrahydropyranyl, tetrahydrofuranyl, and the like, optionally substituted with 1, 2, 3, 4, or 5 independently selected $R^b$ substituents.

In some embodiments, $R^2$ and $R^3$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 3-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 3-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 4-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 5-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 6-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 6-membered cycloalkyl ring optionally substituted with 1, 2, 3, 4 or 5 independently selected $R^b$ substituents. In some embodiments, $R^2$ and $R^3$, together with the atom to which they are attached, form a 6-membered cycloalkyl ring optionally substituted with 1 selected $R^b$ substituent. In some embodiments, $R^2$ and $R^3$, together with the atom to which they are attached, form a 6-membered cycloalkyl ring optionally substituted with 2 independently selected $R^b$ substituents. In some embodiments, $R^2$ and $R^3$, together with the atom to which they are attached, form a 6-membered cycloalkyl ring optionally substituted with 3 independently selected $R^b$ substituents. In some embodiments, $R^2$ and $R^3$, together with the atom to which they are attached, form a 6-membered cycloalkyl ring optionally substituted with 4 independently selected $R^b$ substituents. In some embodiments, $R^2$ and $R^3$, together with the atom to which they are attached, form a 6-membered cycloalkyl ring optionally substituted with 5 independently selected $R^b$ substituents. In some embodiments, $R^2$ and $R^3$, together with the atom to which they are attached, form a 6-membered heterocycloalkyl ring optionally substituted with 1, 2, 3, 4 or 5 independently selected $R^b$ substituents. In some embodiments, $R^2$ and $R^3$, together with the atom to which they are attached, form a 7-membered cycloalkyl or heterocycloalkyl ring optionally substituted with 1, 2, 3, 4 or 5 independently selected $R^b$ substituents. In some embodiments, $R^2$ and $R^3$, together with the atom to which they are attached, form a 6-membered heterocycloalkyl ring optionally substituted with 1 selected $R^b$ substituent. In some embodiments, $R^2$ and $R^3$, together with the atom to which they are attached, form a 6-membered heterocycloalkyl ring optionally substituted with 2 independently selected $R^b$ substituents. In some embodiments, $R^2$ and $R^3$, together with the atom to which they are attached, form a 6-membered heterocycloalkyl ring optionally substituted with 3 independently selected $R^b$ substituents. In some embodiments, $R^2$ and $R^3$, together with the atom to which they are attached, form a 6-membered heterocycloalkyl ring optionally substituted with 4 independently selected $R^b$ substituents. In some embodiments, $R^2$ and $R^3$, together with the atom to which they are attached, form a 6-membered heterocycloalkyl ring optionally substituted with 5 independently selected $R^b$ substituents. In some embodiments, $R^2$ and $R^3$, together with the atom to which they are attached, form a 6-membered heterocycloalkyl ring optionally substituted with 1, 2, 3, 4 or 5 independently selected $R^b$ substituents.

In some embodiments, when Y is C—$R^5$, $R^2$ and $R^5$ together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents.

In some embodiments, Y is C—$R^5$, $R^3$ and $R^5$, together with the atoms to which they are attached, form a 3-, 4-, 5-, 6-, or 7-membered cycloalkyl or heterocycloalkyl ring optionally substituted with 1, 2, 3, 4 or 5 independently selected $R^b$ substituents.

In some embodiments, each $R^a$ is independently selected from H, D, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$alkyl, $C_{3-10}$ cycloalkyl-$C_{1-4}$ alkyl, (5-10 membered heteroaryl)-$C_{1-4}$ alkyl, and (4-14 membered heterocycloalkyl)-$C_{1-4}$ alkyl.

In some embodiments, when $R^a$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^a$ is optionally substituted with 1, 2, 3, 4, or 5 independently selected $R^d$ substituents.

In some embodiments, each $R^b$ substituent is independently selected from a bond, H, D, halo, oxo, $C_{1-10}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$; In some embodiments, when $R^b$ is $C_{1-10}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents.

In some embodiments, each $R^c$ is independently selected from H, D, OH, $C_{1-6}$ alkyl, $C_{1-6}$ alkoxy, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl.

In some embodiments, when $R^c$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^c$ is optionally substituted with 1, 2, 3, 4, or 5 independently selected $R^f$ substituents.

In some embodiments, each $R^f$ is independently selected from halogen, $C_{1-10}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^g$, $ORB$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^g C(=NR^g)NR^gR^g$, $NR^g C(=NOH)NR^gR^g$, $NR^gC(=NCN)NR^gR^g$, $SF_5$, $P(O)R^gR^g$, $P(O)(OR^g)(OR^g)$, $S(O)R^g$, $S(O)NR^gR^g$, $S(O)_2R^g$, $NR^gS(O)_2R^g$, $NR^g S(O)_2NR^gR^g$, and $S(O)_2NR^gR^g$;

In some embodiments, when $R^f$ is $C_{1-4}$alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R^n$ substituents.

In some embodiments, each $R^n$ is independently selected from $C_{1-10}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $NR^oC(=NOH)NR^oR^o$, $NR^oC(=NCN)NR^oR^o$, $SF_5$, $P(O)R^oR^o$, $P(O)(OR^o)(OR^o)$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$.

In some embodiments, each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^OC(=NCN)NR^eR^e$, $SF^5$, $P(O)R^eR^e$, $P(O)(OR^e)(OR^e)$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, In some embodiments, when $R^d$ is $C_{1-6}$alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected $R^f$ substituents.

In some embodiments, each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, In some embodiments, when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents.

In some embodiments, each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, In some embodiments, when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected $R^P$ substituents.

In some embodiments, each R is independently selected from $C_{1-10}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^r$, $OR^r$, $SR^r$, $C(O)R^r$, $C(O)NR'R'$, $C(O)OR^r$, $OC(O)R^r$, $OC(O)NR'R'$, $NHR^r$, $NR'R'$, $NR'C(O)R^r$, $NR'C(O)NR'R'$ $NR'C(O)OR^r$, $C(=NR')NR'R'$, $NR'C(=NR')NR'R'$, $NR'C(=NOH)NR'R'$, $NR'C(=NCN)$ NR'R", SF$_5$, P(O)R'R", P(O)(OR')(OR"), S(O)R', S(O)NR'R", S(O)$_2$R', NR'S(O)$_2$R", NR'S(O)$_2$NR'R", and S(O)$_2$NR'R".

In some embodiments, each R$^o$ or R$^r$ is independently selected from H, D, C$_{1-10}$ alkyl, C$_{3-6}$cycloalkyl, C$_{6-10}$ aryl, 5 or 6-membered heteroaryl, C$_{1-4}$ haloalkyl, C$_{2-4}$alkenyl, and C$_{2-4}$ alkynyl, In some embodiments, when R$^o$ or R$^r$ is C$_{1-10}$ alkyl, C$_{3-6}$ cycloalkyl, C$_{6-10}$ aryl, 5 or 6-membered heteroaryl, C$_{2-4}$ alkenyl, and C$_{2-4}$ alkynyl, then R$^o$ or R$^r$ is optionally substituted with 1, 2 or 3 independently selected R$^q$ substituents.

In some embodiments, each R$^q$ is independently selected from D, OH, CN, —COOH, NH$_2$, halo, C$_{1-6}$alkyl, C$_{1-6}$ haloalkyl, C$_{1-6}$ alkoxy, C$_{1-6}$ haloalkoxy, C$_{1-4}$ alkylthio, phenyl, 5-6 membered heteroaryl, C$_{3-6}$ cycloalkyl, 4-6 membered heterocycloalkyl, —CONHR$^{12}$, —NHC(O)R$^{12}$, —OC(O)R$^{12}$, —C(O)OR$^{12}$, —C(O)R$^{12}$, —SO$_2$R$^{12}$, —NHSO$_2$R$^{12}$, —SO$_2$NHR$^{12}$ and NR$^{12}$R$^{12}$, In some embodiments, when R$^q$ is C$_{1-6}$ alkyl, phenyl, 4-6 membered heterocycloalkyl or 5-6 membered heteroaryl, then R$^q$ is optionally substituted with OH, CN, —COOH, NH$_2$, C$_{1-6}$ alkoxy, C$_{3-6}$cycloalkyl or 4-6 membered heterocycloalkyl; and In some embodiments, each R$^{12}$ is independently C$_{1-6}$ alkyl.

In some embodiments, R$^2$ is C$_{1-6}$ alkyl, C$_{1-6}$ alkoxy, C$_{2-6}$alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$alkyl, (5-14 membered heteroaryl)-C$_{1-4}$ alkyl, or (4-14 membered heterocycloalkyl)-C$_{1-4}$ alkyl, each of which is optionally substituted with 1, 2, 3, 4 or 5 independently selected R$^b$ substituents and R$^b$ is as defined herein.

In some embodiments, R$^2$ is C$_{1-6}$ alkyl, which is optionally substituted with 1, 2, 3, 4 or 5 independently selected R$^b$ substituents and R$^b$ is as defined herein. In some embodiments, R$^2$ is ethyl with 1, 2, 3, 4 or 5 independently selected R$^b$ substituents. In some embodiments, R$^2$ is ethyl. In some embodiments, R$^2$ is methyl with 1, 2, or 3 independently selected R$^b$ substituents. In some embodiments, R$^2$ is propyl with 1, 2, 3, 4 or 5 independently selected R$^b$ substituents. In some embodiments, R$^2$ is butyl with 1, 2, 3, 4 or 5 independently selected R$^b$ substituents. In some embodiments, R$^2$ is pentyl with 1, 2, 3, 4 or 5 independently selected R$^b$ substituents. In some embodiments, R$^2$ is hexyl with 1, 2, 3, 4 or 5 independently selected R$^b$ substituents.

In some embodiments, R$^3$ is C$_{1-6}$ alkyl, C$_{1-6}$ alkoxy, C$_{2-6}$alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$alkyl, (5-14 membered heteroaryl)-C$_{1-4}$ alkyl, or (4-14 membered heterocycloalkyl)-C$_{1-4}$ alkyl, each of which is optionally substituted with 1, 2, 3, 4 or 5 independently selected R$^b$ substituents and R$^b$ is as defined herein.

In some embodiments, R$^3$ is C$_{1-6}$ alkyl, which is optionally substituted with 1, 2, 3, 4 or 5 independently selected R$^b$ substituents and R$^b$ is as defined herein. In some embodiments, R$^3$ is ethyl with 1, 2, 3, 4 or 5 independently selected R$^b$ substituents. In some embodiments, R$^3$ is ethyl. In some embodiments, R$^3$ is methyl with 1, 2, or 3 independently selected R$^b$ substituents. In some embodiments, R$^3$ is propyl with 1, 2, 3, 4 or 5 independently selected R$^b$ substituents. In some embodiments, R$^3$ is butyl with 1, 2, 3, 4 or 5 independently selected R$^b$ substituents. In some embodiments, R$^3$ is pentyl with 1, 2, 3, 4 or 5 independently selected R$^b$ substituents. In some embodiments, R$^3$ is hexyl with 1, 2, 3, 4 or 5 independently selected R$^b$ substituents.

In some embodiments, R$^2$ and R$^3$, together with the atom to which they are attached, form a 3-, 4-, 5-, 6-, or 7-membered cycloalkyl or heterocycloalkyl ring optionally substituted with 1, 2, 3, 4 or 5 independently selected R$^b$ substituents, and R$^b$ is as defined herein.

In some embodiments, R$^2$ and R$^3$, together with the atom to which they are attached, form a 3-, 4-, 5-, 6-, or 7-membered cycloalkyl ring optionally substituted with 1, 2, 3, 4 or 5 independently selected R$^b$ substituents, and R$^b$ is as defined herein.

In some embodiments, R$^2$ and R$^3$, together with the atom to which they are attached, form a 6-membered heterocycloalkyl ring optionally substituted with 1, 2, 3, 4 or 5 independently selected R$^b$ substituents and R$^b$ is as defined herein. In some embodiments, R$^2$ and R$^3$, together with the atom to which they are attached, form a 4-membered azetidine optionally substituted with 1, 2, 3, 4 or 5 independently selected R$^b$ substituents and R$^b$ is as defined herein.

In some embodiments, R$^2$ and R$^3$, together with the atom to which they are attached, form a 6-membered cycloalkyl ring optionally substituted with 1 R$^b$ substituent and R$^b$ is as defined herein. In some embodiments, R$^b$ is D, halo, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$), NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)(=NR$^c$)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$ and R$^c$ is as defined herein. In some embodiments, R$^c$ is H. In some embodiments, R$^b$ is OH or COOH.

In some embodiments, compounds have a formula of

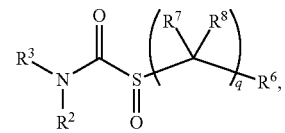

Formula (II)

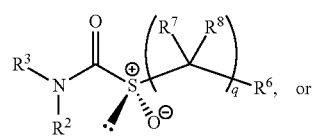

Formula (II-a)

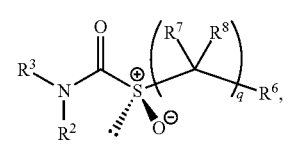

Formula (II-b)

or pharmaceutically acceptable salts or solvates thereof.

In some embodiments, q is 0-6. In some embodiments, q is 0-5. In some embodiments, q is 0-4. In some embodiments, q is 0-3. In some embodiments, q is 0-2. In some embodiments, q is 0-1. In some embodiments, q is 1-6. In some embodiments, q is 1-5. In some embodiments, q is 1-4. In some embodiments, q is 1-3. In some embodiments, q is 1-2. In some embodiments, q is 2-6. In some embodiments, q is 2-5. In some embodiments, q is 2-4. In some embodiments, q is 2-3. In some embodiments, q is 3-6. In some embodiments, q is 3-5. In some embodiments, q is 3-4. In some embodiments, q is 4-6. In some embodiments, q is 0. In some embodiments, q is 1. In some embodiments, q is 2.

In some embodiments, q is 3. In some embodiments, q is 4. In some embodiments, q is 5. In some embodiments, q is 6.

In some embodiments, $R^6$, $R^7$, and $R^8$ are each independently H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, NH a $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$;

In some embodiments, when $R^6$, $R^7$, or $R^8$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^6$, $R^7$, or $R^8$ is optionally substituted with 1, 2, 3, 4 or 5 independently selected $R^b$ substituents.

In some embodiments, $R^7$ and $R^8$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents. $R^7$ and $R^8$, together with the atom to which they are attached, form a 7-membered cycloalkyl or heterocycloalkyl ring optionally substituted with 1, 2, 3, 4 or 5 independently selected $R^b$ substituents. $R^7$ and $R^8$, together with the atom to which they are attached, form a 6-membered cycloalkyl or heterocycloalkyl ring optionally substituted with 1, 2, 3, 4 or 5 independently selected $R^b$ substituents. $R^7$ and $R^8$, together with the atom to which they are attached, form a 5-membered cycloalkyl or heterocycloalkyl ring optionally substituted with 1, 2, 3, 4 or 5 independently selected $R^b$ substituents. $R^7$ and $R^8$, together with the atom to which they are attached, form a 4-membered cycloalkyl or heterocycloalkyl ring optionally substituted with 1, 2, 3, 4 or 5 independently selected $R^b$ substituents. $R^7$ and $R^8$, together with the atom to which they are attached, form a 3-membered cycloalkyl or heterocycloalkyl ring optionally substituted with 1, 2, 3, or 4 independently selected $R^b$ substituents. $R^7$ and $R^8$, together with the atom to which they are attached, form a 3-membered cycloalkyl or heterocycloalkyl ring optionally substituted with 4 independently selected $R^b$ substituents. $R^7$ and $R^8$, together with the atom to which they are attached, form a 3-membered cycloalkyl or heterocycloalkyl ring optionally substituted with 3 independently selected $R^b$ substituents. In some embodiments, $R^a$, $R^b$, $R^2$, and $R^3$ are as defined herein. $R^7$ and $R^8$, together with the atom to which they are attached, form a 3-membered cycloalkyl or heterocycloalkyl ring optionally substituted with 2 independently selected $R^b$ substituents. $R^7$ and $R^8$, together with the atom to which they are attached, form a 3-membered cycloalkyl or heterocycloalkyl ring optionally substituted with 1 $R^b$ substituent.

In some embodiments, $R^7$ and $R^8$ are each independently H, or $C_{1-6}$ alkyl optionally substituted with 1, 2, 3, 4 or 5 independently selected $R^b$ substituents and $R^b$ is as defined herein. In some embodiments, wherein $R^7$ is H. In some embodiments, $R^8$ are H.

In some embodiments, $R^6$ is H, D, halo, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR$, $NR^cC(=NR^c)$ $NR^cR^c$, $NR^cC(=NOH)NR^cR^c$, $NR^cC(=NCN)NR^cR^c$, $SF_5$, $P(O)R^cR^c$, $P(O)(OR^c)(OR^c)$ $NHR^c$, $NR^cR^c$, $NR^cC(O)R^c$, $NR^cC(O)OR^c$, $NR^cC(O)NR^cR^c$, $NR^cS(O)R^c$, $NR^cS(O)$ $(=NR^c)R^c$, $NR^cS(O)_2R^c$, $NR^cS(O)_2NR^cR^c$, $S(O)R^c$, $S(O)$ $NR^cR^c$, $S(O)_2R^c$ or $S(O)_2NR^cR^c$ and $R^c$ is as defined herein. In some embodiments, $R^c$ is H.

In some embodiments, $R^6$ is $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, each of which is optionally substituted with 1, 2, 3, 4 or 5 independently selected $R^b$ substituents and wherein $R^b$ is as defined herein.

In some embodiments, $R^6$ is $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, each of which is optionally substituted with 1, 2, 3, 4 or 5 independently selected $R^b$ substituents and wherein $R^b$ is as defined herein. In some embodiments, $R^6$ is $C_{3-10}$ cycloalkyl or 4-14 membered heterocycloalkyl, each of which is optionally substituted with 1, 2, 3, 4 or 5 independently selected $R^b$ substituents and wherein $R^b$ is as defined herein. In some embodiments, $R^6$ is $C_{3-10}$ cycloalkyl, which is optionally substituted with 1, 2, 3, 4 or 5 independently selected $R^b$ substituents and wherein $R^b$ is as defined herein. In some embodiments, $R^6$ is $C_{3-6}$ cycloalkyl, each of which is optionally substituted with 1, 2, 3, 4 or 5 independently selected $R^b$ substituents and wherein $R^b$ is as defined herein. In some embodiments, $R^6$ is $C_3$ cycloalkyl, each of which is optionally substituted with 1, 2, 3, 4 or 5 independently selected $R^b$ substituents and wherein $R^b$ is as defined herein.

In some embodiments, the compound has a formula of Formula (XII), Formula (XII-a), or

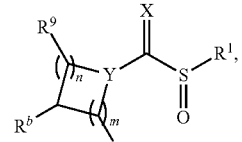

Formula (XII)

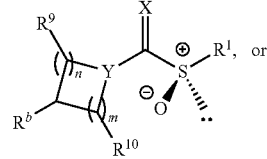

Formula (XII-a)

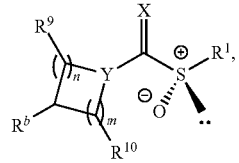

Formula (XII-b)

or a pharmaceutically acceptable salt or solvate thereof. In some embodiments, $R^1$ is $C_{1-6}$ alkyl. In some embodiments, $R^1$ is methyl.

In some embodiments, the compound has a formula of Formula (XIII), Formula (XIII-a), or Formula (XIII-b)

Formula (XIII)

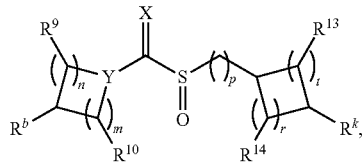

Formula (XIII-a)

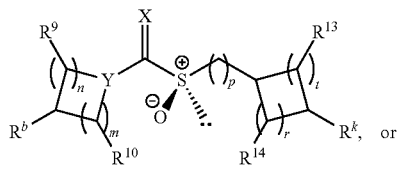
, or

Formula (XIII-b)

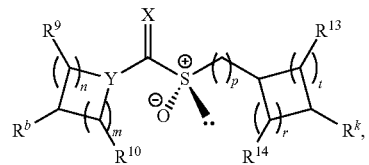
, a pharmaceutically acceptable salt or solvate thereof. In some embodiments, X is O. In some embodiments, Y is N. In some embodiments, $R^1$ is $C_{1-6}$ alkyl. In some embodiments, $R^1$ is methyl.

In some embodiments, n is 0-6. In some embodiments, n is 0-5. In some embodiments, n is 0-4. In some embodiments, n is 0-3. In some embodiments, n is 0-2. In some embodiments, n is 0-1. In some embodiments, n is 1-6. In some embodiments, n is 1-5. In some embodiments, n is 1-4. In some embodiments, n is 1-3. In some embodiments, n is 1-2. In some embodiments, n is 2-6. In some embodiments, n is 2-5. In some embodiments, n is 2-4. In some embodiments, n is 2-3. In some embodiments, n is 3-6. In some embodiments, n is 3-5. In some embodiments, n is 3-4. In some embodiments, n is 4-6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, m is 0-6. In some embodiments, m is 0-5. In some embodiments, m is 0-4. In some embodiments, m is 0-3. In some embodiments, m is 0-2. In some embodiments, m is 0-1. In some embodiments, m is 1-6. In some embodiments, m is 1-5. In some embodiments, m is 1-4. In some embodiments, m is 1-3. In some embodiments, m is 1-2. In some embodiments, m is 2-6. In some embodiments, m is 2-5. In some embodiments, m is 2-4. In some embodiments, m is 2-3. In some embodiments, m is 3-6. In some embodiments, m is 3-5. In some embodiments, m is 3-4. In some embodiments, m is 4-6. In some embodiments, m is 0. In some embodiments, m is 1. In some embodiments, m is 2. In some embodiments, m is 3. In some embodiments, m is 4. In some embodiments, m is 5. In some embodiments, m is 6.

In some embodiments, n and m together are 4. In some embodiments, n and m together are 3. In some embodiments, n and m together are 2.

In some embodiments, t is 0-6. In some embodiments, t is 0-5. In some embodiments, t is 0-4. In some embodiments, t is 0-3. In some embodiments, t is 0-2. In some embodiments, t is 0-1. In some embodiments, t is 1-6. In some embodiments, t is 1-5. In some embodiments, t is 1-4. In some embodiments, t is 1-3. In some embodiments, t is 1-2. In some embodiments, t is 2-6. In some embodiments, t is 2-5. In some embodiments, t is 2-4. In some embodiments, t is 2-3. In some embodiments, t is 3-6. In some embodiments, t is 3-5. In some embodiments, t is 3-4. In some embodiments, t is 4-6. In some embodiments, t is 0. In some embodiments, t is 1. In some embodiments, t is 2. In some embodiments, t is 3. In some embodiments, t is 4. In some embodiments, t is 5. In some embodiments, t is 6.

In some embodiments, r is 0-6. In some embodiments, r is 0-5. In some embodiments, r is 0-4. In some embodiments, r is 0-3. In some embodiments, r is 0-2. In some embodiments, r is 0-1. In some embodiments, r is 1-6. In some embodiments, r is 1-5. In some embodiments, r is 1-4. In some embodiments, r is 1-3. In some embodiments, r is 1-2. In some embodiments, r is 2-6. In some embodiments, r is 2-5. In some embodiments, r is 2-4. In some embodiments, r is 2-3. In some embodiments, r is 3-6. In some embodiments, r is 3-5. In some embodiments, r is 3-4. In some embodiments, r is 4-6. In some embodiments, r is 0. In some embodiments, r is 1. In some embodiments, r is 2. In some embodiments, r is 3. In some embodiments, r is 4. In some embodiments, r is 5. In some embodiments, r is 6.

In some embodiments, r and t together are 2. In some embodiments, r and t together are 1.

In some embodiments, $R^9$ is H, D, halo, oxo, alkyl, alkoxy, alkenyl, alkynyl, haloalkyl, haloalkoxy, aryl, cycloalkyl, heteroaryl, heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$ and $R^a$ is as defined in the embodiments as described herein. In some embodiments, $R^9$ is H.

In some embodiments, $R^{10}$ is H, D, halo, oxo, alkyl, alkoxy, alkenyl, alkynyl, haloalkyl, haloalkoxy, aryl, cycloalkyl, heteroaryl, heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$ $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$ and $R^a$ is as defined in the embodiments as described herein. In some embodiments, $R^{10}$ is H.

In some embodiments, p is 0-6. In some embodiments, p is 0-5. In some embodiments, p is 0-4. In some embodiments, p is 0-3. In some embodiments, p is 0-2. In some embodiments, p is 0-1. In some embodiments, p is 1-6. In some embodiments, p is 1-5. In some embodiments, p is 1-4. In some embodiments, p is 1-3. In some embodiments, p is 1-2. In some embodiments, p is 2-6. In some embodiments, p is 2-5. In some embodiments, p is 2-4. In some embodiments, p is 2-3. In some embodiments, p is 3-6. In some embodiments, p is 3-5. In some embodiments, p is 3-4. In some embodiments, p is 4-6. In some embodiments, p is 0. In some embodiments, p is 1. In some embodiments, p is 2. In some embodiments, p is 3. In some embodiments, p is 4. In some embodiments, p is 5. In some embodiments, p is 6.

In some embodiments, $R^{13}$ is H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$ NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$ NR$^a$C(=NCN) NR$^a$R$^a$, NR$^a$S(O)R$^a$, NR$^a$S(O)$_2$R$^a$, NR$^a$S(O)$_2$NR$^a$R$^a$, S(O) R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$. In some embodiments, $R^{13}$ is H. In some embodiments, $R^a$ is H.

In some embodiments, $R^{14}$ is H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$, NR$^a$C(=NCN) NR$^a$R$^a$, NR$^a$S(O)R$^a$, NR$^a$S(O)$_2$R$^a$, NR$^a$S(O)$_2$NR$^a$R$^a$, S(O) R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$. In some embodiments, $R^{14}$ is H.

In some embodiments, each $R^k$ substituent is independently selected from a bond, H, D, halo, oxo, $C_{1-10}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$) NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$), NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NRS(O) (=NR$^c$)R$^c$, NR$^c$S(O)$_2$R$^c$, NR$^c$S(O)$_2$NR$^c$R$^c$, S(O)R$^c$, S(O) NR$^c$R$^c$, S(O)$_2$R$^c$ or S(O)$_2$NR$^c$R$^c$; In some embodiments, when $R^k$ is $C_{1-10}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents and $R^a$, $R^b$, $R^c$, and $R^d$ are as defined in the embodiments as described herein. In some embodiments, $R^k$ is H. In some embodiments, $R^b$ is H. In some embodiments, $R^c$ is H.

In some embodiments, compounds have a formula of

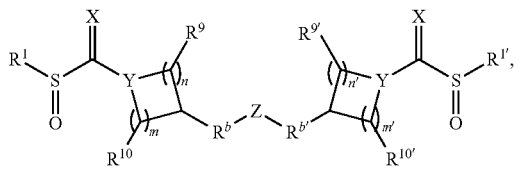

Formula (IV)

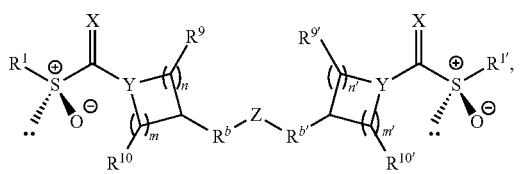

Formula (V)

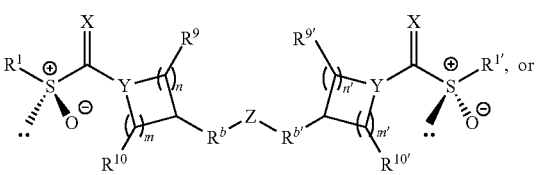

Formula (VI)

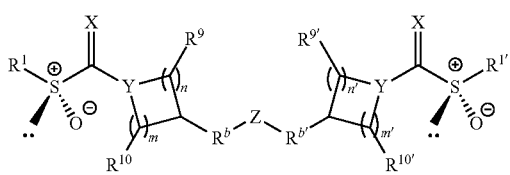

Formula (VII)

or pharmaceutically acceptable salts or solvates thereof.

In some embodiments, n, m, n', and m' are each independently 0-10.

In some embodiments, Z is a bond, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, —C(O)O(CH$_2$)$_v$CH$_2$O(O)C—, —OC(O)CH=CH(O) CO—, —OC(O)CH$_2$(CH$_2$)$_v$(O)CO—, —OC(O)N(CH$_3$) (CH$_2$)$_v$CH$_2$N(CH$_3$)(O)CO—, —OC(O)N(CH$_3$)CH$_2$ (CH$_2$)$_v$CH$_2$N(CH$_3$)(O)CO—, —OC(O)N(H)CH$_2$ (CH$_2$)$_v$CH$_2$N(H)(O)CO—, —C(O)—, —OC(O)—, —OC (O)O—, —C(O)O—, —C(S)—, —OC(S)—, —OC(S)O—, —C(O)O—, —C(=NR$^a$)—, —S—, —S—S—, —S(O)—, —S(O)$_2$—, —C(R$^a$)$_2$—, —N(R$^a$)—, —S(O)(R$^a$)—, —S(O) N(R$^a$)—, —P(O)(R$^a$)—, —P(O)(OR$^a$)—, and —B(OR$^a$)—, and —S(O)$_2$N(R$^a$)—.

In some embodiments, v is 0-10. In some embodiments, v is 0-9. In some embodiments, v is 0-8. In some embodiments, v is 0-7. In some embodiments, v is 0-6. In some embodiments, v is 0-5. In some embodiments, v is 0-4. In some embodiments, v is 0-3. In some embodiments, v is 0-2. In some embodiments, v is 0-1. In some embodiments, v is 1-10. In some embodiments, v is 1-9. In some embodiments, v is 1-8. In some embodiments, v is 1-7. In some embodiments, v is 1-6. In some embodiments, v is 1-5. In some embodiments, v is 1-4. In some embodiments, v is 1-3. In some embodiments, v is 1-2. In some embodiments, v is 2-10. In some embodiments, v is 2-9. In some embodiments, v is 2-8. In some embodiments, v is 2-7. In some embodiments, v is 2-6. In some embodiments, v is 2-5. In some embodiments, v is 2-4. In some embodiments, v is 2-3. In some embodiments, v is 3-10. In some embodiments, v is 3-9. In some embodiments, v is 3-8. In some embodiments, v is 3-7. In some embodiments, v is 3-6. In some embodiments, v is 3-5. In some embodiments, v is 3-4. In some embodiments, v is 4-10. In some embodiments, v is 4-9. In some embodiments, v is 4-8. In some embodiments, v is 4-7. In some embodiments, v is 4-6. In some embodiments, v is 4-5. In some embodiments, v is 5-10. In some embodiments, v is 5-9. In some embodiments, v is 5-8. In some embodiments, v is 5-7. In some embodiments, v is 5-6. In some embodiments, v is 6-10. In some embodiments, v is 6-9. In some embodiments, v is 6-8. In some embodiments, v is 6-7. In some embodiments, v is 7-10. In some embodiments, v is 7-9. In some embodiments, v is 7-8. In some embodiments, v is 8-10. In some embodiments, v is 8-9. In some embodiments, v is 9-10. In some embodiments, v is 0. In some embodiments, v is 1. In some embodiments, v is 2. In some embodiments, v is 3. In some embodiments, v is 4. In some embodiments, v is 5. In some embodiments, v is 6. In some embodiments, v is 7. In some embodiments, v is 8. In some embodiments, v is 9. In some embodiments, v is 10. In some embodiments, $R^9$, $R^{10}$, $R^{9'}$, $R^{10'}$, $R^1$, and $R^{1'}$ are each independently H, D, halo, oxo, alkyl, alkoxy, alkenyl, alkynyl, haloalkyl, haloalkoxy, aryl, cycloalkyl, heteroaryl, heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $SF_5$, $P(O)R^aR^a$, $P(O)(OR^a)(OR^a)$, $B(OR^a)_2$ and $S(O)_2NR^aR^a$.

In some embodiments, $R^9$ and $R^{9'}$ are the same.
In some embodiments, $R^{10}$ and $R^{10'}$ are the same.
In some embodiments, $R^9$, $R^{9'}$ $R^{10}$, and $R^{10'}$ are H
In some embodiments, each $R^b$ substituent and each $R^{b'}$ substituent are independently selected from a bond, H, D, halo, oxo, $C_{1-10}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$ $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$;

In some embodiments, when $R^b$ or $R^{b'}$ is $C_{1-10}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents.

In some embodiments, n is 2. In some embodiments, m is 2. In some embodiments, n and m together are 4. In some embodiments, both n and m are 2. In some embodiments, n' is 2. In some embodiments, m' is 2. In some embodiments, n' and m' together are 4. In some embodiments, both n' and m are 2. In some embodiments, when n and m are together 4, n' and m' together are 4. In some embodiments, $R^9$, $R^{9'}$ $R^{10}$, and $R^{10'}$ are H.

In some embodiments, compounds have a formula of

Formula (IV-I)

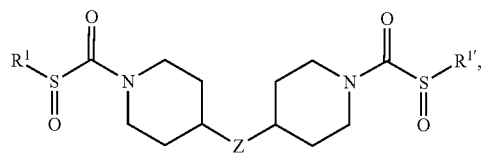

Formula (V-I)

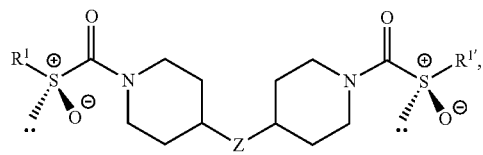

Formula (VI-I)

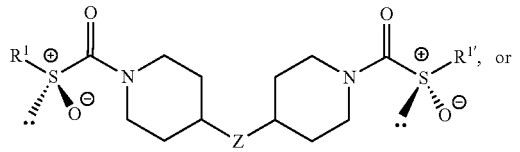

Formula (VII-I)

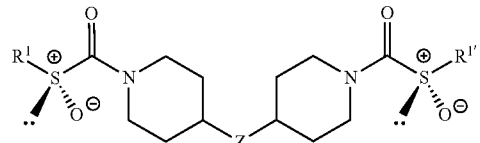

or pharmaceutically acceptable salts or solvates thereof.

In some embodiments, $R^1$ and $R^{1'}$ are the same. In some embodiments, $R^1$ and $R^{1'}$ are cyclopropylmethyl.

In some embodiments, Z is —OC(O)O—, —OC(O)CH=CH(O)CO—, —OC(O)CH_2(CH_2)_v(O)CO—, —C(O)OCH_2CH_2O(O)C—, or —OC(O)N(CH_3)CH_2CH_2CH_2N(CH_3)(O)CO—. In some embodiments, Z is —OC(O)O—. In some embodiments, Z is —C(O)OCH_2CH_2O(O)C. In some embodiments, Z is —OC(O)N(CH_3)CH_2CH_2CH_2N(CH_3)(O)CO—. In some embodiments, Z is a bond. In some embodiments, Z is oxo. In some embodiments, Z is $C_{1-6}$ alkyl. In some embodiments, Z is $C_{1-6}$ alkoxy. In some embodiments, Z is $C_{2-6}$ alkenyl. In some embodiments, Z is $C_{2-6}$ alkynyl. In some embodiments, Z is $C_{1-6}$ haloalkyl. In some embodiments, Z is $C_{1-6}$ haloalkoxy. In some embodiments, Z is $C_{6-10}$ aryl. In some embodiments, Z is $C_{3-10}$ cycloalkyl. In some embodiments, Z is 5-10 membered heteroaryl. In some embodiments, Z is 4-14 membered heterocycloalkyl. In some embodiments, Z is $C_{6-10}$ aryl-$C_{1-4}$ alkyl. In some embodiments, Z is $C_{3-10}$ cycloalkyl-$C_{1-4}$alkyl. In some embodiments, Z is (5-14 membered heteroaryl)-$C_{1-4}$ alkyl. In some embodiments, Z is (4-14 membered heterocycloalkyl)-$C_{1-4}$ alkyl. In some embodiments, Z is —C(O)—. In some embodiments, Z is —OC(O)—. In some embodiments, Z is —C(O)O—. In some embodiments, Z is —C(S)—. In some embodiments, Z is —OC(S)—. In some embodiments, Z is —OC(S)O—. In some embodiments, Z is —C(O)O—. In some embodiments, Z is —C(=$NR^a$)—. In some embodiments, Z is —S(O)—. In some embodiments, Z is —S(O)_2—. In some embodiments, Z is —N($R^a$)—. In some embodiments, Z is —S(O)($R^a$)—. In some embodiments, Z is —S(O)N($R^a$)—. In some embodiments, Z is —P(O)($R^a$)—. In some embodiments, Z is —P(O)(O$R^a$)—. In some embodiments, Z is and —B(O$R^a$)—. In some embodiments, Z is —S(O)_2N($R^a$)—. In some embodiments, Z is

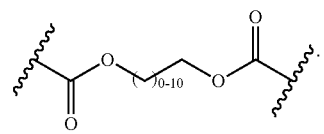

In some embodiments, Z is

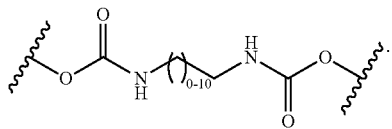

In some embodiments, Z is

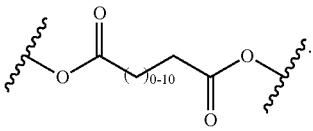

In some embodiments, Z is

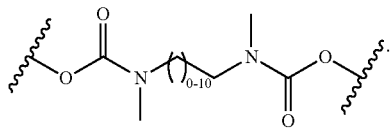

In some embodiments, $R^1$ and $R^{1'}$ are cyclopropylmethyl.

In some embodiments, the compound has a formula of Formula (VIII), Formula (IX), Formula (X), or Formula (XI):

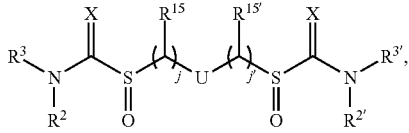
Formula (VIII)

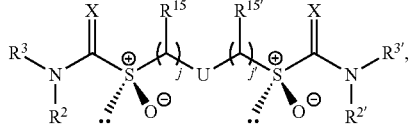
Formula (IX)

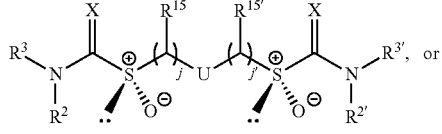
Formula (X)

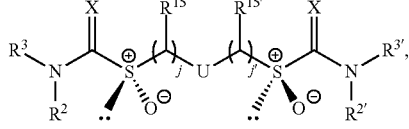
Formula (XI)

or a pharmaceutically acceptable salt or solvate thereof. In some embodiments, X is O. In some embodiments, Y is N.

In some embodiments, j is 0-6. In some embodiments, j is 0-5. In some embodiments, j is 0-4. In some embodiments, j is 0-3. In some embodiments, j is 0-2. In some embodiments, j is 0-1. In some embodiments, j is 1-6. In some embodiments, j is 1-5. In some embodiments, j is 1-4. In some embodiments, j is 1-3. In some embodiments, j is 1-2. In some embodiments, j is 2-6. In some embodiments, j is 2-5. In some embodiments, j is 2-4. In some embodiments, j is 2-3. In some embodiments, j is 3-6. In some embodiments, j is 3-5. In some embodiments, j is 3-4. In some embodiments, j is 4-6. In some embodiments, j is 0. In some embodiments, j is 1. In some embodiments, j is 2. In some embodiments, j is 3. In some embodiments, j is 4. In some embodiments, j is 5. In some embodiments, j is 6.

In some embodiments, j' is 0-6. In some embodiments, j' is 0-5. In some embodiments, j' is 0-4. In some embodiments, j' is 0-3. In some embodiments, j' is 0-2. In some embodiments, j' is 0-1. In some embodiments, j' is 1-6. In some embodiments, j' is 1-5. In some embodiments, j' is 1-4. In some embodiments, j' is 1-3. In some embodiments, j' is 1-2. In some embodiments, j' is 2-6. In some embodiments, j' is 2-5. In some embodiments, j' is 2-4. In some embodiments, j' is 2-3. In some embodiments, j' is 3-6. In some embodiments, j' is 3-5. In some embodiments, j' is 3-4. In some embodiments, j' is 4-6. In some embodiments, j' is 0. In some embodiments, j' is 1. In some embodiments, j' is 2. In some embodiments, j' is 3. In some embodiments, j' is 4. In some embodiments, j' is 5. In some embodiments, j' is 6.

U is a bond, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, —C(O)—, —OC(O)—, —OC(O)O—, —OC(O)CH=CH(O)CO—, —OC(O)CH$_2$(CH$_2$)$_w$(O)CO—, —C(O)O(CH$_2$)$_w$CH$_2$O(O)C—, —OC(O)N(CH$_3$)(CH$_2$)$_w$CH$_2$N(CH$_3$)(O)CO—, —OC(O)N(CH$_3$)CH$_2$(CH$_2$)$_w$CH$_2$N(CH$_3$)(O)CO—, —C(O)O—, —C(S)—, —OC(S)—, —OC(S)O—, —C(O)O—, —C(=NR$^a$)—, —S—, —S—S—, —S(O)—, —S(O)$_2$—, —C(R$^a$)$_z$—, —N(R$^a$)—, —S(O)(R$^a$)—, —S(O)N(R$^a$)—, —P(O)(R$^a$)—, —P(O)(OR$^a$)—, and —B(OR$^a$)—, and —S(O)$_2$N(R$^a$)—.

In some embodiments, w is 0-10. In some embodiments, w is 0-9. In some embodiments, w is 0-8. In some embodiments, w is 0-7. In some embodiments, w is 0-6. In some embodiments, w is 0-5. In some embodiments, w is 0-4. In some embodiments, w is 0-3. In some embodiments, w is 0-2. In some embodiments, w is 0-1. In some embodiments, w is 1-10. In some embodiments, w is 1-9. In some embodiments, w is 1-8. In some embodiments, w is 1-7. In some embodiments, w is 1-6. In some embodiments, w is 1-5. In some embodiments, w is 1-4. In some embodiments, w is 1-3. In some embodiments, w is 1-2. In some embodiments, w is 2-10. In some embodiments, w is 2-9. In some embodiments, w is 2-8. In some embodiments, w is 2-7. In some embodiments, w is 2-6. In some embodiments, w is 2-5. In some embodiments, w is 2-4. In some embodiments, w is 2-3. In some embodiments, w is 3-10. In some embodiments, w is 3-9. In some embodiments, w is 3-8. In some embodiments, w is 3-7. In some embodiments, w is 3-6. In some embodiments, w is 3-5. In some embodiments, w is 3-4. In some embodiments, w is 4-10. In some embodiments, w is 4-9. In some embodiments, w is 4-8. In some embodiments, w is 4-7. In some embodiments, w is 4-6. In some embodiments, w is 4-5. In some embodiments, w is 5-10. In some embodiments, w is 5-9. In some embodiments, w is 5-8. In some embodiments, w is 5-7. In some embodiments, w is 5-6. In some embodiments, w is 6-10. In some embodiments, w is 6-9. In some embodiments, w is 6-8. In some embodiments, w is 6-7. In some embodiments, w is 7-10. In some embodiments, w is 7-9. In some embodiments, w is 7-8. In some embodiments, w is 8-10. In some embodiments, w is 8-9. In some embodiments, w is 9-10. In some embodiments, w is 0. In some embodiments, w is 1. In some embodiments, w is 2. In some embodiments, w is 3. In some embodiments, w is 4. In some embodiments, w is 5. In some embodiments, w is 6. In some embodiments, w is 7. In some embodiments, w is 8. In some embodiments, w is 9. In some embodiments, w is 10. In some embodiments, $R^{2'}$, $R^{3'}$, $R^{15}$, and $R^{15'}$ are each independently H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$.

In some embodiments, $R^{15}$ and $R^{15'}$ are the same. In some embodiments, $R^{15}$ and $R^{15'}$ are H. In some embodiments, compounds have a formula of Formula (VIII), Formula (IX), Formula (X) or Formula (IX),

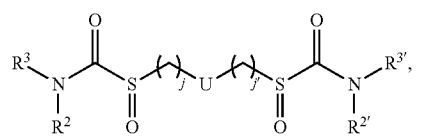

Formula (VIII)

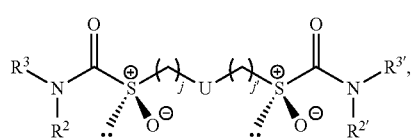

Formula (IX)

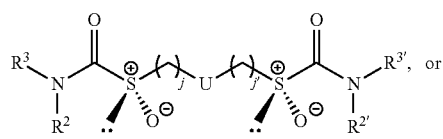

Formula (X)

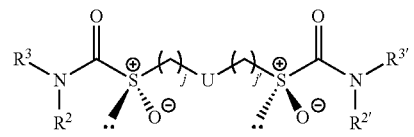

Formula (XI)

or a pharmaceutically acceptable salt or solvate thereof. In some embodiments, $R^2$ and $R^{2'}$ are the same. In some embodiments, $R^2$ and $R^{2'}$ are ethyl. In some embodiments, $R^3$ and $R^{3'}$ are the same. In some embodiments, $R^3$ and $R^{3'}$ are ethyl. In some embodiments, j and j' are the same. In some embodiments, j and j' are 2. In some embodiments, Z is —OC(O)O—, —C(O)OCH$_2$CH$_2$O(O)C—, —OC(O)N(H)CH$_2$CH$_2$N(H)(O)CO—, —OC(O)N(CH$_3$)CH$_2$CH$_2$N(CH$_3$)(O)CO—, or —OC(O)N(CH$_3$)CH$_2$CH$_2$CH$_2$N(CH$_3$)(O)CO—.

In some embodiments, compounds have a formula of

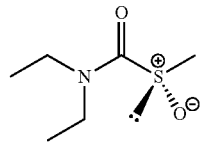 or 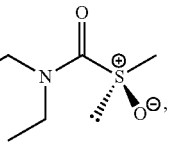

or a pharmaceutically acceptable salt or solvates thereof. In some embodiments, compounds have a formula of

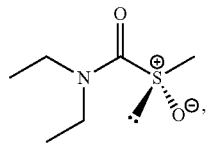

or a pharmaceutically acceptable salt or solvates thereof. In some embodiments, compounds have a formula of or

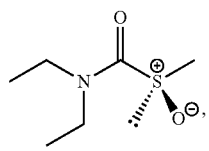

or a pharmaceutically acceptable salt or solvates thereof.
In some embodiments, compounds have a formula of

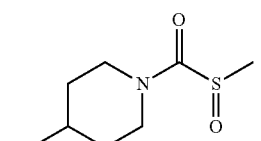

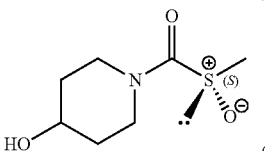

, or

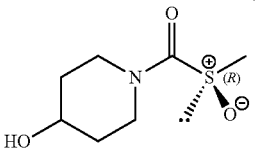

, or a pharmaceutically acceptable salt or solvates thereof. In some embodiments, compounds have a formula of, or a pharmaceutically acceptable salt or solvates thereof

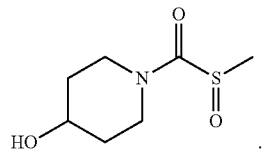

In some embodiments, compounds have a formula of

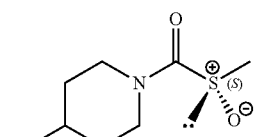

, or a pharmaceutically acceptable salt or solvates thereof. In some embodiments, compounds have a formula of
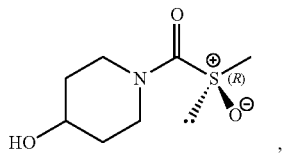,
or a pharmaceutically acceptable salt or solvates thereof.
In some embodiments, compounds have a formula of
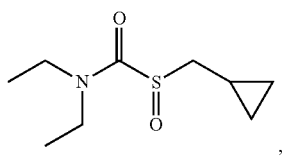,
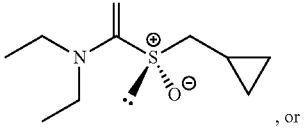, or
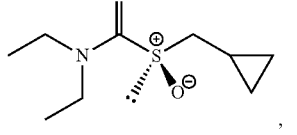,
or pharmaceutically acceptable salts or solvates thereof.
In some embodiments, compounds are selected from the group consisting of:
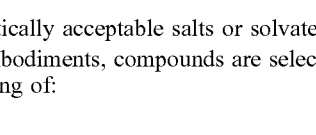
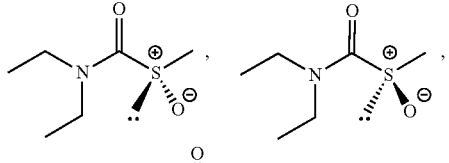,
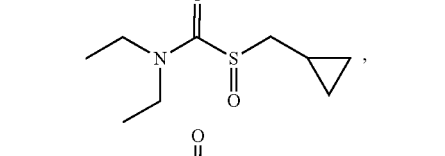,
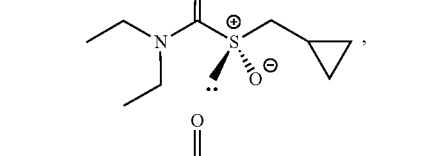,
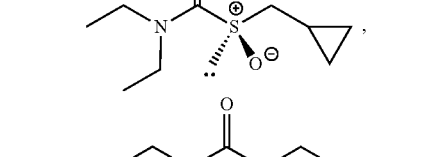,
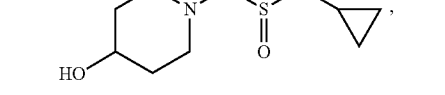
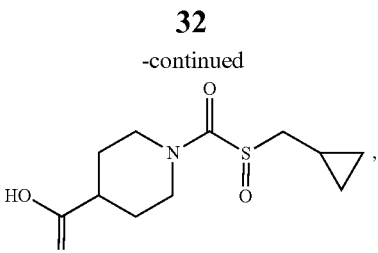,
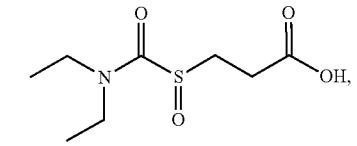
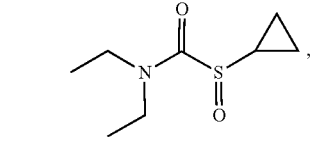,
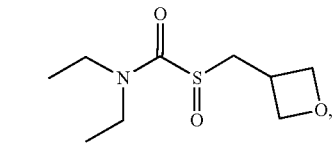,
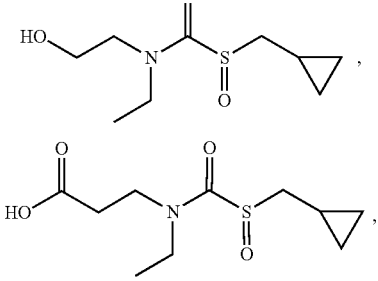,
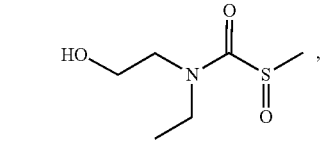,
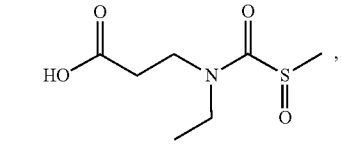,
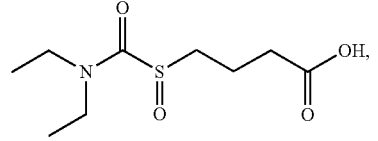
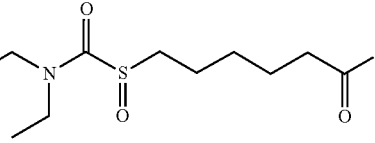,
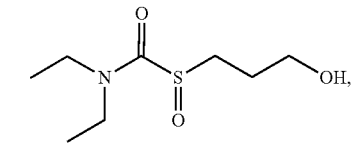

33
-continued
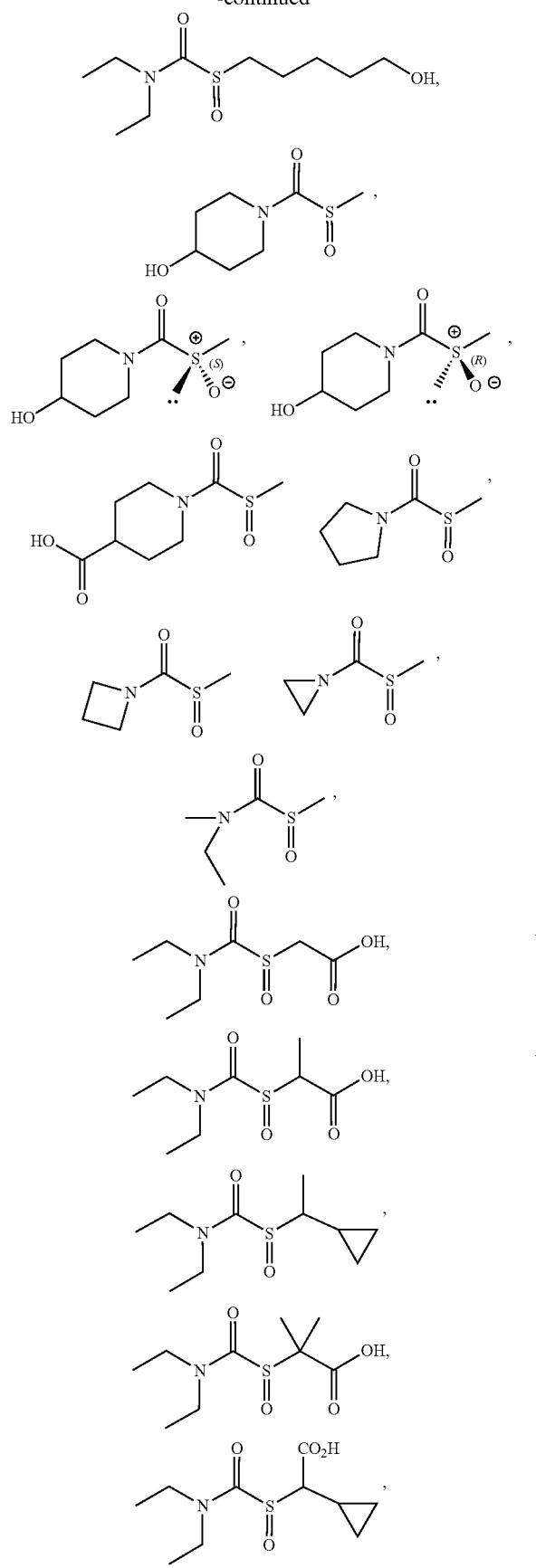
34
-continued
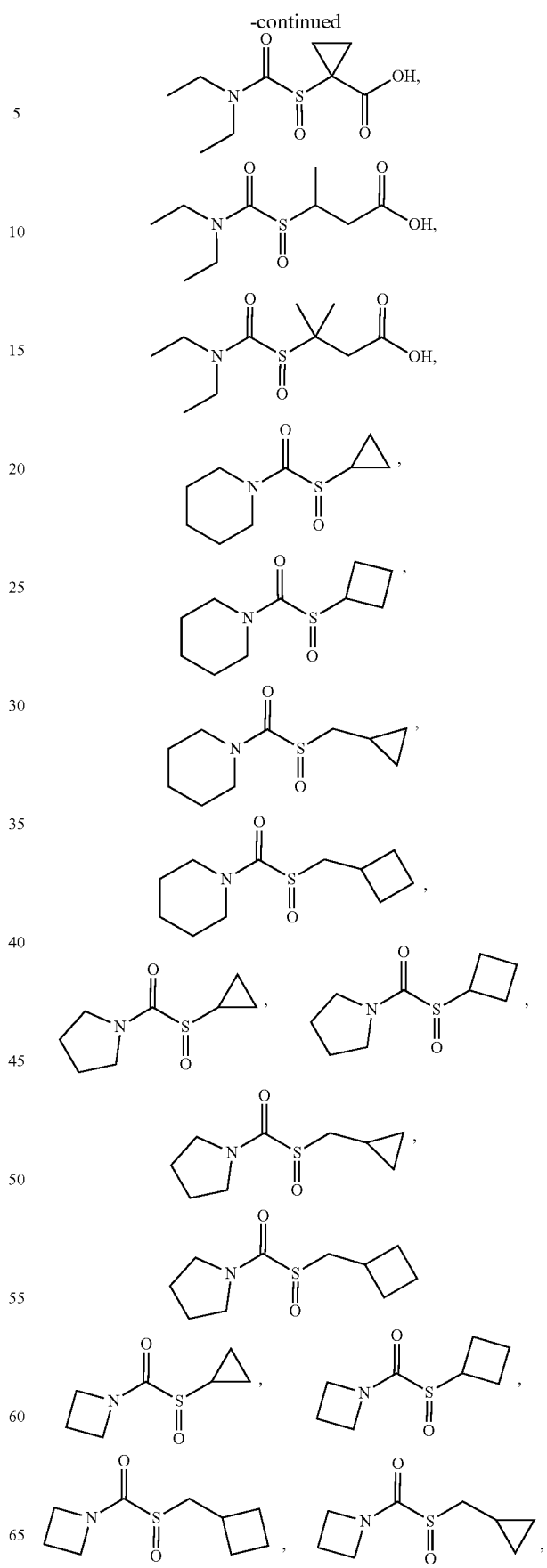

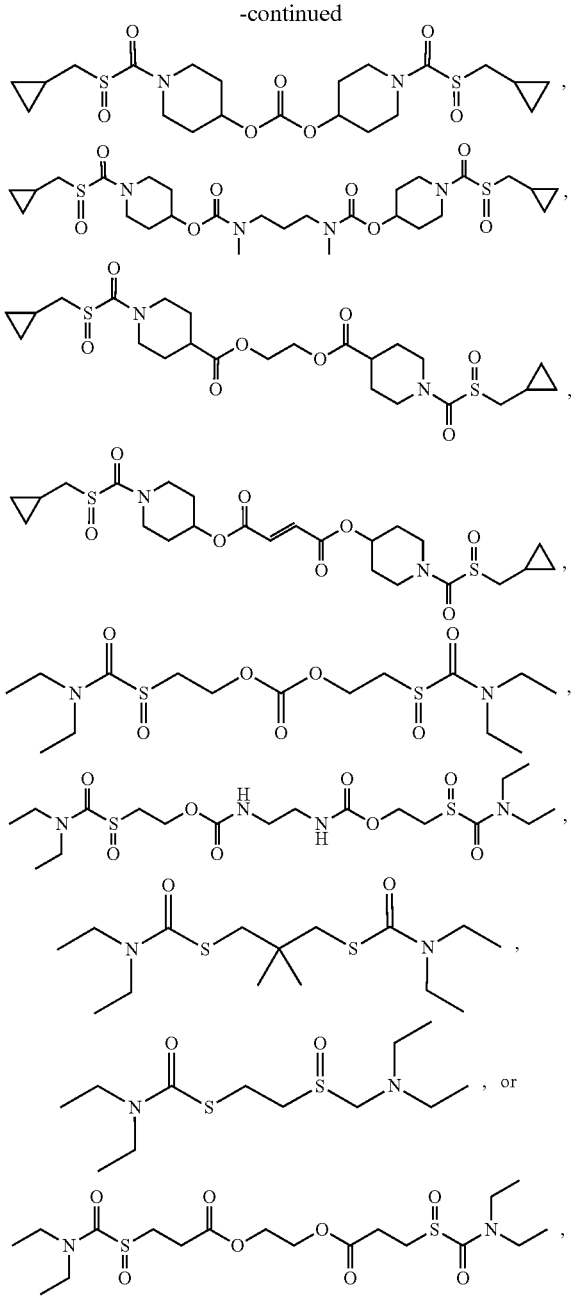

or a pharmaceutically acceptable salt or solvates thereof.

In some embodiments, pharmaceutical compositions comprising a compound as described herein, or a pharmaceutically acceptable salt or solvate thereof, and optionally a pharmaceutically acceptable excipient.

In some embodiments, the pharmaceutical composition comprises an enantiomeric excess of at least 90% of one enantiomer of the compound, or a pharmaceutically acceptable salt or solvate thereof. In some embodiments, the pharmaceutical composition comprises an enantiomeric excess of at least 95% of one enantiomer of the compound, or a pharmaceutically acceptable salt or solvate thereof. In some embodiments, the pharmaceutical composition comprises an enantiomeric excess of at least 98% of one enantiomer of the compound, or a pharmaceutically acceptable salt or solvate thereof. In some embodiments, the pharmaceutical composition comprises an enantiomeric excess of at least 99% of one enantiomer of the compound, or a pharmaceutically acceptable salt or solvate thereof.

In some embodiments, methods of inhibiting an ALDH2 enzyme comprise contacting the ALDH2 enzyme with an effective amount of a compound as described herein, or a pharmaceutically acceptable salt or solvate thereof, or a pharmaceutical composition as described herein.

In some embodiments, methods of treating or preventing an alcohol related disorder in a subject or a subject in need thereof comprising administering to the subject, a compound as described herein, or a pharmaceutically acceptable salt or solvate thereof, or a pharmaceutical composition as described herein. In some embodiments, the alcohol related disorder is alcohol use disorder, alcohol induced disorder, alcohol abuse, alcohol dependence, alcohol intoxication, alcohol withdrawal, or any combination thereof. In some embodiments, methods of treating an alcohol related disorder in a subject or a subject in need thereof comprising administering to the subject, a compound as described herein, or a pharmaceutically acceptable salt or solvate thereof, or a pharmaceutical composition as described herein. In some embodiments, the alcohol related disorder is alcohol use disorder, alcohol induced disorder, alcohol abuse, alcohol dependence, alcohol intoxication, alcohol withdrawal, or any combination thereof. In some embodiments, methods of preventing an alcohol related disorder in a subject or a subject in need thereof comprising administering to the subject, a compound as described herein, or a pharmaceutically acceptable salt or solvate thereof, or a pharmaceutical composition as described herein. In some embodiments, the alcohol related disorder is alcohol use disorder, alcohol induced disorder, alcohol abuse, alcohol dependence, alcohol intoxication, alcohol withdrawal, or any combination thereof.

In some embodiments, methods of treating or preventing alcohol use disorder in a subject or a subject in need thereof comprising administering to the subject, a compound as described herein, or a pharmaceutically acceptable salt or solvate thereof. In some embodiments, methods of treating alcohol use disorder in a subject or a subject in need thereof comprising administering to the subject, a compound as described herein, or a pharmaceutically acceptable salt or solvate thereof. In some embodiments, methods of preventing alcohol use disorder in a subject or a subject in need thereof comprising administering to the subject, a compound as described herein, or a pharmaceutically acceptable salt or solvate thereof.

In some embodiments, methods of reducing the amount of alcohol consumed are provided by a subject is provided. In some embodiments, the subject is diagnosed with, suffers from, or is suspected of having an alcohol-related disorder, such as alcohol use disorder. In some embodiments, the method comprises administering a compound as described herein, or a pharmaceutically acceptable salt or solvate thereof, or a pharmaceutical composition as described herein. In some embodiments, the subject is found to drink less or no alcohol over a 90 day period as compared a 90 day period of time prior to being treated with the pharmaceutical composition.

In some embodiments, methods of reducing alcoholic cravings in a subject with alcohol use disorder are provided. In some embodiments, the method comprises administering a compound as described herein, or a pharmaceutically acceptable salt or solvate thereof, or a pharmaceutical composition as described herein. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the compound, or the pharmaceutically acceptable salt or solvate thereof, or the pharmaceutical composition as described herein. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, methods of reducing drinking alcohol are provided. In some embodiments, the method comprises administering a compound as described herein, or a pharmaceutically acceptable salt or solvate thereof, or a pharmaceutical composition as described herein. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, methods of increasing the percentage of no heavy drinking days for a subject with alcohol use disorder are provided. In some embodiments, the method comprises administering a compound as described herein, or a pharmaceutically acceptable salt or solvate thereof, or a pharmaceutical composition as described herein. In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

In some embodiments, compounds as described herein in use for inhibiting an ALDH2 enzyme in a subject, wherein the use comprises administering to the subject an effective amount of the compound as described herein, or a pharmaceutically acceptable salt, a solvate, a pharmaceutical composition, or a prodrug thereof.

In some embodiments, pharmaceutical compositions as described herein in use for inhibiting an ALDH2 enzyme in a subject, wherein the use comprises administering to the subject an effective amount of the pharmaceutical composition as described herein.

In some embodiments, use of compounds as described herein in the manufacture of a formulation inhibiting an ALDH2 enzyme in a subject, wherein the use comprises administering to the subject an effective amount of the compound as described herein, or a pharmaceutically acceptable salt, a solvate, a pharmaceutical composition, or a prodrug thereof.

In some embodiments, use of pharmaceutical compositions as described herein for inhibiting an ALDH2 enzyme in a subject, wherein the use comprises administering to the subject an effective amount of the pharmaceutical composition as described herein.

In some embodiments, compounds as described herein in use for treating or preventing an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, compounds as described herein in use for treating an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, compounds as described herein in use for preventing an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof.

In some embodiments, pharmaceutical compositions as described herein in use for treating or preventing an alcohol related disorder in a subject or a subject in need thereof, wherein the use comprises administering to the subject an effective amount of the pharmaceutical composition as described herein. In some embodiments, pharmaceutical compositions as described herein in use for treating an alcohol related disorder in a subject or a subject in need thereof, wherein the use comprises administering to the subject an effective amount of the pharmaceutical composition as described herein. In some embodiments, pharmaceutical compositions as described herein in use for preventing an alcohol related disorder in a subject or a subject in need thereof, wherein the use comprises administering to the subject an effective amount of the pharmaceutical composition as described herein.

In some embodiments, use of compounds as described herein in the manufacture of a formulation treating or preventing an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, use of compounds as described herein in the manufacture of a formulation treating an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, use of compounds as described herein in the manufacture of a formulation preventing an alcohol related disorder in a subject or a subject in need thereof, wherein the use comprises administering to the subject an effective amount of the compound as described herein, or a pharmaceutically acceptable salt, a solvate, a pharmaceutical composition, or a prodrug thereof.

In some embodiments, use of pharmaceutical compositions as described herein for treating an alcohol related disorder in a subject or a subject in need thereof, wherein the use comprises administering to the subject an effective amount of the pharmaceutical composition as described herein. In some embodiments, the alcohol related disorder is alcohol use disorder, alcohol induced disorder, alcohol abuse, alcohol dependence, alcohol intoxication, alcohol withdrawal, or any combination thereof.

In some embodiments, compounds as described herein in use for treating or preventing alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, compounds as described herein in use for treating alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, compounds as described herein in use for preventing alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof.

In some embodiments, pharmaceutical compositions as described herein in use for treating or preventing alcohol use disorder in a subject or a subject in need thereof, wherein the use comprises administering to the subject an effective amount of the pharmaceutical composition as described herein. In some embodiments, pharmaceutical compositions as described herein in use for treating alcohol use disorder in a subject or a subject in need thereof, wherein the use comprises administering to the subject an effective amount of the pharmaceutical composition as described herein. In some embodiments, pharmaceutical compositions as described herein in use for preventing alcohol use disorder in a subject or a subject in need thereof, wherein the use comprises administering to the subject an effective amount of the pharmaceutical composition as described herein.

In some embodiments, use of compounds as described herein in the manufacture of a formulation treating or preventing alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, use of compounds as described herein in the manufacture of a formulation treating alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof. In some embodiments, use of compounds as described herein in the manufacture of a formulation preventing alcohol use disorder in a subject or a subject in need thereof, wherein the use comprises administering to the subject an effective amount of the compound as described herein, or a pharmaceutically acceptable salt, a solvate, a pharmaceutical composition, or a prodrug thereof.

In some embodiments, use of pharmaceutical compositions as described herein for treating or preventing alcohol use disorder in a subject or a subject in need thereof, wherein the use comprises administering to the subject an effective amount of the pharmaceutical composition as described herein. In some embodiments, use of pharmaceutical compositions as described herein for treating alcohol use disorder in a subject or a subject in need thereof, wherein the use comprises administering to the subject an effective amount of the pharmaceutical composition as described herein. In some embodiments, use of pharmaceutical compositions as described herein for preventing alcohol use disorder in a subject or a subject in need thereof, wherein the use comprises administering to the subject an effective amount of the pharmaceutical composition as described herein.

In some embodiments, compounds as described herein in use for reducing the amount of alcohol consumed by a subject. In some embodiments, the use comprises administering to the subject an effective amount of the compound as described herein, or a pharmaceutically acceptable salt, a solvate, a pharmaceutical composition, or a prodrug thereof. In some embodiments, the subject is found to drink less or no alcohol over a 90 day period as compared a 90 day period of time prior to being treated with the compound.

In some embodiments, pharmaceutical compositions as described herein in use for reducing the amount of alcohol consumed by a subject. In some embodiments, the use comprises administering to the subject an effective amount of the pharmaceutical composition as described herein. In some embodiments, the subject is found to drink less or no alcohol over a 90 day period as compared a 90 day period of time prior to being treated with the pharmaceutical composition.

In some embodiments, use of compounds as described herein in the manufacture of a formulation reducing the amount of alcohol consumed by a subject. In some embodiments, the use comprises administering to the subject an effective amount of the compound as described herein, or a pharmaceutically acceptable salt, a solvate, a pharmaceutical composition, or a prodrug thereof. In some embodiments, the subject is found to drink less or no alcohol over a 90 day period as compared a 90 day period of time prior to being treated with the compound.

In some embodiments, use of pharmaceutical compositions as described herein for reducing the amount of alcohol consumed by a subject. In some embodiments, the use comprises administering to the subject an effective amount of the pharmaceutical composition as described herein. In some embodiments, the subject is found to drink less or no alcohol over a 90 day period as compared a 90 day period of time prior to being treated with the pharmaceutical composition.

In some embodiments, compounds as described herein in use for reducing alcoholic cravings in a subject. In some embodiments, the use comprises administering to the subject an effective amount of the compound as described herein, or a pharmaceutically acceptable salt, a solvate, a pharmaceutical composition, or a prodrug thereof. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the compound, or the pharmaceutically acceptable salt or solvate thereof, or the pharmaceutical composition as described herein. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, pharmaceutical compositions as described herein in use for reducing alcoholic cravings in a subject. In some embodiments, the use comprises administering the pharmaceutical composition as described herein. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the compound, or the pharmaceutically acceptable salt or solvate thereof, or the pharmaceutical composition as described herein. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, use of compounds as described herein in the manufacture of a formulation reducing alcoholic cravings in a subject. In some embodiments, the use comprises administering a compound as described herein, or a pharmaceutically acceptable salt or solvate thereof, or a pharmaceutical composition as described herein. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the compound, or the pharmaceutically acceptable salt or solvate thereof, or the pharmaceutical composition as described herein. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, use of pharmaceutical compositions as described herein for reducing alcoholic cravings in a subject. In some embodiments, the use comprises administering the pharmaceutical composition as described herein. In some embodiments, the subject is found to have a reduction in cravings as measured on the Visual Analogue Scale of Craving. The Visual Analogue Scale of Craving has 4 questions to assess domains of alcohol craving: the intention to drink, loss of control, relief craving, and urge intensity with a 0-20 point visual analog scale for each item, with 0 indicating no craving and 20 indicating severe craving. In some embodiments, the subject has a reduction in the craving scale after 2 weeks of being treated with the compound, or the pharmaceutically acceptable salt or solvate thereof, or the pharmaceutical composition as described herein. In some embodiments, the reductions in craving occur after 3, 4, 5, 6, 7, 8, 9, 10, 11, 12, or 13 weeks. In some embodiments, the reduction on the scale is about, or at least, 5, 10, 15, 20, 30, 40, 50, 60, 70, or 75 points.

In some embodiments, compounds as described herein in use for reducing drinking alcohol. In some embodiments, the use comprises administering to the subject an effective amount of the compound as described herein, or a pharmaceutically acceptable salt, a solvate, a pharmaceutical composition, or a prodrug thereof. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, pharmaceutical compositions as described herein in use for reducing drinking alcohol. In some embodiments, the use comprises administering to the subject an effective amount of the pharmaceutical composition as described herein. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, use of compounds as described herein in the manufacture of a formulation reducing drinking alcohol. In some embodiments, the use comprises administering to the subject an effective amount of the compound as described herein, or a pharmaceutically acceptable salt, a solvate, a pharmaceutical composition, or a prodrug thereof. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, use of pharmaceutical compositions as described herein for reducing drinking alcohol. In some embodiments, the use comprises administering to the subject an effective amount of the pharmaceutical composition as described herein. In some embodiments, the reduction of consuming alcohol is provided, wherein the number of drinks consumed in a natural environment over a period of time is measured and compared to the same period of time during treatment. In some embodiments, the period of time is 1-14 days before and after treatment is provided. In some embodiments, the information is obtained during a timeline follow-back interview.

In some embodiments, compounds as described herein in use for increasing the percentage of no heavy drinking days for a subject with alcohol use disorder. In some embodiments, the use comprises administering to the subject an effective amount of the compound as described herein, or a pharmaceutically acceptable salt, a solvate, a pharmaceutical composition, or a prodrug thereof. In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

In some embodiments, pharmaceutical compositions as described herein in use for increasing the percentage of no heavy drinking days for a subject with alcohol use disorder. In some embodiments, the use comprises administering the pharmaceutical composition as described herein.

In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

In some embodiments, use of compounds as described herein in the manufacture of a formulation increasing the percentage of no heavy drinking days for a subject with alcohol use disorder. In some embodiments, the use comprises administering to the subject an effective amount of the compound as described herein, or a pharmaceutically acceptable salt, a solvate, a pharmaceutical composition, or a prodrug thereof. In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

In some embodiments, use of pharmaceutical compositions as described herein for increasing the percentage of no heavy drinking days for a subject with alcohol use disorder. In some embodiments, the use comprises administering to the subject an effective amount of the pharmaceutical composition as described herein. In some embodiments, the percentage of no heavy drinking days is increased by at least, or about, 5, 10, 15, 20, 30, 40, 50, 60 70, 80, 90, 100, 200, or 300%. In some embodiments, the time period measured is 1, 2, 3, 4, 5, 6, 7, 8, 9, 10, 11, 12, 13, or more weeks. In some embodiments, the period of time is 26 or more weeks. As used herein, the term "heavy drinking day" is defined as more than 3 drinks per day for women and more than 4 drinks per day for men.

It will be apparent that the compounds provided herein, including all subgenera described herein, may have multiple stereogenic centers. As a result, there exist multiple stereoisomers (enantiomers and diastereomers) of the compounds of the various formula provided herein (and subgenera provided herein). The present disclosure contemplates and encompasses each stereoisomer of any compound of any formula provided herein (and subgenera provided herein), as well as mixtures of said stereoisomers. All enantiomers, diastereomers, and mixtures thereof, are included within the scope of compounds described herein.

Pharmaceutically acceptable salts and solvates of the compounds of any formula provided herein (including all subgenera provided herein) are also within the scope of the disclosure. Isotopic variants of the compounds of any formula provided herein (including all subgenera provided herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds and other agent(s) may be mixed into a preparation or both components may be formulated into separate preparations to use them in combination separately or at the same time.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds is in the range of 0.0001-10 g, 0.0005-9 g, 0.001-8 g, 0.005-7 g, 0.01-6 g, 0.05-5 g, 0.1-4 g, 0.5-4 g, or 1-3 g.

In some embodiments, a pharmaceutical composition comprising the R enantiomer is free or substantially free of the S enantiomer.

In some embodiments, a pharmaceutical composition comprising the S enantiomer is free or substantially free of the R enantiomer.

In some embodiments, a pharmaceutical composition comprises an enantiomeric excess of at least, or about, 80, 85, 90, 91, 92, 93, 94, 95, 96, 97, 98, 99% of a specific enantiomer of a compound provided herein, such as the R or the S enantiomer. In some embodiments, the enantiomeric excess is at least, or about 90%. In some embodiments, the enantiomeric excess is at least, or about 95%. In some embodiments, the enantiomeric excess is at least, or about 98%. In some embodiments, the enantiomeric excess is at least, or about 99%.

The compounds can be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition can contain an active ingredient (i.e., a compound of the disclosure) provided for herein or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, pharmaceutical compositions for oral administration are provided that contain a compound provided herein, and a pharmaceutical excipient suitable for oral administration.

In some embodiments, embodiments provide a solid pharmaceutical composition for oral administration containing: (i) an amount (e.g., effective amount) of a compound; optionally (ii) an amount of a second agent; and (iii) a pharmaceutical excipient suitable for oral administration. In some embodiments, the composition further contains: (iv) an amount of a third agent.

In some embodiments, the pharmaceutical composition may be a liquid pharmaceutical composition suitable for oral consumption. Pharmaceutical compositions suitable for oral administration can be presented as discrete dosage forms, such as, but not limited to, capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as, but not limited to, powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

Embodiments provided for herein further encompass anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. Pharmaceutical compositions and dosage forms that contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, but not limited to, water, glycols, oils, alcohols, flavoring agents, preservatives, coloring agents, and the like in the case of oral liquid preparations (such as, but not limited to, suspensions, solutions, and elixirs) or aerosols; or carriers such as, but not limited to, starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as, but not limited to, acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrose, kaolin, mannitol, silicic acid, sorbitol, starch, pre-gelatinized starch, and mixtures thereof.

Disintegrants may be used in the compositions provided for herein to provide tablets that disintegrate when exposed to an aqueous environment. Too much of a disintegrant may produce tablets, which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as, but not limited to, glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants that can be used to form pharmaceutical compositions and dosage forms include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic and have greater solubility in oils, while surfactants with higher HLB values are more hydrophilic and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof, carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof, carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as, but not limited to, polyethylene glycol alkyl ethers; polyoxyalkylene alkylphenols such as, but not limited to, polyethylene glycol alkyl phenols; polyoxyalkylene alkyl phenol fatty acid esters such as, but not limited to, polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as, but not limited to, polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof, polyoxyethylated vitamins and derivatives thereof, polyoxyethylene-polyoxypropylene block copolymers; and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In some embodiments, the composition may include a solubilizer to ensure good solubilization and/or dissolution of the compound(s) and to minimize precipitation of the compound(s). This can be used, for example, for compositions for non-oral use, e.g., compositions for injection. A solubilizer may also be added to increase the solubility of the hydrophilic drug and/or other components, such as, but not limited to, surfactants, or to maintain the composition as a stable or homogeneous solution or dispersion.

Examples of suitable solubilizers include, but are not limited to, the following: alcohols and polyols, such as, but not limited to, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as, but not limited to, tetrahydrofurfuryl alcohol PEG ether (glycofurol) or methoxy PEG; amides and other nitrogen-containing compounds such as, but not limited to, 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as, but not limited to, ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as, but not limited to, dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, the solubilizers that can be used include sorbitol, glycerol, triacetin, ethyl alcohol, PEG-400, glycofurol and/or propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject or a subject in need thereof using conventional techniques, such as, but not limited to, distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as, but not limited to, 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as, but not limited to, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as, but not limited to, sodium phosphate, disodium hydrogen phosphate, and sodium dihydrogen phosphate can also be used. When the base is a salt, the cation can be any convenient and pharmaceutically acceptable cation, such as, but not limited to, ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, pharmaceutical compositions for injection are provided containing a compound and a pharmaceutical excipient suitable for injection. Components and amounts of agents in the compositions are as described herein.

The forms in which the compositions may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as, but not limited to, lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound(s) in an amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques, which yield a powder of the active ingredient plus any additional desired ingredient from a previously sterile-filtered solution thereof.

Pharmaceutical Compositions for Topical (e.g., Transdermal) Delivery.

In some embodiments, pharmaceutical compositions for transdermal delivery are provided containing a compound(s) and a pharmaceutical excipient suitable for transdermal delivery.

Compositions can be formulated into preparations in solid, semisolid, or liquid forms suitable for local or topical administration, such as, but not limited to, gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as, but not limited to, polyethylene glycols.

Another exemplary formulation for use in the methods employs transdermal delivery devices ("patches"). Such transdermal patches may be used to provide a continuous or discontinuous infusion of a compound in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In some embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, such as orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical compositions can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, about 1 to about 35 mg/kg/day, in single or divided doses. For a 70 kg human, this would amount to about 0.05 to 7 g/day, or about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound is administered in a single dose.

Typically, such administration can be by injection, e.g., intravenous injection, in order to introduce the agent quickly. However, other routes, such as oral, may be used as appropriate. A single dose of a compound may also be used for treatment of an acute condition.

In some embodiments, a compound is administered in multiple doses. Dosing may be about once, twice, three times, four times, five times, six times, or more than six times per day. Dosing may be about once a month, once every two weeks, once a week, or once every other day. In some embodiments, a compound and another agent are administered together about once per day to about 6 times per day. In some embodiments, the administration of a compound and an agent continues for less than about 7 days. In yet another embodiment, the administration continues for more than about 6, 10, 14, 28 days, two months, six months, or one year. In some cases, continuous dosing is achieved and maintained as long as necessary.

Administration of the compounds may continue as long as necessary. In some embodiments, a compound is administered for more than 1, 2, 3, 4, 5, 6, 7, 14, or 28 days. In some embodiments, a compound is administered for less than 28, 14, 7, 6, 5, 4, 3, 2, or 1 day. In some embodiments, a compound is administered chronically on an ongoing basis, e.g., for the treatment of chronic effects.

A compound may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds may slow or inhibit the migration and proliferation of smooth muscle cells in the arterial wall, which contribute to restenosis. A compound may be administered, for example, by local delivery from the struts of a stent, from a stent graft, from grafts, or from the cover or sheath of a stent. In some embodiments, a compound is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds may be applied to the surface of the stent by various methods such as, but not limited to, dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example, in microchannels or micropores. When implanted, the compound diffuses out of the body of the stent to contact the arterial wall. Such stents may be prepared by dipping a stent manufactured to contain such micropores or microchannels into a solution of the compound in a suitable solvent, followed by evaporation of the solvent. Excess drug on the surface of the stent may be removed via an additional brief solvent wash. In yet other embodiments, compounds may be covalently linked to a stent or graft. A covalent linker may be used which degrades in vivo, leading to the release of the compound. Any bio-labile linkage may be used for such a purpose, such as, but not limited to, ester, amide or anhydride linkages. Compounds may additionally be administered intravascularly from a balloon used during angioplasty. Extravascular administration of the compounds via the pericardial or via adventitial application of formulations may also be performed to decrease restenosis.

A variety of stent devices, which may be used as described, are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds may be administered in dosages. It is known in the art that due to intersubject variability in compound pharmacokinetics, individualization of dosing regimen is necessary for optimal therapy. Dosing for a compound may be found by routine experimentation in light of the instant disclosure.

When a compound is administered in a composition that comprises one or more agents, which has a shorter half-life than the compound unit dose forms of the agent and the compound may be adjusted accordingly.

The subject pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can include a conventional pharmaceutical carrier or excipient and a compound as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Methods of Use

In some embodiments, the method comprises administering to a subject or a subject in need thereof an amount, such as a therapeutically effective amount, of a compound, or a pharmaceutically acceptable salt or solvate thereof. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half-maximal inhibitory concentration of an inhibitor in inhibiting biological or biochemical function. This quantitative measure indicates how much of a particular inhibitor is needed to inhibit a given biological process (or component of a process, i.e., an enzyme, cell, cell receptor or microorganism) by half. In other words, it is the half-maximal (50%) inhibitory concentration (IC) of a substance (50% IC, or IC50). EC50 refers to the plasma concentration required for obtaining 50%> of a maximum effect in vivo.

In some embodiments, the subject methods utilize an ALDH2 inhibitor with an IC50 value of about or less than a predetermined value, as ascertained in an in vitro assay. In some embodiments, the ALDH2 inhibitor inhibits ALDH2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 M or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 PM, 100 PM, 200 M, 300 µM, 400 µM, or 500 µM, or less, (or a number in the range defined by and including any two numbers above).

In some embodiments, the subject method of inhibiting ALDH2 enzyme comprises contacting the ALDH2 enzyme with an effective amount of a compound or a pharmaceutically acceptable salt or solvate thereof as described herein.

In some embodiments, compounds described herein are in use for inhibiting an ALDH2 enzyme in a subject, wherein the use comprises administering to the subject an effective amount of one or more compounds as described herein, pharmaceutically acceptable salts, solvates, pharmaceutical compositions, or prodrugs thereof.

In some embodiments, are provided pharmaceutical compositions as described herein are in use for inhibiting an ALDH2 enzyme in a subject, wherein the use comprises administering to the subject an effective amount of one or more pharmaceutical compositions as described In some embodiments, are provided uses of compounds as described herein in the manufacture of a formulation inhibiting an ALDH2 enzyme in a subject, wherein the use comprises administering to the subject an effective amount of one or more compounds as described herein, pharmaceutically acceptable salts, solvates, pharmaceutical compositions, or prodrugs thereof.

In some embodiments, are provided uses of a pharmaceutical composition as described herein for inhibiting an ALDH2 enzyme in a subject, wherein the use comprises administering to the subject an effective amount of one or more pharmaceutical compositions as described herein.

The subject methods are useful for treating or preventing a disease or disorder condition associated with ALDH2. Any disease or disorder condition that results directly or indirectly from an abnormal activity or expression level of ALDH2 can be an intended disease or disorder condition.

In some embodiments, the said method for treating or preventing disease or disorder condition associated with ALDH2 in a subject or a subject in need thereof comprises administering to the subject, a compound or a pharmaceutically acceptable salt or solvate thereof as described herein.

In some embodiments, are provided Compounds as described herein in use for treating or preventing a disease or disorder associated with aberrant ALDH2 activity in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided uses of compounds as described herein in the manufacture of a formulation treating or preventing a disease or disorder associated with aberrant ALDH2 activity in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided compounds as described herein in use for treating or preventing an alcohol related disorder in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided pharmaceutical compositions as described herein in use for treating or preventing an alcohol related disorder in a subject or a subject in need thereof, wherein the use comprises administering to the subject an effective amount of one or more pharmaceutical compositions as described herein.

In some embodiments, are provided uses of compounds as described herein in the manufacture of a formulation treating or preventing an alcohol related disorder in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided uses of pharmaceutical compositions as described herein for treating or preventing an alcohol related disorder in a subject or a subject in need thereof, wherein the use comprises administering to the subject an effective amount of one or more pharmaceutical compositions as described herein. In some embodiments, are provided uses of pharmaceutical compositions as described herein for treating an alcohol related disorder in a subject or a subject in need thereof, wherein the use comprises administering to the subject an effective amount of one or more pharmaceutical compositions as described herein. In some embodiments, are provided uses of pharmaceutical compositions as described herein for preventing an alcohol related disorder in a subject or a subject in need thereof, wherein the use comprises administering to the subject an effective amount of one or more pharmaceutical compositions as described herein. In some embodiments, the alcohol related disorder is alcohol use disorder, alcohol induced disorder, alcohol abuse, alcohol dependence, alcohol intoxication, alcohol withdrawal, or any combination thereof.

Compounds of the disclosure, as well as pharmaceutical compositions comprising them, can be administered to treat any of the described alcohol related disorder, alone or in combination with a medical therapy.

In other aspects, compounds of the disclosure, as well as pharmaceutical compositions comprising thereof, can be administered to treat any of the described alcohol related disorder, alone or in combination with one or more other agents.

The following examples are illustrative, but not limiting, of the methods and compositions described herein. Other suitable modifications and adaptations of the variety of conditions and parameters normally encountered in therapy, synthesis, and other embodiments disclosed herein are within the spirit and scope of the embodiments.

Compounds provided for herein include, but not limited to, Examples 1-1 to 1-16, 1-2A, 1-2B, 1-4A, 1-4B-, which have been either exemplified or identified in Tables 1.

TABLE 1

| Example | Formula | Name |
| --- | --- | --- |
| 1-1 | [structure] | S-methyl diethylcarbamothioate |
| 1-2 | [structure] | N,N-diethyl-1-(methylsulfinyl)-methanamide |
| 1-2A | [structure] | (S)-N,N-diethyl-1-(methylsulfinyl)-methanamide (Peak-1) |
| 1-2B | [structure] | (R)-N,N-diethyl-1-(methylsulfinyl)-methanamide (Peak-2) |

TABLE 1-continued

| Example | Formula | Name |
|---|---|---|
| 1-3 | 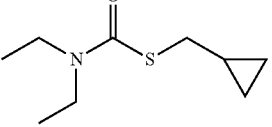 | S-(cyclopropyl-methyl)diethyl-carbamothioate |
| 1-4 | 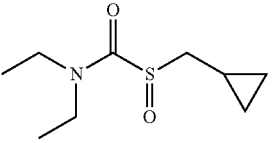 | 1-((cyclopropyl-methyl)sulfinyl)-N,N-diethyl-methanamide |
| 1-4A | 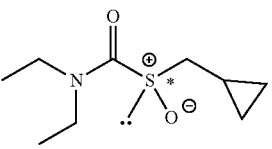 | 1-((cyclopropyl-methyl)sulfinyl)-N,N-diethyl-metanamide (Peak-1) |
| 1-4B | 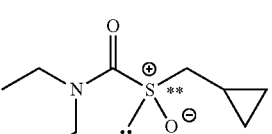 | 1-((cyclopropyl-methyl)sulfinyl)-N,N-diethyl-methanamide (Peak-2) |
| 1-5 | 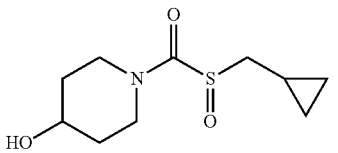 [SMILES: O=C(N1CCC(O)CC1)S(=O)CC1CC1] | ((cyclopropyl-methyl)sulfinyl)(4-hydroxypiperidin-1-yl)methanone |
| 1-6 | 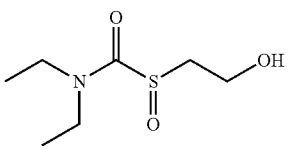 | N,N-diethyl-1-((2-hydroxyethyl)-sulfinyl)methan-amide |
| 1-7 | 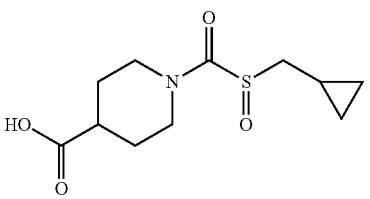 [SMILES: O=C(O)C1CCN(C(=O)S(=O)CC2CC2)CC1] | 1-(((cyclopropyl-methyl)sulfinyl)-carbonyl)piperi-dine-4-carboxylic acid |
| 1-8 | 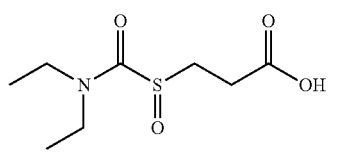 | 3-((diethylcar-bamoyl)sulfinyl)-propanoic acid |
| 1-9 | 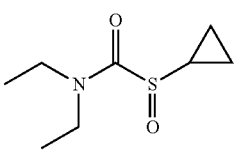 | 1-(cyclopropyl-sulfinyl)-N,N-diethylmethan-amide |

TABLE 1-continued

| Example | Formula | Name |
|---|---|---|
| 1-10 | | N,N-diethyl-1-((oxetan-3-yl-methyl)sulfinyl)-methanamide |
| 1-11 | | (4-hydroxypiperidin-1-yl)(methylsulfinyl)methanone |
| 1-11A | | (R)-(4-hydroxy-piperidin-1-yl)-(methylsulfinyl)-methanone |
| 1-11B | | (S)-(4-hydroxy-piperidin-1-yl)-(methylsulfinyl)-methanone |
| 1-12 | | 2-((diethylcarbamoyl)sulfinyl)-acetic acid |
| 1-13 | | N-ethyl-N-methyl-1-(methylsulfinyl)-methanamide |
| 1-14 | | azetidin-1-yl-(methylsulfinyl)-methanone |
| 1-15 | | 1,1'-(ethane-1,2-diyldisulfinyl)bis-(N,N-diethyl-methanamide |
| 1-16 | | 1,1'-2,2-dimethyl-propane-1,3-diyldisulfinyl)bis(N,N-diethylmethanamide |

Synthesis

Compounds of the disclosure, including salts thereof, can be prepared using known organic synthesis techniques and can be synthesized according to any of numerous possible synthetic routes.

The reactions for preparing compounds of the disclosure can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures, which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography ("HPLC") or thin layer chromatography.

The expressions, "ambient temperature," "room temperature" "RT," and "r.t." as used herein, are understood in the art, and refer generally to a temperature, e.g. a reaction temperature, that is about the temperature of the room in which the reaction is carried out, for example, a temperature from about 20° C. to about 30° C.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

In some embodiments, the following embodiments are provided:

1. A compound having Formula (I), Formula (I-a), Formula (I-b), or Formula (III), or a pharmaceutically acceptable salt or solvate thereof:

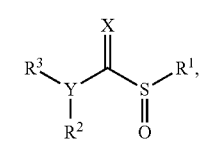
Formula (I)

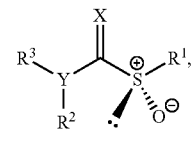
Formula (I-a)

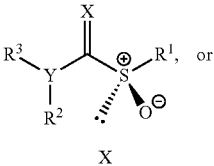
Formula (I-b)

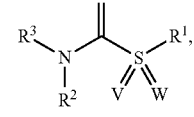
Formula (III)

wherein:

X is O, S, or N—$R^4$;

Y is N or C—$R^5$;

V is absent or O;

W is absent or O;

$R^1$, $R^2$, $R^3$, $R^4$, and $R^5$ are each independently H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$ NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$;

wherein when $R^1$, $R^2$, $R^3$, $R^4$, or $R^5$ is alkyl, alkoxy, alkenyl, alkynyl, haloalkyl, haloalkoxy, aryl, cycloalkyl, heteroaryl, heterocycloalkyl, then $R^1$, $R^2$, $R^3$, $R^4$, or $R^5$ is optionally substituted with at least one $R^b$ substituent;

or $R^2$ and $R^3$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents;

or when Y is C—$R^5$, $R^2$ and $R^5$ together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents;

or when Y is C—$R^5$, $R^3$ and $R^5$, together with the atoms to which they are attached, form a 3-, 4-, 5-, 6-, or 7-membered cycloalkyl or heterocycloalkyl ring optionally substituted with 1, 2, 3, 4 or 5 independently selected $R^b$ substituents;

each $R^a$ is independently selected from H, D, C$_{1-6}$ alkyl, C$_{1-4}$haloalkyl, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$alkyl, C$_{3-10}$ cycloalkyl-C$_{1-4}$ alkyl, (5-10 membered heteroaryl)-C$_{1-4}$ alkyl, and (4-14 membered heterocycloalkyl)-C$_{1-4}$ alkyl;

wherein when R$^a$ is C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$cycloalkyl-C$_{1-4}$ alkyl, (5-10 membered heteroaryl)-C$_{1-4}$ alkyl- or (4-14 membered heterocycloalkyl)-C$_{1-4}$ alkyl, then R$^a$ is optionally substituted with 1, 2, 3, 4, or 5 independently selected R$^d$ substituents;

each $R^b$ substituent is independently selected from a bond, H, D, halo, oxo, C$_{1-10}$ alkyl, C$_{1-6}$ alkoxy, C$_{1-4}$ haloalkyl, C$_{1-4}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, (4-14 membered heterocycloalkyl)-C$_{1-4}$ alkyl, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$), NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)(=NR$^c$)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$;

wherein when $R^b$ is C$_{1-10}$ alkyl, C$_{1-6}$ alkoxy, C$_{1-4}$haloalkyl, C$_{1-4}$ haloalkoxy, C$_{6-10}$ aryl, C$_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents;

each $R^c$ is independently selected from H, D, OH, $C_{1-6}$ alkyl, $C_{1-6}$ alkoxy, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl;

wherein when $R^c$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^c$ is optionally substituted with 1, 2, 3, 4, or 5 independently selected $R^f$ substituents; each $R^f$ is independently selected from halogen, $C_{1-10}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$ C(=NR$^g$)NR$^g$R$^g$, NR$^g$ C(=NOH)NR$^g$R$^g$, NR$^g$C(=NCN)NR$^g$R$^g$, SF$_5$, P(O)R$^g$R$^g$, P(O)(OR$^g$)(OR$^g$), S(O)R$^g$, S(O)NR$^g$R$^g$, S(O)$_2$R$^g$, NR$^g$S(O)$_2$R$^g$, NR$^g$ S(O)$_2$NR$^g$R$^g$, and S(O)$_2$NR$^g$R$^g$;

wherein when $R^f$ is $C_{1-4}$alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R''$ substituents;

each $R''$ is independently selected from $C_{1-10}$ alkyl, $C_{1-4}$ haloalkyl, halo, CN, R$^o$, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, NR$^o$C(=NOH)NR$^o$R$^o$, NR$^o$C(=NCN)NR$^o$R$^o$, SF$_5$, P(O)R$^o$R$^o$, P(O)(OR$^o$)(OR$^o$), S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$;

each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^O$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, SF$_5$, P(O)R$^e$R$^e$, P(O)(OR$^e$)(OR$^e$), S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$, wherein when $R^d$ is $C_{1-6}$alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected R substituents;

each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents;

each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected R substituents;

each $R^P$ is independently selected from $C_{1-10}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$ NR$^r$C(O)OR$^r$, C(=NR$^r$)NR$^r$, NR$^r$C(=NR$^r$)NR$^r$R$^r$, NR$^r$C(=NOH)NR$^r$R$^r$, NR$^r$C(=NCN)NR$^r$R$^r$, SF$_5$, P(O)R$^r$R$^r$, P(O)(OR$^r$)(OR$^r$), S(O)R$^r$, S(O)NR$^r$R$^r$, S(O)$_2$R$^r$, NR$^r$S(O)$_2$R$^r$, NR$^r$S(O)$_2$NR$^r$R$^r$, and S(O)$_2$NR$^r$R$^r$;

each $R^o$ or $R^r$ is independently selected from H, D, $C_{1-10}$ alkyl, $C_{3-6}$cycloalkyl, $C_{6-10}$ aryl, 5 or 6-membered heteroaryl, $C_{1-4}$ haloalkyl, $C_{2-4}$alkenyl, and $C_{2-4}$ alkynyl, wherein when $R^o$ or $R^r$ is $C_{1-10}$ alkyl, $C_{3-6}$ cycloalkyl, $C_{6-10}$ aryl, 5 or 6-membered heteroaryl, $C_{2-4}$ alkenyl, and $C_{2-4}$ alkynyl, then $R^o$ or $R^r$ is optionally substituted with 1, 2 or 3 independently selected $R^q$ substituents;

each $R^q$ is independently selected from D, OH, CN, —COOH, NH$_2$, halo, $C_{1-6}$alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —CONHR$^{12}$, —NHC(O)R$^{12}$, —OC(O)R$^{12}$, —C(O)OR$^{12}$, —C(O)R$^{12}$, —SO$_2$R$^{12}$, —NHSO$_2$R$^{12}$, —SO$_2$NHR$^{12}$ and NR$^{12}$R$^{12}$, wherein when $R^q$ is $C_{1-6}$ alkyl, phenyl, 4-6 membered heterocycloalkyl or 5-6 membered heteroaryl, then $R^q$ is optionally substituted with OH, CN, —COOH, NH$_2$, $C_{1-6}$ alkoxy, $C_{3-6}$cycloalkyl or 4-6 membered heterocycloalkyl; and each $R^{12}$ is independently $C_{1-6}$ alkyl.

2. A compound having Formula (I), Formula (I-a), Formula (I-b), or Formula (III), or a pharmaceutically acceptable salt or solvate thereof:

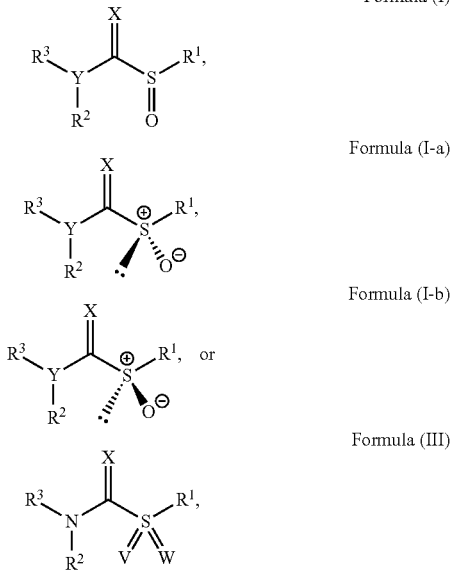

Formula (I)

Formula (I-a)

Formula (I-b)

Formula (III)

wherein:
X is O, S or N—R$^4$;
Y is N or C—R$^5$;
V is absent or O;
W is absent or O;
R$^1$, R$^2$, R$^3$, R$^4$, and R$^5$ are each independently H, D, halo, oxo, C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$alkyl, (5-14 membered heteroaryl)-C$_{1-4}$ alkyl, (4-14 membered heterocycloalkyl)-C$_{1-4}$ alkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$ NR$^a$R$^a$, NR$^a$C(O)R$^a$, NR$^a$C(O)OR$^a$, NR$^a$(O)NR$^a$R$^a$, C(=NR$^a$)R$^a$, C(=NR$^a$)NR$^a$R$^a$, NR$^a$C=NR$^a$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$;
wherein when R$^1$, R$^2$, R$^3$, R$^4$, or R$^5$ is C$_{1-6}$ alkyl, C$_{1-6}$ alkoxy, C$_{2-6}$alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$alkyl, (5-14 membered heteroaryl)-C$_{1-4}$ alkyl, or (4-14 membered heterocycloalkyl)-C$_{1-4}$ alkyl, then R$^1$, R$^2$, R$^3$, R$^4$, or R$^5$ is optionally substituted with 1, 2, 3, 4 or 5 independently selected R$^b$ substituents;
or R$^2$ and R$^3$, together with the atom to which they are attached, form a 3-, 4-, 5-, 6-, or 7-membered cycloalkyl or heterocycloalkyl ring optionally substituted with 1, 2, 3, 4 or 5 independently selected R$^b$ substituents;
or when Y is C—R$^5$, R$^2$ and R$^5$ together with the atom to which they are attached, form a 3-, 4-, 5-, 6-, or 7-membered cycloalkyl or heterocycloalkyl ring optionally substituted with 1, 2, 3, 4 or 5 independently selected R$^b$ substituents;
or when Y is C—R$^5$, R$^3$ and R$^5$, together with the atoms to which they are attached, form a 3-, 4-, 5-, 6-, or 7-membered cycloalkyl or heterocycloalkyl ring optionally substituted with 1, 2, 3, 4 or 5 independently selected R$^b$ substituents;
each R$^a$ is independently selected from H, D, C$_{1-6}$ alkyl, C$_{1-4}$haloalkyl, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$alkyl, C$_{3-10}$ cycloalkyl-C$_{1-4}$ alkyl, (5-10 membered heteroaryl)-C$_{1-4}$ alkyl, and (4-14 membered heterocycloalkyl)-C$_{1-4}$ alkyl;
wherein when R$^a$ is C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$cycloalkyl-C$_{1-4}$ alkyl, (5-10 membered heteroaryl)-C$_{1-4}$ alkyl- or (4-14 membered heterocycloalkyl)-C$_{1-4}$ alkyl, then R$^a$ is optionally substituted with 1, 2, 3, 4, or 5 independently selected R$^d$ substituents;
each R$^b$ substituent is independently selected from a bond, D, halo, oxo, C$_{1-10}$ alkyl, C$_{1-6}$ alkoxy, C$_{1-4}$ haloalkyl, C$_{1-4}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, (4-14 membered heterocycloalkyl)-C$_{1-4}$ alkyl, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$), NHR$^c$, (=NR$^c$)NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)(=NR$^c$)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$;
wherein when R$^b$ is C$_{1-10}$ alkyl, C$_{1-6}$ alkoxy, C$_{1-4}$haloalkyl, C$_{1-4}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$cycloalkyl-C$_{1-4}$ alkyl, (5-10 membered heteroaryl)-C$_{1-4}$ alkyl- or (4-14 membered heterocycloalkyl)-C$_{1-4}$ alkyl, then R$^b$ is optionally substituted with 1, 2, or 3 independently selected R$^d$ substituents;
each R$^c$ is independently selected from H, D, —OH, C$_{1-6}$ alkyl, C$_{1-6}$ alkoxy, C$_{1-4}$ haloalkyl, C$_{2-6}$alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$alkyl, (5-10 membered heteroaryl)-C$_{1-4}$ alkyl, and (4-10 membered heterocycloalkyl)-C$_{1-4}$ alkyl;
wherein when R$^c$ is C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl- or (4-10 membered heterocycloalkyl)-C$_{1-4}$ alkyl, then R$^c$ is optionally substituted with 1, 2, 3, 4 or 5 independently selected R$^f$ substituents;
each R$^f$ is independently selected from halogen, C$_{1-10}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl, halo, CN, NHOR$^g$, ORB, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)NR$^g$R$^g$, NR$^g$C(O)OR$^g$, C(=NR$^g$)NR$^g$R$^g$, NR$^g$ C(=NR$^g$)NR$^g$R$^g$, NR$^g$ C(=NOH)NR$^g$R$^g$, NR$^g$C(=NCN)NR$^g$R$^g$, SF$_5$, P(O)$R^gR^g$, P(O)(O$R^g$)(O$R^g$), S(O)$R^g$, S(O)N$R^gR^g$, S(O)$_2R^g$, N$R^g$S(O)$_2R^g$, N$R^g$ S(O)$_2$N$R^gR^g$, and S(O)$_2$N$R^gR^g$;

wherein when $R^f$ is $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R^n$ substituents;

each $R^n$ is independently selected from $C_{1-10}$ alkyl, $C_{1-4}$ haloalkyl, halo, CN, $R^o$, NHO$R^o$, O$R^o$, S$R^o$, C(O)$R^o$, C(O)N$R^oR^o$, C(O)O$R^o$, OC(O)$R^o$, OC(O)N$R^oR^o$, NH$R^o$, N$R^oR^o$, $NR^o$C(O)$R^o$, $NR^o$C(O)N$R^oR^o$, $NR^o$C(O)O$R^o$, C(=N$R^o$)N$R^oR^o$, $NR^o$C(=N$R^o$)N$R^oR^o$, $NR^o$C(=NOH)N$R^oR^o$, $NR^o$C(=NCN)N$R^oR^o$, SF$_5$, P(O)$R^oR^o$, P(O)(O$R^o$)(O$R^o$), S(O)$R^o$, S(O)N$R^oR^o$, S(O)$_2R^o$, $NR^o$S(O)$_2R^o$, $NR^o$S(O)$_2$N$R^oR^o$, and S(O)$_2$N$R^oR^o$;

each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, NH$_2$, NHO$R^e$, O$R^e$, S$R^e$, C(O)$R^e$, C(O)N$R^eR^e$, C(O)O$R^e$, OC(O)$R^e$, OC(O)N$R^eR^e$, NH$R^e$, N$R^eR^e$, $NR^e$C(O)$R^e$, $NR^e$C(O)N$R^eR^e$, $NR^e$C(O)O$R^e$, C(=N$R^e$)N$R^eR^e$, $NR^e$C(=N$R^e$)N$R^eR^e$ $NR^e$C(=NOH)N$R^eR^e$, $NR^e$C(=NCN)N$R^eR^e$, SF$_5$, P(O)$R^eR^e$, P(O)(O$R^e$)(O$R^e$), S(O)$R^e$, S(O)N$R^eR^e$, S(O)$^2R^e$, $NR^e$S(O)$_2R^e$, $NR^e$S(O)$_2$N$R^eR^e$, and S(O)$_2$N$R^eR^e$, wherein when $R^d$ is $C_{1-6}$ alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected $R^f$ substituents;

each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents;

each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected R substituents;

each $R^p$ is independently selected from $C_{1-10}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, NHO$R^r$, O$R^r$, S$R^r$, C(O)$R^r$, C(O)N$R'R^r$, C(O)O$R^r$, OC(O)$R^r$, OC(O)N$R'R^r$, NH$R^r$, N$R^c$, $NR'$C(O)$R^r$, $N'R'$C(O)N$R'R^r$, $NR'$C(O)O$R^r$, C(=N$R'$)N$R^c$, $NR'$C(=N$R'$)N$R^r$, $NR'$C(=NOH)N$R^c$, $NR'$C(=NCN)N$R'R^r$ SF$_5$, P(O)$R'R^r$, P(O)(O$R'$)(O$R^r$), S(O)$R^r$, S(O)N$R'R^r$, S(O)$_2R^r$, $NR'$S(O)$_2R^r$, $NR^r$S(O)$_2$N$R'R^r$, and S(O)$_2$N$R'R^r$;

each $R^o$ or $R^r$ is independently selected from H, D, $C_{1-10}$ alkyl, $C_{3-6}$cycloalkyl, $C_{6-10}$ aryl, 5 or 6-membered heteroaryl, $C_{1-4}$ haloalkyl, $C_{2-4}$alkenyl, and $C_{2-4}$ alkynyl, wherein when $R^o$ or $R^r$ is $C_{1-10}$ alkyl, $C_{3-6}$ cycloalkyl, $C_{6-10}$ aryl, 5 or 6-membered heteroaryl, $C_{2-4}$ alkenyl, and $C_{2-4}$ alkynyl, then $R^o$ or $R^r$ is optionally substituted with 1, 2 or 3 independently selected $R^q$ substituents;

each $R^g$ is independently selected from D, OH, CN, —COOH, NH$_2$, halo, $C_{1-6}$alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, —CONH$R^{12}$, —NHC(O)$R^{12}$, —OC(O)$R^{12}$, —C(O)O$R^{12}$, —C(O)$R^{12}$, —SO$_2R^{12}$, —NHSO$_2R^{12}$, —SO$_2$NH$R^{12}$ and $NR^{12}R^{12}$, wherein when $R^j$ is $C_{1-6}$ alkyl, phenyl, 4-6 membered heterocycloalkyl or 5-6 membered heteroaryl, then $R^q$ is optionally substituted with OH, CN, —COOH, NH$_2$, $C_{1-6}$ alkoxy, $C_{3-6}$cycloalkyl or 4-6 membered heterocycloalkyl; and each $R^{12}$ is independently $C_{1-6}$ alkyl.

3. The compound of any one of embodiments 1-2, or a pharmaceutically acceptable salt or solvate thereof, wherein X is O.

4. The compound of any one of embodiments 1-3, or a pharmaceutically acceptable salt or solvate thereof, wherein Y is N 5. The compound of any one of embodiments 1-4, or a pharmaceutically acceptable salt or solvate thereof, wherein $R^2$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, each of which is optionally substituted with 1, 2, 3, 4 or 5 independently selected $R^b$ substituents and $R^b$ is as defined in any one of embodiments 1-2.

6. The compound of any one of embodiments 1-5, or a pharmaceutically acceptable salt or solvate thereof, wherein $R^2$ is $C_{1-6}$ alkyl, which is optionally substituted with 1, 2, 3, 4 or 5 independently selected $R^b$ substituents and $R^b$ is as defined in any one of embodiments 1-2.

7. The compound of any one of embodiments 1-6, or a pharmaceutically acceptable salt or solvate thereof, wherein $R^2$ is ethyl.

8. The compound of any one of embodiments 1-7, or a pharmaceutically acceptable salt or solvate thereof, wherein $R^3$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, each of which is optionally substituted with 1, 2, 3, 4 or 5 independently selected $R^b$ substituents and $R^b$ is as defined in any one of embodiments 1-2.

9. The compound of any one of embodiments 1-8, or a pharmaceutically acceptable salt or solvate thereof, wherein $R^3$ is $C_{1-6}$ alkyl, which is optionally substituted with 1, 2, 3, 4 or 5 independently selected $R^b$ substituents and $R^b$ is as defined in any one of embodiments 1-2.

10. The compound of any one of embodiments 1-9, or a pharmaceutically acceptable salt or solvate thereof, wherein $R^3$ is ethyl.

11. The compound of any one of embodiments 1-4, or a pharmaceutically acceptable salt or solvate thereof, wherein $R^2$ and $R^3$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents, and $R^b$ is as defined in any one of embodiments 1-2.

12. The compound of any one of embodiments 1-4, or a pharmaceutically acceptable salt or solvate thereof, wherein $R^2$ and $R^3$, together with the atom to which they are attached, form a 3-, 4-, 5-, 6-, or 7-membered cycloalkyl ring optionally substituted with 1, 2, 3, 4 or 5 independently selected $R^b$ substituents, and $R^b$ is as defined in any one of embodiments 1-2.

13. The compound of any one of embodiments 1-4, or a pharmaceutically acceptable salt or solvate thereof, wherein $R^2$ and $R^3$, together with the atom to which they are attached, form a 6-membered heterocycloalkyl ring optionally substituted with 1, 2, 3, 4 or 5 independently selected $R^b$ substituents and $R^b$ is as defined in any one of embodiments 1-2.

14. The compound of any one of embodiments 1-4, or a pharmaceutically acceptable salt or solvate thereof, wherein $R^2$ and $R^3$, together with the atom to which they are attached, form a 6-membered heterocycloalkyl ring optionally substituted with 1 $R^b$ substituent and $R^b$ is as defined in any one of embodiments 1-2.

15. The compound of embodiment 14 or a pharmaceutically acceptable salt or solvate thereof, wherein $R^b$ is D, halo, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$ and $R^c$ is as defined in any one of embodiments 1-2.

16. The compound of embodiment 16, or a pharmaceutically acceptable salt or solvate thereof, wherein $R^c$ is H.

17. The compound of embodiment 16, or a pharmaceutically acceptable salt or solvate thereof, wherein $R^b$ is OH or COOH.

18. The compound of any one of embodiments 1-17, or a pharmaceutically acceptable salt or solvate thereof, wherein the compound has a formula of

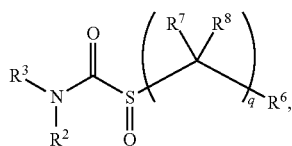

Formula (II)

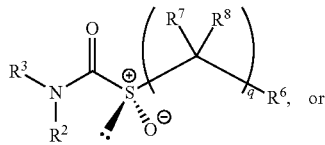

Formula (II-a)

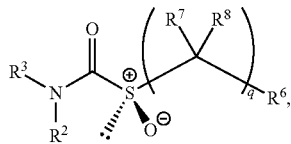

Formula (II-b)

wherein:

q is 0-6;

$R^6$, $R^7$, and $R^8$ are each independently H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, (4-14 membered heterocycloalkyl)-$C_{1-4}$ alkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$ $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$ $S(O)_2R^a$, $SF_5$, $P(O)R^aR^a$, $P(O)(OR^a)(OR^a)$, $B(OR^a)_2$ and $S(O)_2NR^aR^a$;

wherein when $R^6$, $R^7$, or $R^8$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^6$, $R^7$, or $R^8$ is optionally substituted with 1, 2, 3, 4 or 5 independently selected $R^b$ substituents;

or $R^7$ and $R^8$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents; and $R^a$, $R^b$, $R^2$, and $R^3$ are as defined in any one of the embodiments 1-17.

19. The compound of any one of embodiments 1-18, or a pharmaceutically acceptable salt or solvate thereof, wherein $R^7$ and $R^8$ are each independently H, or $C_{1-6}$ alkyl optionally substituted with 1, 2, 3, 4 or 5 independently selected $R^b$ substituents and $R^b$ is as defined in any one of embodiments 1-2.

20. The compound of any one of embodiments 1-19, or a pharmaceutically acceptable salt or solvate thereof, wherein $R^7$ is H.

21. The compound of any one of embodiments 1-20, or a pharmaceutically acceptable salt or solvate thereof, wherein $R^8$ are H.

22. The compound of any one of embodiments 18-19, or a pharmaceutically acceptable salt or solvate thereof, wherein $R^7$ and $R^8$, together with the atom to which they are attached, form a 3-, 4-, 5-, 6-, or 7-membered cycloalkyl or heterocycloalkyl ring optionally substituted with 1, 2, 3, 4 or 5 independently selected $R^b$ substituents, and $R^b$ is as defined in any one of embodiments 1-2.

23. The compound of any one of embodiments 18-19, or a pharmaceutically acceptable salt or solvate thereof, wherein $R^7$ and $R^8$, together with the atom to which they are attached, form a 3-, 4-, 5-, 6-, or 7-membered cycloalkyl ring optionally substituted with 1, 2, 3, 4 or 5 independently selected $R^b$ substituents, and $R^b$ is as defined in any one of embodiments 1-2.

24. The compound of any one of embodiments 18-23, or a pharmaceutically acceptable salt or solvate thereof, wherein $R^7$ and $R^8$, together with the atom to which they are attached, form a 3-membered cycloalkyl ring optionally substituted with 1, 2, 3, 4 or 5 independently selected $R^b$ substituents, and $R^b$ is as defined in any one of embodiments 1-2.

25. The compound of any one of embodiments 18-24, or a pharmaceutically acceptable salt or solvate thereof, wherein q is 0.

26. The compound of any one of embodiments 18-24, or a pharmaceutically acceptable salt or solvate thereof, wherein q is 1.

27. The compound of any one of embodiments 18-24, or a pharmaceutically acceptable salt or solvate thereof, wherein q is 2.

28. The compound of any one of embodiments 18-27, or a pharmaceutically acceptable salt or solvate thereof, wherein $R^6$ is H, D, halo, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR)NR^cR^c$, $NR^cC(=NR^c)NR^cR^c$, $NR^c(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$ and $R^c$ is as defined in any one of embodiments 1-2.

29. The compound of embodiment 28, or a pharmaceutically acceptable salt or solvate thereof, wherein $R^c$ is H.

30. The compound of any one of embodiments 18-27, or a pharmaceutically acceptable salt or solvate thereof, wherein $R^6$ is $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, each of which is optionally substituted with 1, 2, 3, 4 or 5 independently selected $R^b$ substituents and wherein $R^b$ is as defined in any one of embodiments 1-2.

31. The compound of any one of embodiments 18-27, or a pharmaceutically acceptable salt or solvate thereof, wherein $R^6$ is $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, each of which is optionally substituted with 1, 2, 3, 4 or 5 independently selected $R^b$ substituents and wherein $R^b$ is as defined in any one of embodiments 1-2.

32. The compound of any one of embodiments 18-27, or a pharmaceutically acceptable salt or solvate thereof, wherein $R^6$ is $C_{3-10}$ cycloalkyl or 4-14 membered heterocycloalkyl, each of which is optionally substituted with 1, 2, 3, 4 or 5 independently selected $R^b$ substituents and wherein $R^b$ is as defined in any one of embodiments 1-2.

33. The compound of any one of embodiments 18-27, or a pharmaceutically acceptable salt or solvate thereof, wherein $R^6$ is $C_{3-10}$ cycloalkyl, which is optionally substituted with 1, 2, 3, 4 or 5 independently selected $R^b$ substituents and wherein $R^b$ is as defined in any one of embodiments 1-2.

34. The compound of any one of embodiments 18-27, or a pharmaceutically acceptable salt or solvate thereof, wherein $R^6$ is $C_{3-6}$ cycloalkyl, each of which is optionally substituted with 1, 2, 3, 4 or 5 independently selected $R^b$ substituents and wherein $R^b$ is as defined in any one of embodiments 1-2.

35. The compound of any one of embodiments 18-27, or a pharmaceutically acceptable salt or solvate thereof, wherein $R^6$ is $C_3$ cycloalkyl, each of which is optionally substituted with 1, 2, 3, 4 or 5 independently selected $R^b$ substituents and wherein $R^b$ is as defined in any one of embodiments 1-2.

36. The compound of embodiment 1, wherein the compound, or a pharmaceutically acceptable salt or solvate thereof, has a formula of

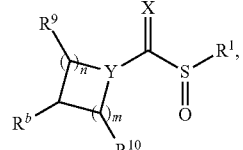

Formula (XII)

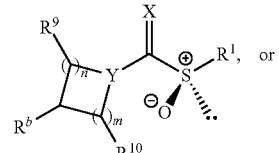

Formula (XII-a)

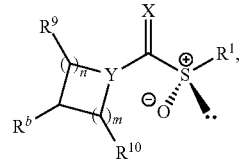

Formula (XII-b)

wherein n and m are each independently 0-6;

$R^9$ and $R^{10}$ are each independently H, D, halo, oxo, alkyl, alkoxy, alkenyl, alkynyl, haloalkyl, haloalkoxy, aryl, cycloalkyl, heteroaryl, heterocycloalkyl, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $SF_5$, $P(O)R^aR^a$, $P(O)(OR^a)(OR^a)$, $B(OR^a)_2$ and $S(O)_2NR^aR^a$; and the rest variables are as defined in embodiment 1.

37. The compound of embodiment 36, or a pharmaceutically acceptable salt or solvate thereof, wherein $R^1$ is $C_{1-6}$ alkyl.

38. The compound of embodiment 36, or a pharmaceutically acceptable salt or solvate thereof, wherein $R^1$ is methyl.

39. The compound of embodiment 36, wherein the compound, or a pharmaceutically acceptable salt or solvate thereof, has a formula of

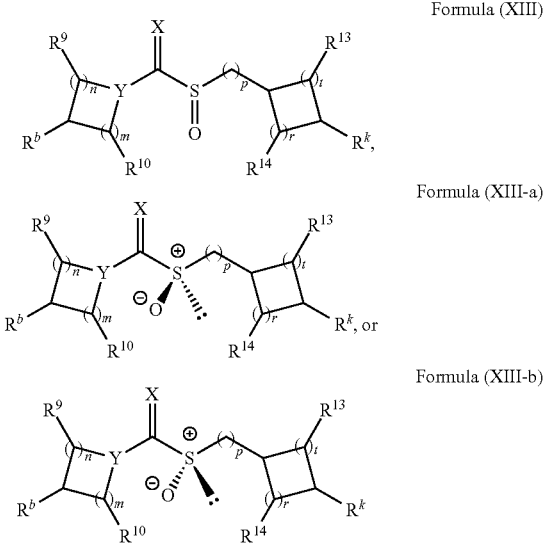

Formula (XIII)

Formula (XIII-a)

Formula (XIII-b)

wherein p, t, and r are each independently 0-6;

$R^{13}$ and $R^{14}$ are each independently H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$;

each R$^k$ substituent is independently selected from a bond, H, D, halo, oxo, C$_{1-10}$ alkyl, C$_{1-6}$ alkoxy, C$_{1-4}$ haloalkyl, C$_{1-4}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, (4-14 membered heterocycloalkyl)-C$_{1-4}$ alkyl, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$) NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)(=NR$^c$)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$;

wherein when R$^k$ is C$_{1-10}$ alkyl, C$_{1-6}$ alkoxy, C$_{1-4}$ haloalkyl, C$_{1-4}$ haloalkoxy, C$_{6-10}$ aryl, C$_{3-10}$ cycloalkyl, 5-10 membered heteroaryl, 4-14 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl- or (4-14 membered heterocycloalkyl)-C$_{1-4}$ alkyl, then R$^b$ is optionally substituted with 1, 2, or 3 independently selected R$^d$ substituents; and the rest variables are as defined in embodiment 1.

40. The compound of any one of embodiments 36-39, or a pharmaceutically acceptable salt or solvate thereof, wherein X is O.

41. The compound of any one of embodiments 36-40, or a pharmaceutically acceptable salt or solvate thereof, wherein Y is N.

42. The compound of any one of embodiments 39-41, or a pharmaceutically acceptable salt or solvate thereof, wherein r and t together are 2.

43. The compound of any one of embodiments 39-41, or a pharmaceutically acceptable salt or solvate thereof, wherein r and t together are 1.

44. The compound of any one of embodiments 36-43, or a pharmaceutically acceptable salt or solvate thereof, wherein R$^k$ is H.

45. The compound of any one of embodiments 39-44, or a pharmaceutically acceptable salt or solvate thereof, wherein p is 0.

46. The compound of any one of embodiments 39-44, or a pharmaceutically acceptable salt or solvate thereof, wherein p is 1.

47. The compound of any one of embodiments 36-46, or a pharmaceutically acceptable salt or solvate thereof, wherein R$^9$ is H.

48. The compound of any one of embodiments 36-47, or a pharmaceutically acceptable salt or solvate thereof, wherein R$^{10}$ is H.

49. The compound of any one of embodiments 36-48, or a pharmaceutically acceptable salt or solvate thereof, wherein n and m together are 4.

50. The compound of any one of embodiments 36-49, or a pharmaceutically acceptable salt or solvate thereof, wherein n and m together are 3.

51. The compound of any one of embodiments 36-50, or a pharmaceutically acceptable salt or solvate thereof, wherein n and m together are 2.

52. The compound of any one of embodiments 39-51, or a pharmaceutically acceptable salt or solvate thereof, wherein R$^{13}$ is H.

53. The compound of any one of embodiments 39-52, or a pharmaceutically acceptable salt or solvate thereof, wherein R$^{14}$ is H.

54. The compound of any one of embodiments 39-53, or a pharmaceutically acceptable salt or solvate thereof, wherein R$^b$ is H.

55. The compound of embodiment 1, wherein the compound, or a pharmaceutically acceptable salt or solvate thereof, has a formula of

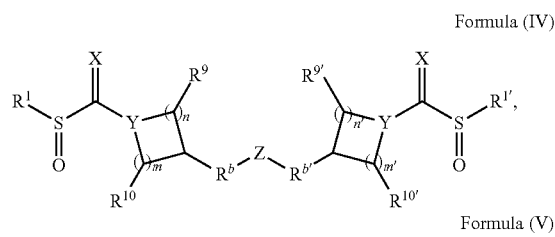

Formula (IV)

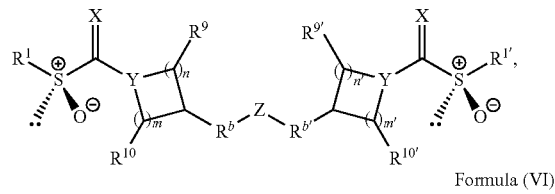

Formula (V)

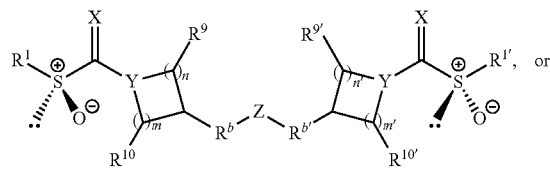

Formula (VI)

-continued

Formula (VII)

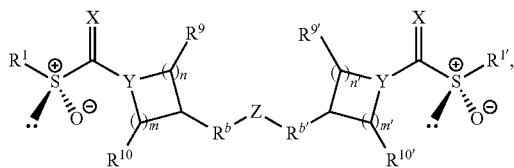

wherein:

n, m, n', and m' are each independently 0-6;

Z is a bond, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, —C(O)—, —OC(O)—, —OC(O)O—, —C(O)O(CH$_2$)$_v$CH$_2$O(O)C—, —OC(O)CH=CH(O)CO—, —OC(O)N(H) CH$_2$(CH$_2$)$_v$CH$_2$N(H)(O)CO—, OC(O)N(CH$_3$)(CH$_2$)$_v$CH$_2$N(CH$_3$)(O)CO—, —OC(O)N(CH$_3$)CH$_2$(CH$_2$)$_v$CH$_2$N(CH$_3$)(O)CO—, —C(O)O—, —C(S)—, —OC(S)—, —OC(S)O—, —C(O)O—, —C(=NR$^a$)—, —S—, —S—S—, —S(O)—, —S(O)$_2$—, —C(R$^a$)$_2$—, —N(R$^a$)—, —S(O)(R$^a$)—, —S(O)N(R$^a$)—, —P(O)(R$^a$)—, —P(O)(OR$^a$)—, and —B(OR$^a$)—, and —S(O)$_2$N(R$^a$)—;

v is 0-10;

$R^9$, $R^{10}$, $R^{9'}$, $R^{10'}$, and $R^{1'}$ are each independently H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$ NR$^a$C(=NOH)NR$^a$R$^a$, NR$^a$C(=NCN)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$;

each $R^{b'}$ substituent is independently selected from a bond, H, D, halo, oxo, $C_{1-10}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NR$^c$C(=NOH)NR$^c$R$^c$, NR$^c$C(=NCN)NR$^c$R$^c$, SF$_5$, P(O)R$^c$R$^c$, P(O)(OR$^c$)(OR$^c$), NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)(=NR$^c$)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$ or S(O)$_2$NR$^c$R$^c$;

wherein when $R^{b'}$ is $C_{1-10}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents; and the rest variables are as defined in embodiment 1.

56. The compound of embodiment 55, or a pharmaceutically acceptable salt or solvate thereof, wherein n and m together are 4.

57. The compound of any one of embodiments 55-56, or a pharmaceutically acceptable salt or solvate thereof, wherein n' and m' together are 4.

58. The compound of any one of embodiments 55-57, or a pharmaceutically acceptable salt or solvate thereof, wherein $R^9$ and $R^{9'}$ are the same.

59. The compound of any one of embodiments 55-58, or a pharmaceutically acceptable salt or solvate thereof, wherein $R^{10}$ and $R^{10'}$ are the same.

60. The compound of any one of embodiments 55-59, or a pharmaceutically acceptable salt or solvate thereof, wherein $R^9$, $R^{9'}$ $R^{10}$, and $R^{10'}$ are H.

61. The compound of any one of embodiments 55-60, or a pharmaceutically acceptable salt or solvate thereof, wherein the compound, or a pharmaceutically acceptable salt or solvate thereof, has a formula of z Formula (IV-I), Formula (IV-I)

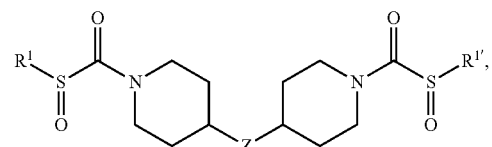

Formula (V-I)

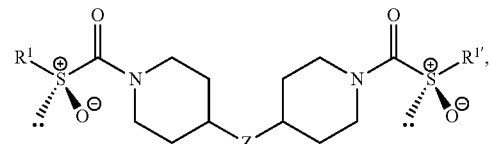

Formula (VI-I)

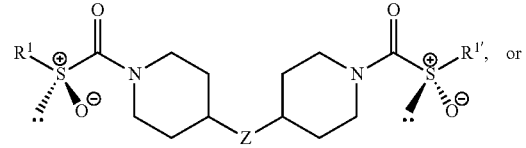

Formula (VII-I)

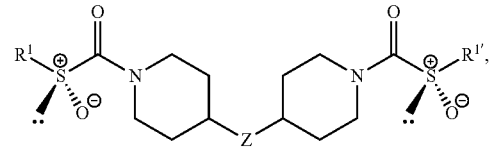

wherein the variables are as defined in embodiment 55.

62. The compound of any one of embodiments 55-61, or a pharmaceutically acceptable salt or solvate thereof, wherein $R^1$ and $R^{1'}$ are the same.

63. The compound of any one of embodiments 55-62, or a pharmaceutically acceptable salt or solvate thereof, wherein $R^1$ and $R^{1'}$ are cyclopropylmethyl.

64. The compound of any one of embodiments 55-63, or a pharmaceutically acceptable salt or solvate thereof, wherein Z is —OC(O)O—, —C(O)OCH$_2$CH$_2$O(O)C—, —OC(O)CH=CH(O)CO—, —OC(O)N(H)CH$_2$CH$_2$N(H)(O)CO—, —OC(O)N(CH$_3$)CH$_2$CH$_2$N(CH$_3$)(O)CO—, or —OC(O)N(CH$_3$)CH$_2$CH$_2$CH$_2$N(CH$_3$)(O)CO—.

65. The compound of embodiment 1, wherein the compound, or a pharmaceutically acceptable salt or solvate thereof, has a formula of

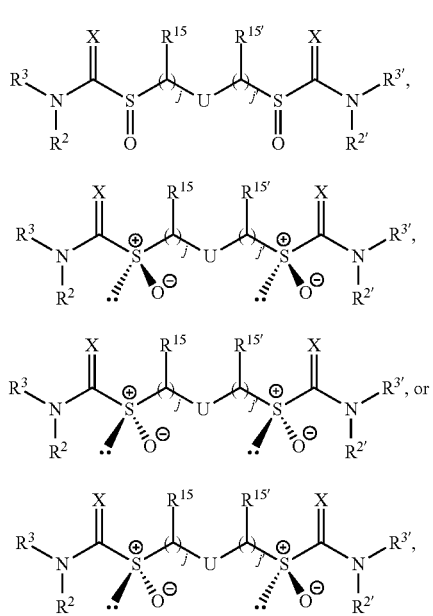

Formula (VIII)

Formula (IX)

Formula (X)

Formula (XI)

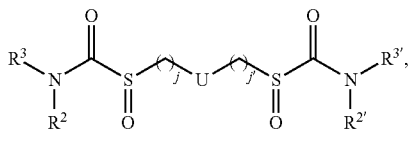

Formula (VIII)

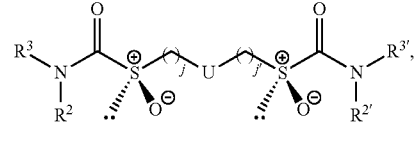

Formula (IX)

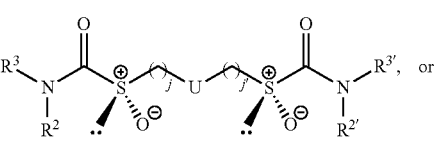

Formula (X)

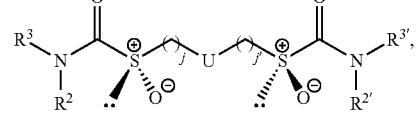

Formula (XI)

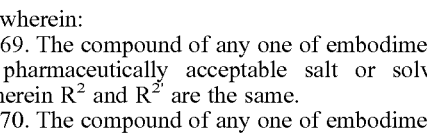

wherein.

j and j' are each independently 0-10;

U is a bond, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, —C(O)—, —OC(O)—, —OC(O)O—, —C(O)O(CH$_2$)$_w$CH$_2$O(O)C—, —OC(O)N(CH$_3$)(CH$_2$)$_w$CH$_2$N(CH$_3$)(O)CO—, —OC(O)N(CH$_3$)CH$_2$(CH$_2$)$_w$CH$_2$N(CH$_3$)(O)CO—, —C(O)O—, —C(S)—, —OC(S)—, —OC(S)O—, —C(O)O—, —C(=NR$^a$)—, —S—, —S—S—, —S(O)—, —S(O)$_2$—, —C(R$^a$)$_2$—, —N(R$^a$)—, —S(O)(R$^a$)—, —S(O)N(R$^a$)—, —P(O)(R$^a$)—, —P(O)(OR$^a$)—, and —B(OR$^a$)—, and —S(O)$_2$N(R$^a$)—.

w is 0-10;

$R^{2'}$, $R^{3'}$, $R^{15}$, and $R^{15'}$ are each independently H, D, halo, oxo, alkyl, alkoxy, alkenyl, alkynyl, haloalkyl, haloalkoxy, aryl, cycloalkyl, heteroaryl, heterocycloalkyl, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$C(=NOH)NR$^a$R$^a$, NR$^a$C(=NCN)NR$^a$R$^a$, NRS(O)R$^a$, NR$^a$S(O)$_2$R$^a$, NR$^a$S(O)$_2$NR$^a$R$^a$, S(O)R$^a$, S(O)NR$^a$R$^a$ S(O)$_2$R$^a$, SF$_5$, P(O)R$^a$R$^a$, P(O)(OR$^a$)(OR$^a$), B(OR$^a$)$_2$ and S(O)$_2$NR$^a$R$^a$; and the rest variables are as defined in embodiment 1.

66. The compound of embodiment 65, or a pharmaceutically acceptable salt or solvate thereof, wherein $R^3$ and $R^{15'}$ are the same.

67. The compound of any one of embodiments 65-66, or a pharmaceutically acceptable salt or solvate thereof, wherein $R^{15}$ and $R^{15'}$ are H.

68. The compound of any one of embodiments 65-67, wherein the compound, or a pharmaceutically acceptable salt or solvate thereof, has a formula of wherein:

69. The compound of any one of embodiments 65-68, or a pharmaceutically acceptable salt or solvate thereof, wherein $R^2$ and $R^{2'}$ are the same.

70. The compound of any one of embodiments 65-69, or a pharmaceutically acceptable salt or solvate thereof, wherein $R^2$ and $R^{2'}$ are ethyl.

71. The compound of any one of embodiments 65-70, or a pharmaceutically acceptable salt or solvate thereof, wherein $R^3$ and $R^{3'}$ are the same.

72. The compound of any one of embodiments 65-71, or a pharmaceutically acceptable salt or solvate thereof, wherein $R^3$ and $R^{3'}$ are ethyl.

73. The compound of any one of embodiments 65-72, or a pharmaceutically acceptable salt or solvate thereof, wherein j and j' are the same.

74. The compound of any one of embodiments 65-73, or a pharmaceutically acceptable salt or solvate thereof, wherein j and j' are 2.

75. The compound of any one of embodiments 65-74, or a pharmaceutically acceptable salt or solvate thereof, wherein U is —OC(O)O—, —C(O)OCH$_2$CH$_2$O(O)C—, —OC(O)CH=CH(O)CO—, —OC(O)N(H)CH$_2$CH$_2$N(H)(O)CO—, —OC(O)N(CH$_3$)CH$_2$CH$_2$N(CH$_3$)(O)CO—, or —OC(O)N(CH$_3$)CH$_2$CH$_2$CH$_2$N(CH$_3$)(O)CO—.

76. The compound of any one of embodiments 1-2, or a pharmaceutically acceptable salt or solvate thereof, wherein the compound has a formula of

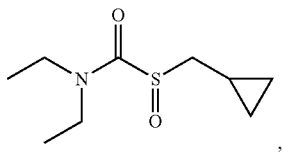

,

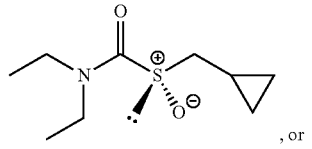

, or

-continued

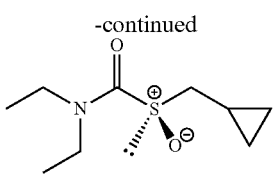

77. The compound of any one of embodiments 1-2, or a pharmaceutically acceptable salt or solvate thereof, wherein the compound has a formula of or

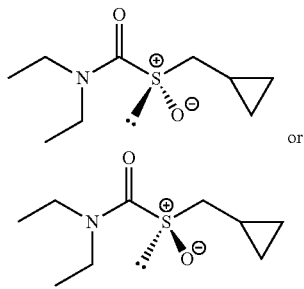

78. The compound of any one of embodiments 1-2, or a pharmaceutically acceptable salt or solvate thereof, wherein the compound has a formula of

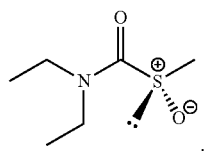

79. The compound of any one of embodiments 1-2, or a pharmaceutically acceptable salt or solvate thereof, wherein the compound has a formula of

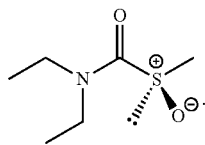

80. The compound of any one of embodiments 1-2, or a pharmaceutically acceptable salt or solvate thereof, wherein the compound has a formula of

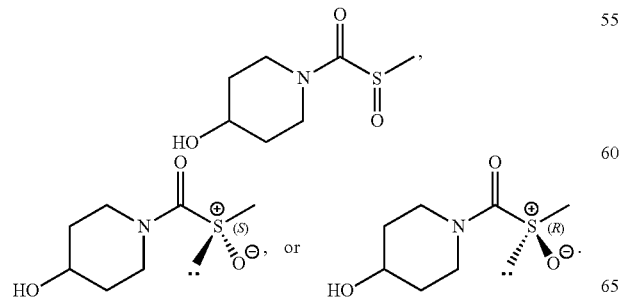

81. The compound of any one of embodiments 1-2, or a pharmaceutically acceptable salt or solvate thereof, wherein the compound has a formula of

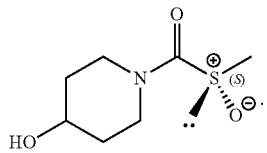

82. The compound of any one of embodiments 1-2, or a pharmaceutically acceptable salt or solvate thereof, wherein the compound has a formula of

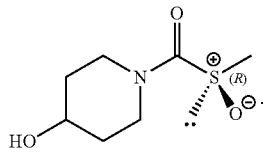

83. The compound of embodiment 1, or a pharmaceutically acceptable salt or solvate thereof, wherein the compound is selected from the group consisting of:

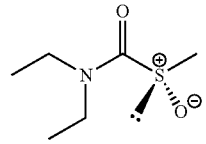

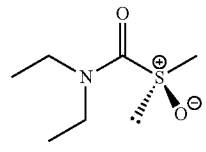

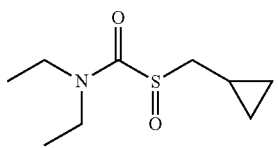

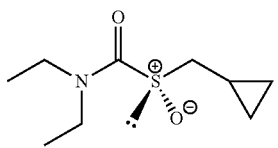

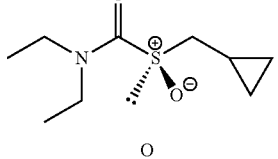

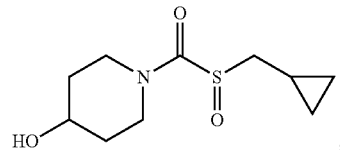

83
-continued
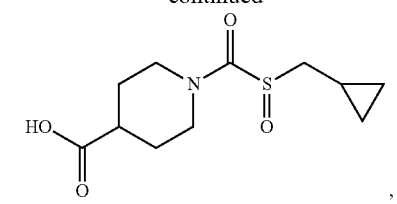
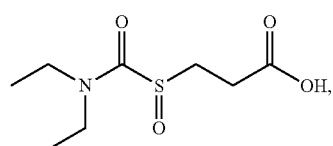
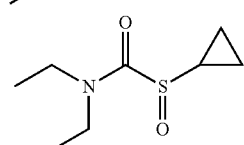
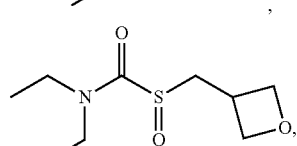
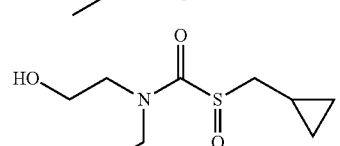
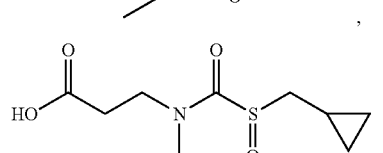
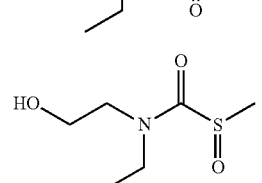
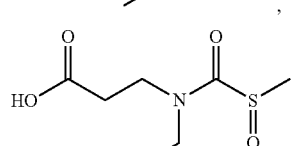
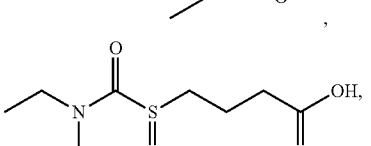
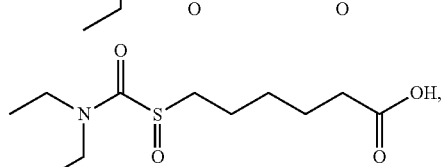
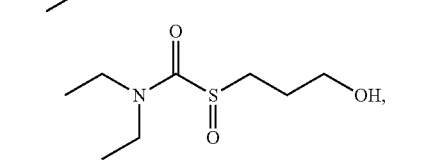
84
-continued
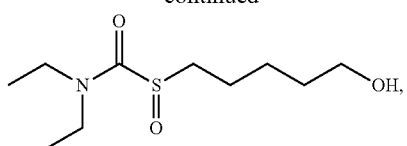
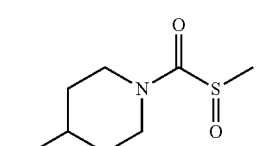
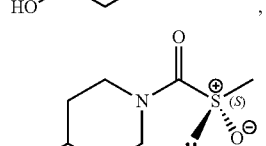
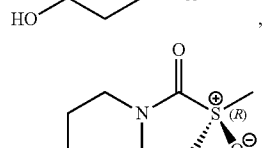
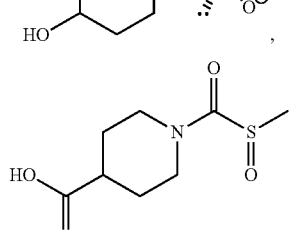
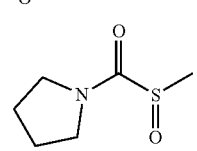
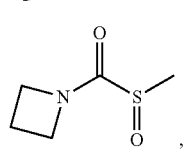
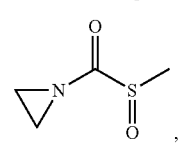
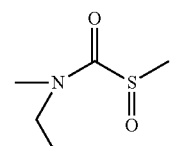
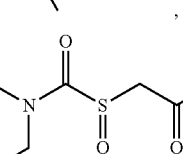
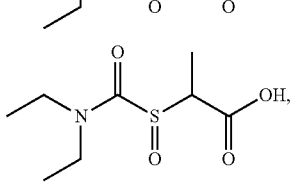

85
-continued
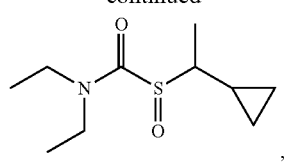
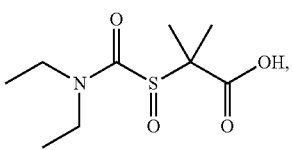
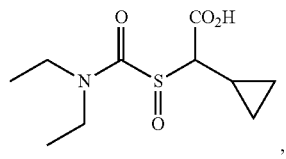
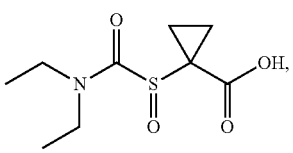
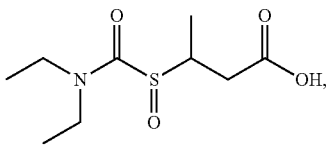
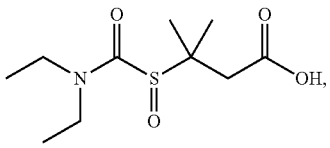
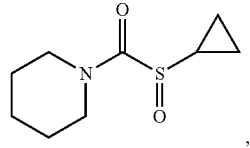
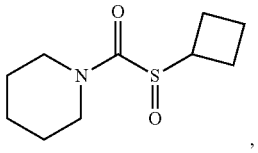
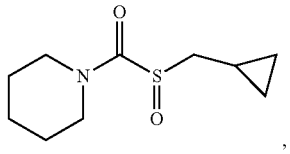
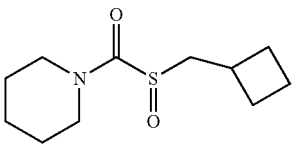
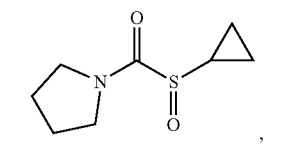
86
-continued
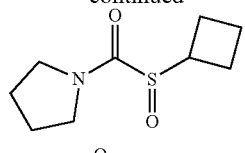
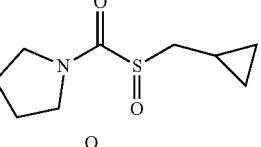
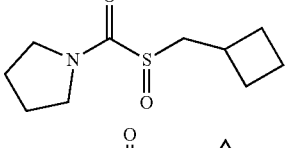
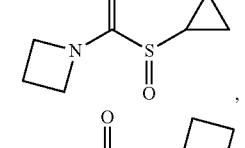
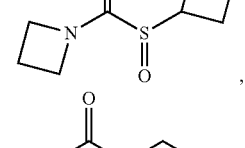
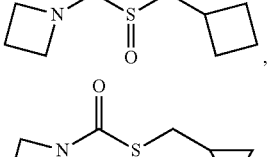
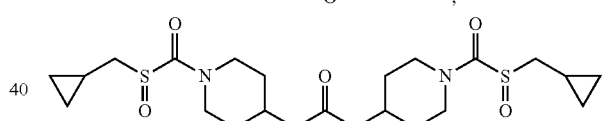
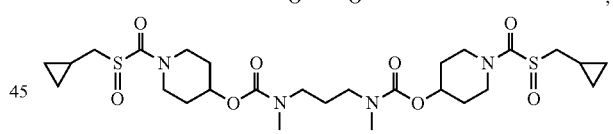
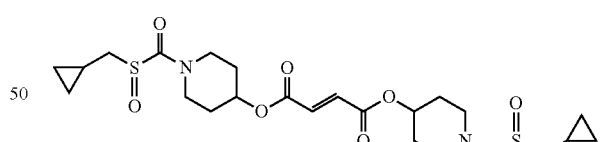
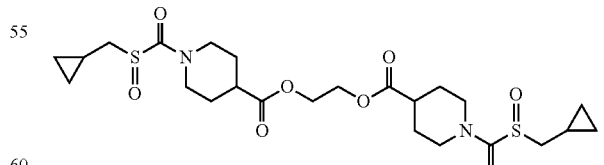
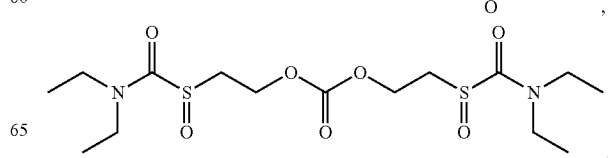

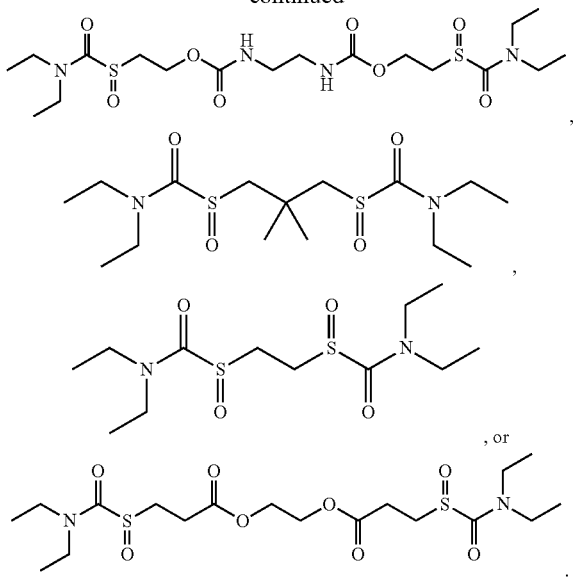
, or

84. A pharmaceutical composition comprising a compound according to any one of embodiments 1-83, or a pharmaceutically acceptable salt or solvate thereof, and optionally a pharmaceutically acceptable excipient.

85. The pharmaceutical composition of embodiment 84, wherein the pharmaceutical composition comprises an enantiomeric excess of at least 90% of one enantiomer of the compound, or a pharmaceutically acceptable salt or solvate thereof.

86. The pharmaceutical composition of embodiment 84, wherein the pharmaceutical composition comprises an enantiomeric excess of at least 95% of one enantiomer of the compound, or a pharmaceutically acceptable salt or solvate thereof.

87. The pharmaceutical composition of embodiment 84, wherein the pharmaceutical composition comprises an enantiomeric excess of at least 98% of one enantiomer of the compound, or a pharmaceutically acceptable salt or solvate thereof.

88. The pharmaceutical composition of embodiment 84, wherein the pharmaceutical composition comprises an enantiomeric excess of at least 99% of one enantiomer of the compound, or a pharmaceutically acceptable salt or solvate thereof.

89. A method of inhibiting an ALDH2 enzyme comprising: contacting the ALDH2 enzyme with an effective amount of a compound of any one of embodiments 1-83, or a pharmaceutically acceptable salt or solvate thereof, or a pharmaceutical composition of any one of embodiments 79-83.

90. A method of treating or preventing an alcohol related disorder in a subject or a subject in need thereof comprising administering to the subject, a compound of any one of embodiments 1-83, or a pharmaceutically acceptable salt or solvate thereof, or a pharmaceutical composition of any one of embodiments 84-88.

91. The method of embodiment 90, wherein the alcohol related disorder is alcohol use disorder, alcohol induced disorder, alcohol abuse, alcohol dependence, alcohol intoxication, alcohol withdrawal, or any combination thereof.

92. A method of treating or preventing alcohol use disorder in a subject or a subject in need thereof comprising administering to the subject, a compound of any one of embodiments 1-83, or a pharmaceutically acceptable salt or solvate thereof.

93. A compound of any one of embodiments 1-83 in use for inhibiting an ALDH2 enzyme in a subject, wherein the use comprises administering to the subject an effective amount of the compound of any one of embodiments 1-83, or a pharmaceutically acceptable salt, a solvate, a pharmaceutical composition, or a prodrug thereof.

94. A pharmaceutical composition of any one of embodiments 84-88 in use for inhibiting an ALDH2 enzyme in a subject, wherein the use comprises administering to the subject an effective amount of the pharmaceutical composition of any one of embodiments 84-88.

95. Use of a compound of any one of embodiments 1-83 in the manufacture of a formulation inhibiting an ALDH2 enzyme in a subject, wherein the use comprises administering to the subject an effective amount of the compound of any one of embodiments 1-83, or a pharmaceutically acceptable salt, a solvate, a pharmaceutical composition, or a prodrug thereof.

96. Use of a pharmaceutical composition of any one of embodiments 84-88 for inhibiting an ALDH2 enzyme in a subject, wherein the use comprises administering to the subject an effective amount of the pharmaceutical composition of any one of embodiments 84-88.

97. A compound of any one of embodiments 1-83 in use for treating or preventing an alcohol related disorder in a subject or a subject in need thereof, wherein the use comprises administering to the subject an effective amount of the compound of any one of embodiments 1-83, or a pharmaceutically acceptable salt, a solvate, a pharmaceutical composition, or a prodrug thereof.

98. A pharmaceutical composition of any one of embodiments 84-88 in use for treating or preventing an alcohol related disorder in a subject or a subject in need thereof, wherein the use comprises administering to the subject an effective amount of the pharmaceutical composition of any one of embodiments 84-88.

99. Use of a compound of any one of embodiments 1-83 in the manufacture of a formulation treating or preventing an alcohol related disorder in a subject or a subject in need thereof, wherein the use comprises administering to the subject an effective amount of the compound of any one of embodiments 1-83, or a pharmaceutically acceptable salt, a solvate, a pharmaceutical composition, or a prodrug thereof.

100. Use of a pharmaceutical composition of any one of embodiments 84-88 for treating or preventing an alcohol related disorder in a subject or a subject in need thereof, wherein the use comprises administering to the subject an effective amount of the pharmaceutical composition of any one of embodiments 84-88.

101. The use of any one of embodiments 93-100, wherein the alcohol related disorder is alcohol use disorder, alcohol induced disorder, alcohol abuse, alcohol dependence, alcohol intoxication, alcohol withdrawal, or any combination thereof.

102. A compound of any one of embodiments 1-83 in use for treating or preventing alcohol use disorder in a subject or a subject in need thereof, wherein the use comprises administering to the subject an effective amount of the compound of any one of embodiments 1-83, or a pharmaceutically acceptable salt, a solvate, a pharmaceutical composition, or a prodrug thereof.

103. A pharmaceutical composition of any one of embodiments 84-88 in use for treating or preventing alcohol use disorder in a subject or a subject in need thereof, wherein the use comprises administering to the subject an effective amount of the pharmaceutical composition of any one of embodiments 84-88.

104. Use of a compound of any one of embodiments 1-83 in the manufacture of a formulation treating or preventing alcohol use disorder in a subject or a subject in need thereof, wherein the use comprises administering to the subject an effective amount of the compound of any one of embodiments 1-83, or a pharmaceutically acceptable salt, a solvate, a pharmaceutical composition, or a prodrug thereof.

105. Use of a pharmaceutical composition of any one of embodiments 84-88 for treating or preventing alcohol use disorder in a subject or a subject in need thereof, wherein the use comprises administering to the subject an effective amount of the pharmaceutical composition of any one of embodiments 84-88.

106. A method of reducing the amount of alcohol consumed by a subject suffering from, diagnosed with, or suspected of having alcohol use disorder, the method comprising administering to the subject, a compound of any one of embodiments 1-83, or a pharmaceutically acceptable salt or solvate thereof, or a pharmaceutical composition of any one of embodiments 84-88.

107. A method of reducing alcoholic cravings in a subject with alcohol use disorder, the method comprising administering to the subject, a compound of any one of embodiments 1-83, or a pharmaceutically acceptable salt or solvate thereof, or a pharmaceutical composition of any one of embodiments 84-88.

108. The method of embodiment 107, wherein the cravings are measured on a Visual Analogue Scale of Craving.

109. The method of embodiments 107 or 108, wherein the subject has a reduction in the craving scale after 2, 3, 4, 5, 6, 7, 8, 9, 10, 11, 12, or 13 weeks of being treated with the pharmaceutical composition.

110. The method of embodiment 109, wherein the reduction on the Visual Analogue Scale of Craving is about, or at least, 5, 10, 15, 20, 30, 40, 50, 60, 70, or 75 points.

111. A method of increasing the percentage of no heavy drinking days for a subject with alcohol use disorder, the method comprising administering to the subject, a compound of any one of embodiments 1-83, or a pharmaceutically acceptable salt or solvate thereof, or a pharmaceutical composition of any one of embodiments 84-88.

112. The method of embodiment 111, wherein the percentage of no heavy drinking days is increased by at least, or about, 5, 10, 15, 20, 30, 40, 50, 60 70, 80, 90, 100, 200, or 300%.

The following examples are illustrative, but not limiting, of compositions, methods of preparation thereof, and methods of use thereof described herein. Other suitable modifications and adaptations of the variety of conditions and parameters normally encountered in therapy, synthesis, and other embodiments disclosed herein are within the spirit and scope of the embodiments provided for herein.

Compounds of the disclosure can be prepared using numerous preparatory reactions known in the literature. The Schemes below provide general guidance in connection with preparing the compounds provided herein. One skilled in the art would understand that the preparations shown in the Schemes can be modified or optimized using general knowledge of organic chemistry to prepare various compounds. Example synthetic methods for preparing compounds are provided in the Schemes below.

EXAMPLES

Example 1: Synthesis of Compounds

General Schemes:

Compounds in the formulas as described herein may be synthesized according to Schemes 1, 2, 3, 4 using materials described therein.

In one embodiment, the compounds of Formulas (I), (III), (XII) and (XIII) may be synthesized as described in Scheme 1. Compounds 1.2, 1.3, and 1.4 (Scheme 1) may be prepared through an intermediate 1.1 where the leaving group (LG) can be, but not limited to, chloride, imidazole, optionally substituted phenyloxy or the like. Intermediate 1.1 can be prepared from reacting amines with phosgene, triphosgene, carbonylimidazole, phenyl chloroformate, 4-nitrophenyl chloroformate or the like. Carbamothiolate 1.2 can be obtained from reaction of intermediate 1.1 with a thiol under basic conditions for example, but not limited to, an aqueous base such as, but not limited to, sodium hydroxide, potassium hydroxide or the like in solvents such as, but not limited to, THF, dioxane, or the like under ambient temperature or with heating in the presence of a phase transfer catalyst such as, but not limited to, tetrahexylammonium chloride, tetrabutylammonium iodide or the like. Alternatively, the reaction can be carried out using organic bases such as, but not limited to, triethylamine, DBU, DBN, or the like in solvents such as, but not limited to, THF, dioxane or the like at ambient temperature or with heating. Oxidation of compound 1.2 can give thiolcarbamate sulfoxide compound 1.3 and thiolcarbamate sulfone compound 1.4. This can be carried out with oxidizing agents such as, but not limited to, meta-chloroperoxybenzoic acid (mCPBA), hydrogen peroxide, tert-butyl hydroperoxide (TBHP) in the presence of metal catalyst such as Iron(III) chloride, VO(acac)$_2$ with suitable ligands and those in the art and at a temperature such as, but not limited to, −20° C., RT or with heating. The variables in Scheme 1 are as defined in the embodiments as described herein

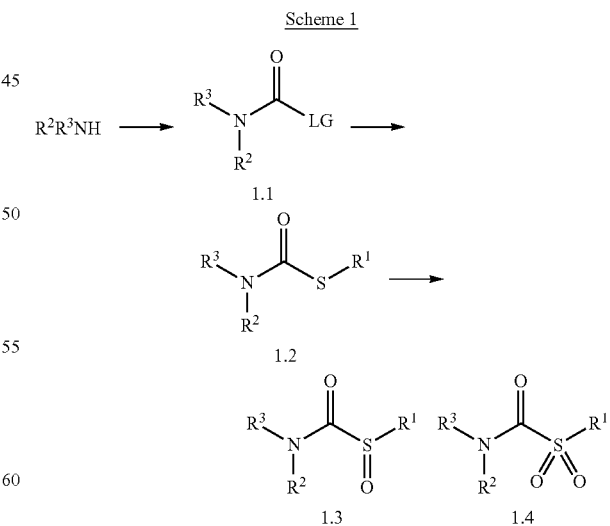

Scheme 1

In another embodiment, the compounds of Formulas (I-a), (III-a), (XII-a), (XIII-a), (I-b), (III-b), (XII-b) and (XIII-b) may be synthesized as described in Scheme 2. Derivatives of chiral thiolcarbamate sulfoxides compounds 1.3.a and 1.3.b can be obtained from compounds 1.2 or 1.3 using methods known to those in the art, but not limited to those shown in Scheme 2. Compounds 1.3.a and 1.3.b can be prepared through separation of the modified and unmodified enantiomers and diastereoisomers under gas-liquid or liquid chromatography in a chiral environment, for example, on a chiral support, such as silica with a bound chiral ligand or in the presence of a chiral solvent. In another embodiment, compounds 1.3 can combine with an agent L1 through covalent or non-covalent interaction to form compounds of formula 1.4.a selectively which upon release of the agent L1 can give single enantiomers or diastereoisomers of formula 1.3.a. In another embodiment, derivatives of chiral thiolcarbamate sulfoxides compounds 1.3.a and 1.3.b can be prepared from asymmetric oxidation using chiral reagents or through enzymatic oxidation known to those in the art. There exist multiple chiral reagents and chiral ligands such as those based on BINOL, salan, porphyrin, PyBOX and the like and asymmetric oxidation can be carried out by those with skills in the art but not limited to the above listed reagents. Asymmetric oxidation of compound 1.2 can be carried out using conditions such as titanium(IV) isopropoxide, chiral ligands such as diethyl D-tartrate, diethyl L-tartrate (Henri B. Kagan, Phosphorus and Sulfur, 1986, 27, 127-132) or the like and oxidants such as TBHP or the like and at a temperature such as −40° C., −20° C. or RT. Asymmetric oxidation of 1.2 can be carried out under chiral Bronsted acids such as imidodiphosphoric acid catalysts (Saihu Liao, et al., JACS, 2012, 134, 10765-10768) with oxidants such as hydrogen peroxide and at RT. Asymmetric oxidation of 1.2 can also be carried out under metal-catalyzed oxidation such as Fe(salan) complexes (Hiromichi Egami, Tsutomu Katsuki, JACS, 2007, 129, 8940-8941) with oxidants such as hydrogen peroxide and at RT. Each of the references described herein is incorporated by reference in its entirety. The variables in Scheme 2 are as defined in the embodiments as described herein Scheme 2

Method A. Chiral Separation

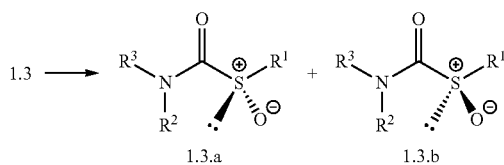

Method B. Chiral Resolution

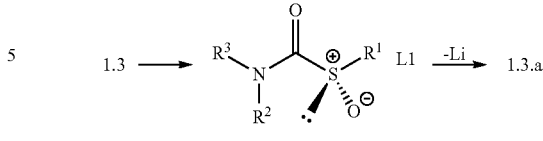

Method C. Asymmetric Oxidation

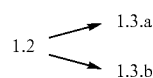

In another embodiment, compounds of Formula (IV)-(XI) can be synthesized by connecting the compounds of Formulas (I), (III), (XII), (XIII), (I-a), (III-a), (XII-a), (XII-a), (I-b), (III-b), (XII-b) and (XIII-b) via linkers with functional groups such as but not limited to esters, carbonates, or carbamates or the like (Scheme 3 and Scheme 4). Compounds 3.1, 3.3, 4.1 and 4.3 can be prepared from the above schemes with or without protecting groups with those skilled in the art. Compounds 3.2 and 4.2 can be prepared from esterification of acids compounds 3.1 and 4.1 respectively with diols under conditions such as, but not limited to, DCC, EDC, PyBOP, and the like and in the absence or presence of a base such as, but not limited to, DMAP, TEA, or the like and in solvents such as, but not limited to, DCM, THF, DMF or the like. Carbonates of compounds 3.4 and 4.4 can be prepared from alcohols compounds 3.3 and 4.3, respectively with phosgene, triphosgene, carbonyldiimidazole (CDI) or the like and in the presence of a base such as, but not limited to, TEA, pyridine or the like and in solvents such as, but not limited to, DCM, THE or the like. Esters of compounds 3.5 and 4.5 can be prepared from esterification of alcohols compounds 3.3 and 4.3 respectively with diacids under conditions such as, but not limited to, DCC, EDC, PyBOP, and the like and in the absence or presence of a base such as, but not limited to, DMAP, TEA, or the like and in solvents such as, but not limited to, DCM, THF, DMF or the like. Carbamates of compounds 3.6 and 4.6 can be prepared from esterification of alcohols compounds 3.3 and 4.3 respectively with bis-chloroformates, bis-p-nitrophenyl carbamates, or the like and in the absence or presence of a base such as, but not limited to, TEA, pyridine, or the like and in solvents such as, but not limited to, DCM, THF, DMF or the like. In another embodiment, the above chemistries can be used with compounds containing chiral centers to give enantiomers or diastereoisomers. In another embodiment, the carbonates, bis-esters, bis-carbamates can be synthesized as the bis-carbamothiolates which upon oxidation with or without chiral agents to give the bis-sulfoxides of compounds 3.2, 3.4, 3.5, 3.6, 4.2, 4.4, 4.5, 4.6 as shown in Scheme 3 and Scheme 4. The variables in Scheme 3 and Scheme 4 are as defined herein and in the embodiments, as described herein Scheme 3

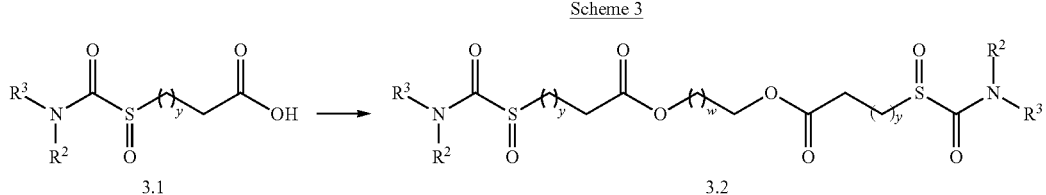

-continued

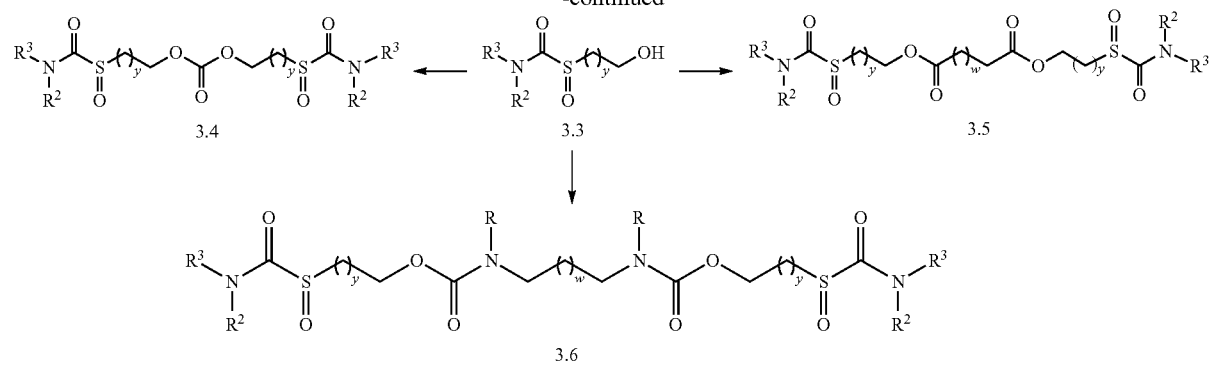

y = 0-6 w = 0-10

Scheme 4

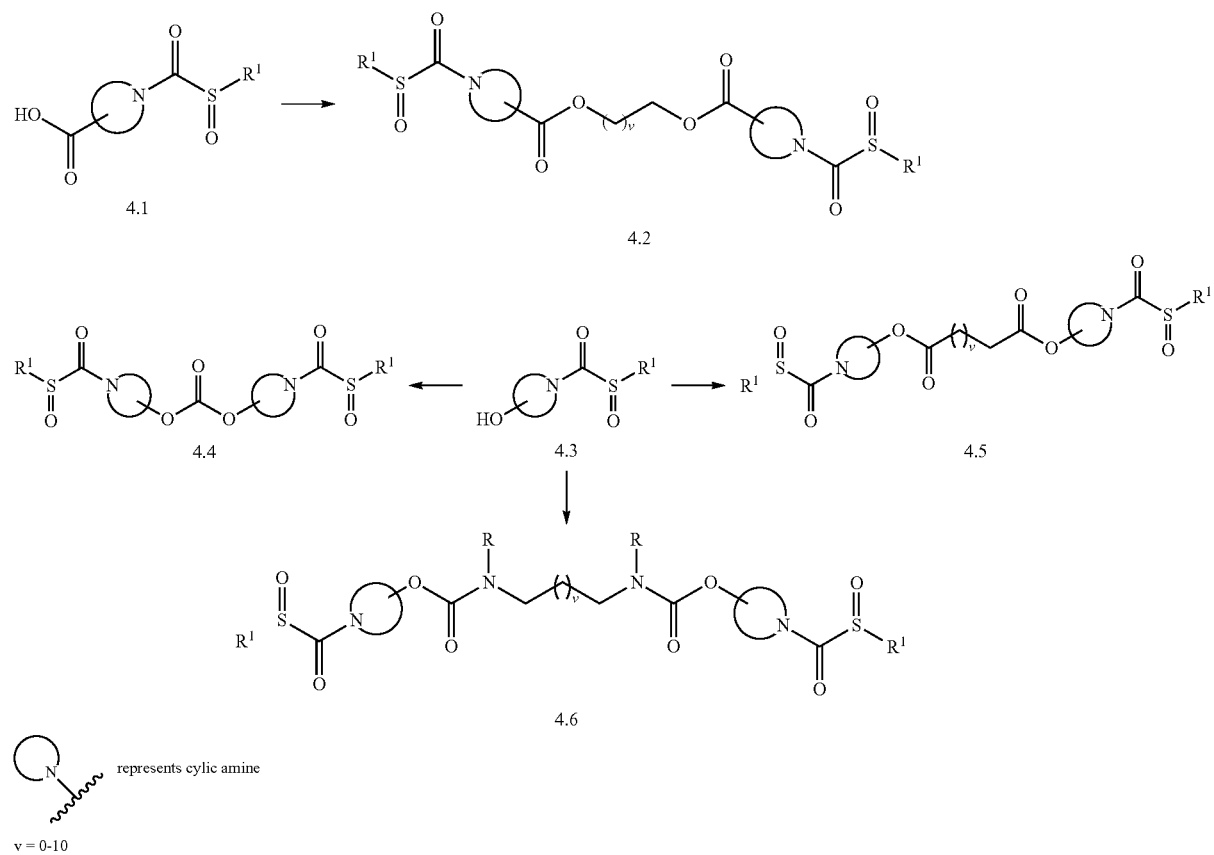

v = 0-10

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Isolation and purification of the chemical entities and intermediates described herein can be effected, if desired, by any suitable separation or purification procedure such as, but not limited to, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example, by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example, enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The Examples disclosed herein are for illustrative purposes only and are not intended to limit the scope of the present disclosure. This is in no way meant to limit the scope of utility of the compounds as described herein. Additional examples contained within were determined to have the shown configuration by spectroscopic methods well known to those skilled in the art including, but not limited to, 1D and 2D NMR methods, vibrational circular dichroism and X-ray crystallography.

Equipment Description $^1$H NMR spectra were recorded on a Varian spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad). Analytical HPLCs were recorded on Agilent 1100 series or 1260 series HPLCs equipped with DAD and VWD detectors. LCMS were recorded on an 1100 series Agilent HPLC connected to a Waters Micromass Spectrometer. IR spectra were recorded on a Thermo Nicolet 380 instrument using a KBr Salt Plate. Optical rotation was performed on a JASCO P1010 polarimeter with 100 mm cell.

Example 1-1: N,N-diethyl-1-(methylsulfide)methanamide

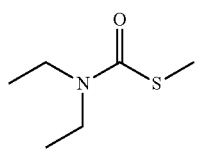

To a solution of 200 g of 21 wt % of aqueous sodium methane thiolate solution (599 mmol) was added a solution of N,N-diethyl carbamoyl chloride (68.3 mL, 539 mmol) in THF (600 mL), followed by 4.7 g (2 mol %) of tetrahexylammonium chloride. The biphasic mixture was stirred rapidly and heated to reflux under nitrogen capturing excess sulfide gasses with a bleach trap. After reflux for 3 h, the solution was cooled to rt. The biphasic reaction was extracted with 1 L of diethyl ether, and the organic phase was washed with brine and dried over sodium sulfate. After evaporation under reduced pressure, the crude oil was subjected to chromatography (Sorbtech silica gel 60; dichloromethane) to afford N,N-diethyl-1-(methylsulfide)methanamide Example 1-1 as a light yellow oil (76.8 g; 97%). $^1$H NMR (400 MHz, CDCl$_3$): δ 3.36 (br s, 4H, 2×CH$_2$), 2.30 (s, 3H, SCH$_3$), 1.15 (br s, 6H, 2×CH$_3$).

Example 1-2: N,N-diethyl-1-(methylsulfinyl)methanamide (1-2)

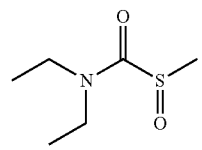

To a solution of N,N-diethyl-1-(methylsulfide)methanamide (26.7 g; 181.6 mmol) in 1 L of dichloromethane cooled to −15° C. was added dropwise a solution of 77% m-chloroperbenzoic acid (36.6 g; 163.4 mmol) at a rate keeping the temperature of the reaction mixture not to exceed −10° C. during addition. Upon completion of addition, the reaction was cooled back to −15° C., and the m-chlorobenzoic acid precipitate was removed by filtration. The filtrate was evaporated to dryness, and the crude product was subjected to chromatography (silica gel; methyl-t-butyl ether) followed by a second chromatography (silica gel; 10% MeOH in MTBE) afforded N,N-diethyl-1-(methylsulfinyl)methanamide Example 1-2 as a light yellow oil (23.8 g; 80%). $^1$H NMR (400 MHz, CDCl$_3$): δ 3.63-3.53 (m, 2H, CH$_2$), 3.51-3.42 (m, 2H, CH$_2$), 2.76 (s, 3H, SCH$_3$), 1.28 (t, 3H, J=7.00 Hz, CH$_3$), 1.17 (t, 3H, J=7.20 Hz, CH$_3$); $^{13}$C NMR (100 MHz, CDCl$_3$): δ 168.0 (CO), 42.8 (CH$_2$), 41.0 (CH$_2$), 37.4 (SCH$_3$), 14.5 (CH$_3$), 12.5 (CH$_3$); HPLC-MS: m/e 186.4 (M+Na$^+$)

Examples 1-2A and 1-2B:enantiomer (−)-N,N-diethyl-1-(methylsulfinyl)methanamide (1-2A) (Peak-1) and enantiomer (+)-N,N-diethyl-1-(methylsulfinyl)methanamide (1-2B) (Peak-2)

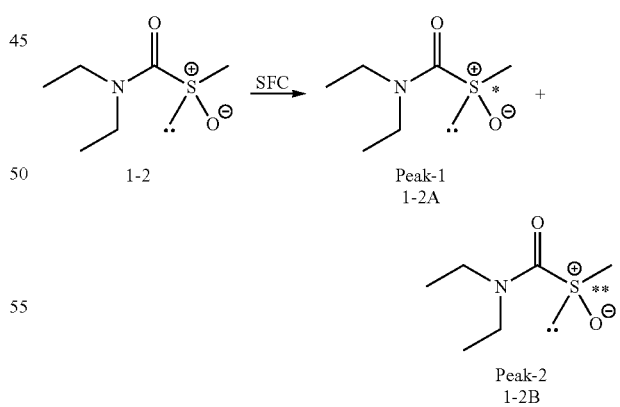

Racemic N,N-diethyl-1-(methylsulfinyl)methanamide (~850 mg) (1-2) was separated using chiral SFC conditions to give 2 enantiomers, Examples 1-2A: (−)-enantiomer (Peak-1) (331 mg, >97% ee, RT 4.88 min, $[α]^{22}_D$=−11.8° (c=0.0049 g/ml, CHCl$_3$)) and Examples 1-2B: (+)-enantiomer (Peak-2) (369 mg, >97% ee, RT 5.27 min, $[α]^{22}_D$=+8.6° (c=0.0056 g/ml, CHCl$_3$)).

Preparative SFC Conditions:
  CHIRALPAK® AD-H 2×(3×25 cm)
  10% methanol (0.05% formic acid)/CO$_2$, 100 bar
  80 mL/min (make-up flow of 100% MeOH, 5 mL/min), 220 nm
  Injection volume: 0.5 mL, 20 mg/mL in iso-propanol
Analytical SFC Conditions:
  CHIRALPAK© AD-H (25×0.46 cm)
  10% methanol/CO$_2$, 100 bar
  2.0 mL/min, 220 nm Determination of the Absolute Configurations of Example 1-2A and Example 1-2B The absolute configuration of Example 1-2B was determined to have a represented formula of

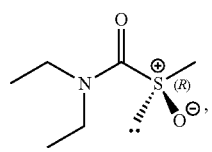

wherein the chirality of the Sulfur is (R) based on Vibrational circular dichroism (VCD) analysis. Therefore, the absolute configuration of Example 1-2A was determined to have a represented formula of

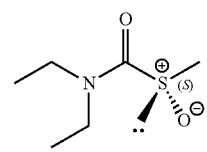

based on overly vibrational circular dichroism (VCD) analysis. The conditions and procedures for the VCD analysis are described herein.

| GENERAL INFORMATION | |
|---|---|
| VCD-spectrometer | ChiralIR w/DualPEM |
| RESULTS | |
| Absolute Configuration of Example 1-2A is (R) | Confidence Level: 99%* |
| Absolute Configuration of Example 1-2A is (S) | Confidence Level: 99%* |
| MEASUREMENT PARAMETERS | |
| Concentration | 10 mg/250 uL |
| Solvent | CDCl3 |
| Resolution | 4 cm$^{-1}$ |
| PEM setting | 1400 cm$^{-1}$ |
| Number of scans/ Measurement time | 24 hours enantiomer and racemic |
| Sample cell | BaF2 |
| Path length | 100 μm |
| CALCULATION DETAILS | |
| Molecular Mechanics Force Field | MMFF94 (Compute VOA) |
| DFT Software version | Gaussian '09 |
| Number of conformers used for Boltzmann sum | 4 (cc-pVTZ)/B3LYP) |
| Methodology and basis sets for DFT calculations | 6-31Gd, cc-pVTZ, cc-pVQZ/B3LYP, B3PW91/CPCM (Chloroform) |
| Enantiomer used for calculation | R |
| Total calculated conformers | 14 (6-31Gd)/4 (cc-pVTZ) |
| Number of low-energy conformations shown in report | 4 |

*The confidence level is a measure of the degree of congruence between a calculated and measured spectrum. It's a measure of quality or degree of agreement between calculated and measured spectra. If identical spectra are being compared, the confidence level is 100%.

Figure 13:
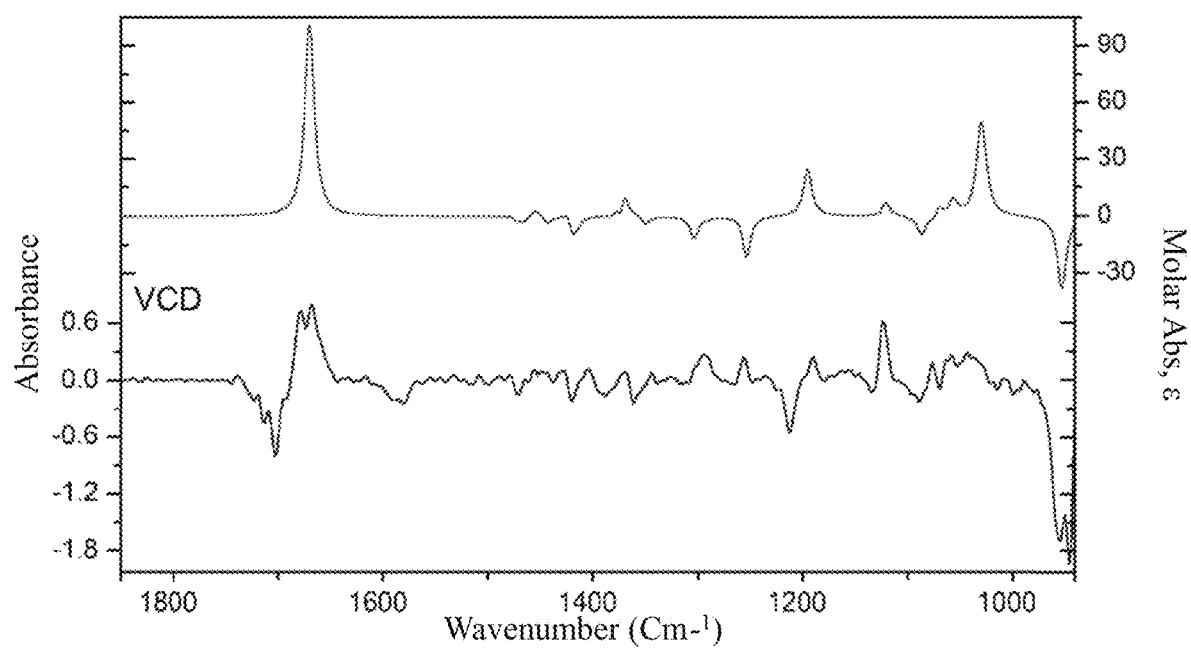
FIG. 13 illustrates the comparison of the experimental and theoretically calculated infrared spectra (IR) spectra of the enantiomer Example 1-2B on chiral column.
Figure 14:
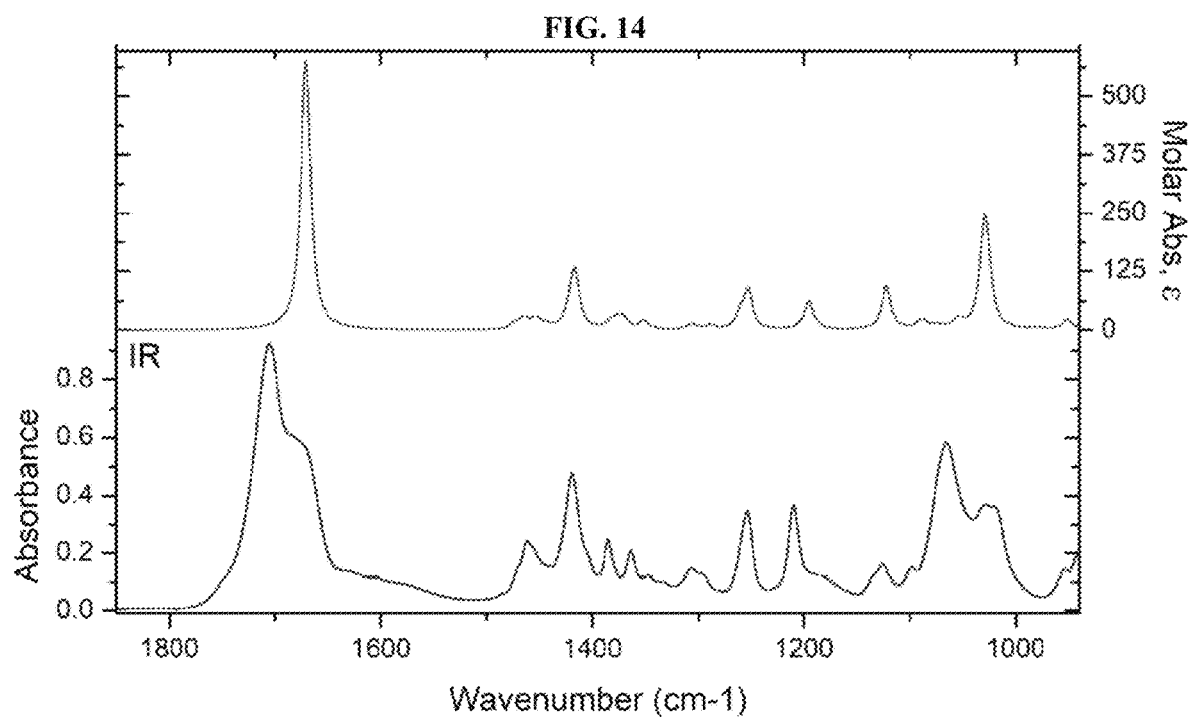
FIG. 14 illustrates the comparison of the experimental and theoretically calculated vibrational circular dichroism (VCD) spectra of the enantiomer Example 1-2B.
Figure 15:
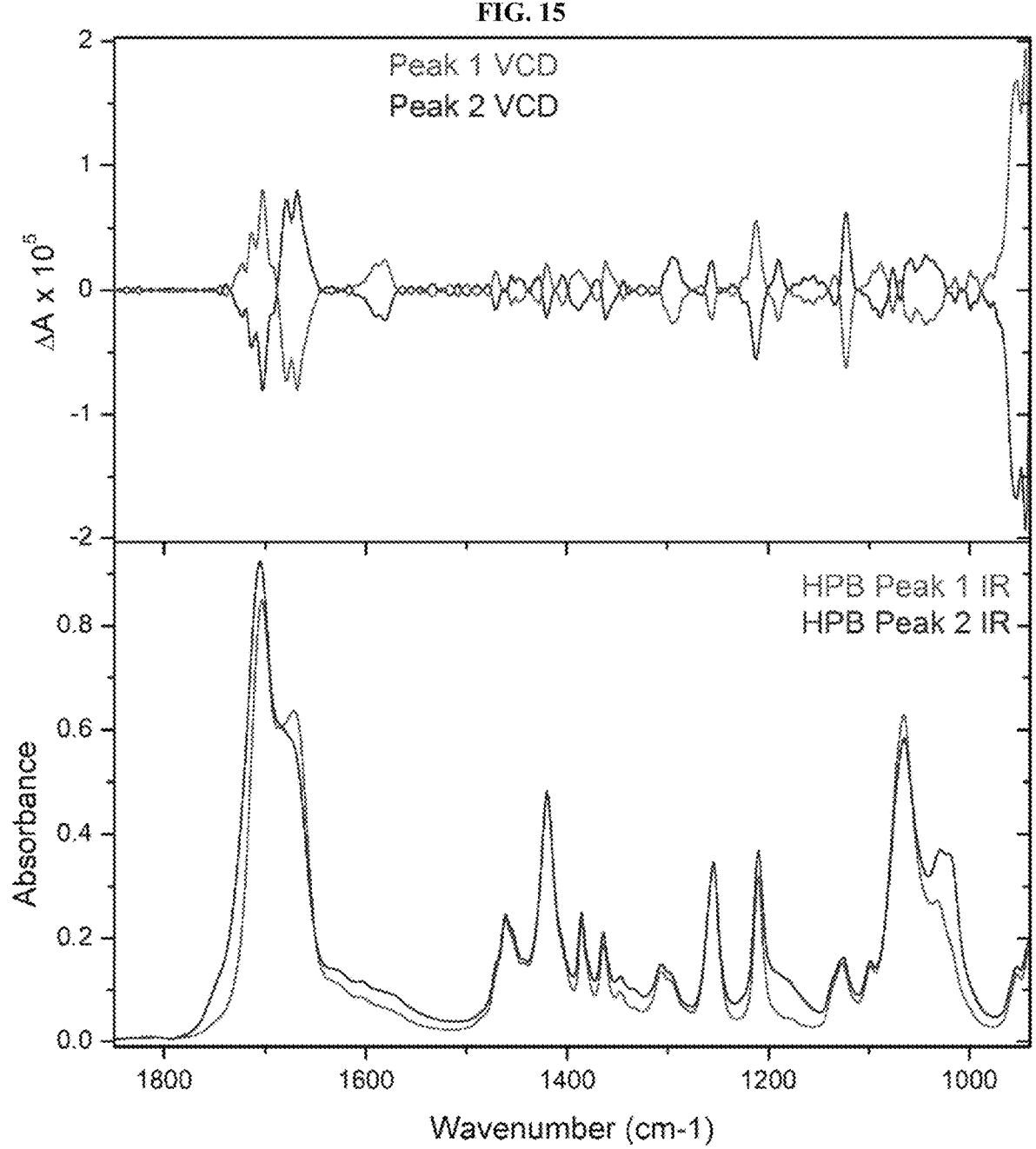
FIG. 15 illustrates the overlay of the experimental infrared spectra (IR) and vibrational circular dichroism (VCD) spectra of enantiomers Example 1-2A (Peak 1) and Example 1-2B (Peak 2).

Vibrational circular dichroism (VCD) is a known and powerful technique used for the identification of absolute configurations of small molecules in solution from VCD spectra since VCD spectra of enantiomers can be simulated using ab initio calculations. As shown in the FIGS. 13 and 14, the IR and VCD spectra of Example 1-2B on the top are consistent with the corresponding theoretically calculated spectra at the bottom with a confidence level of 99%, which confirmed the absolute configuration of Example 1-2B as R configuration. Based on the overlay of IR and VCD spectra of enantiomers Example 1-2A and Example 1-2B, the absolute configuration of Example 1-2A is S configuration.

Example 1-3: 1-((cyclopropylmethyl)sulfide)-N,N-diethylmethanamide (1-3)

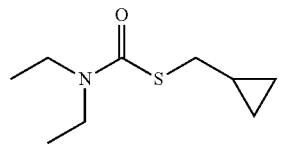

To a stirred solution of cyclopropylmethanethiol (2.0 g, 22.7 mmol) in 25 mL of dry THF cooled in an ice bath under nitrogen was added N,N-diethylcarbamoyl chloride (3.0 mL, 23.8 mmol) was added to the reaction in one portion. To this solution was added DBU (3.6 mL, 23.8 mmol) portionwise. Upon completion of the addition, the reaction was stirred for 1 h before the addition of 50 mL of diethyl ether. The suspension was filtered through 10 g of silica gel eluting with diethyl ether. Concentration provided the product Example 1-3 (4.24 g, 99%) as a colorless oil: $^1$H NMR (400 MHz, CDCl$_3$): δ 3.37 (br s, 4H, 2×CH$_2$), 2.85 (d, J=7.2 Hz, 2H, SCH$_2$), 1.17 (br s, 6H, 2×CH$_3$), 1.0 (m, 1H, CH, cyclopropyl), 0.55 (m, 2H, cyclopropyl), 0.25 (m, 2H, cyclopropyl).

Examples 1-4: 1-((cyclopropylmethyl)sulfinyl)-N,N-diethylmethanamide (1-4)

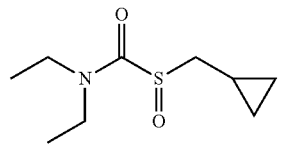

To a stirred solution of 1-((cyclopropylmethyl)sulfide)-N,N-diethylmethanamide 1-3 (4.4 g, 23.5 mmol) in dichloromethane (50 mL) at −10° C. was added a solution of mCPBA (4.7 g, 21.1 mmol) in dichloromethane (50 mL) at a rate not to exceed a temperature of −10° C. After 1 h, the reaction was filtered and concentrated in vacuo. The crude residue was chromatographed (silica gel) eluting with MTBE followed by 20% THF in EtOAc affording 1-((cyclopropylmethyl)sulfinyl)-N,N-diethylmethanamide Example 1-4 as a colorless oil (3.5 g, 74%): $^1$H NMR (400 MHz, CDCl$_3$): δ 3.70-3.40 (m, 4H, 2×CH$_2$), 3.00-2.80 (m, 2H, CH$_2$), 1.28-1.25 (t, J=7.2 Hz, 3H, CH$_3$), 1.22-1.18 (t, J=7.2 Hz, 3H, CH$_3$), 1.12-1.16 (m, 1H, CH cyclopropyl), 0.66-0.70 (m, 2H, CH$_2$ cyclopropyl), 0.32-0.44 (m, 2H, CH$_2$ cyclopropyl); $^{13}$C NMR (100 MHz, CDCl$_3$) 167.7 (CO), 57.44 (CH$_2$), 42.90 (CH$_2$), 40.87 (CH$_2$), 14.6 (CH$_3$), 12.57 (CH$_3$), 5.49 (CH, cyclopropyl); 4.96 (CH$_2$, cyclopropyl), 4.79 (CH$_2$, cyclopropyl); MS: m/e 204.2 (M+1).

Examples 1-4A and 1-4B:enantiomer (−)-1-((cyclopropylmethyl)sulfinyl)-N,N-diethylmethanamide (1-4A) (Peak-1) and enantiomer (+)-1-((cyclopropylmethyl)sulfinyl)-N,N-diethylmethanamide (1-4B) (Peak-2)

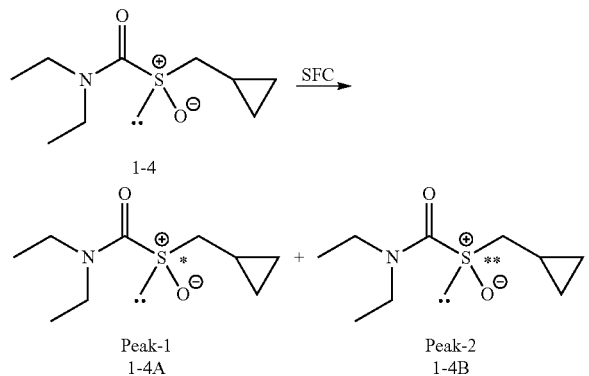

1-((Cyclopropylmethyl)sulfinyl)-N,N-diethylmethanamide (4.717 g) was separated using chiral SFC conditions to give 1-2 enantiomers in different batches.
Example 1-4A: (−)-enantiomer (Peak-1) (34 mg, >99% ee; 700 mg, 99% ee; 937 mg, 98% ee), RT 3.83 min, [α]$^{22}_D$=−53.9° (c=0.0045 g/ml, CHCl$_3$)
Example 1-4B: (+)-enantiomer (Peak-2) (30 mg, >99% ee; 660 mg, >99% ee; 735 mg, >99% ee), RT 4.34 min, [α]$^{22}_D$=+53.6° (c=0.0045 g/ml, CHCl$_3$)
Preparative SFC Conditions:
CHIRALPAK© AS-H (2×25 cm)
15% iso-propanol/CO$_2$, 100 bar
60 mL/min, 220 nm
Injection volume: 0.2 mL, 4 mg/mL in iso-propanol
Analytical SFC Conditions:
CHIRALPAK© AS-H (25×0.46 cm)
15% iso-propanol/CO$_2$, 100 bar
3.0 mL/min, 208, 254, 280 nm Example 1-11:
(4-hydroxypiperidin-1-yl)(methylsulfinyl)methanone Synthesis:

Scheme 5

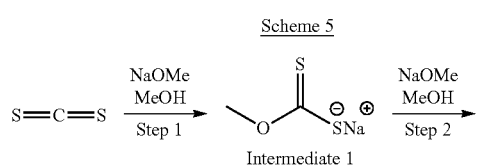

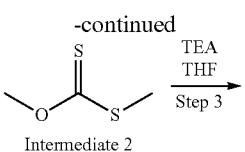

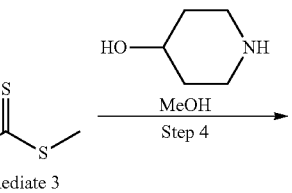

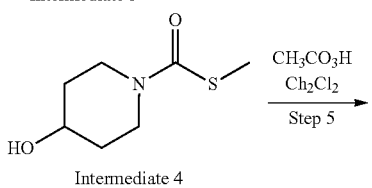

Example 1-11

Example 1-11 was prepared according to the steps as described in Scheme 5.

Step 1: Synthesis of Sodium O-methyl Carbonodithioate (Intermediate 1)

To a 22 L flask was added MeOH (4 L). The MeOH was cooled to −10° C. and 25% sodium methoxide in methanol (4.0 L; 17.5 mol) was added. The solution was kept at −10° C. and carbon disulfide (1.103 L; 18.34 mol) was added slowly as to keep the temperature below 10° C. The reaction mixture was stirred overnight as it slowly warmed to room temperature. The reaction mixture was concentrated under reduced pressure. The resulting green solid was triturated with MTBE (2 L) and the solid was collected via suction filtration. The solid was dried under vacuum overnight to give sodium O-methyl carbonodithioate (Intermediate 1) (2.32 kg; 17.8 mol, assuming quantitative yield) as a green solid which was used as is in the next step. NMR (DMSO-d6): 3.69 ppm (s).

Step 2: Synthesis of S,S-dimethyl Carbonodithioate (Intermediate 2)

To a 12 L flask was added sodium O-methyl carbonodithioate (1090 g, 8.37 mol), ice (500 g), and water (5 L). The flask was cooled to −10° C. (ice/methanol bath) and the solution was stirred rapidly. To the rapidly stirring solution iodomethane (470 mL; 7.55 mol) was added slowly. The reaction mixture was stirred overnight as it slowly warmed to room temperature. Separate the lower yellow layer to give O,S-dimethyl carbonodithioate (Intermediate 2) (749 g, 6.14 mol, 81% yield) which was used in the next step as is. NMR (CDCl$_3$): 4.25 ppm (s, 3H); 2.64 ppm (s, 3H). This Intermediate 2 is volatile and, therefore, it was not dissolved in organic solvent for washing purposes.

Step 3: Synthesis of S,S'-Dimethyl Dithiocarbonate (Intermediate 3)

To a 3 L flask was added O,S-dimethyl carbonodithioate (500 g, 4.09 mol) and THF (1 L). Triethylamine (270 mL)

was added at room temperature. The reaction mixture was slowly heated to 40° C. and the heating mantle was removed (reaction is exothermic). When temperature dropped to 40° C. additional triethylamine (50 mL) was added dropwise. After the exotherm is complete, the resulting mixture was heated to 65° C. for 2 h. Allow the reaction mixture to cool to room temperature overnight. Decant the liquid from the solid. Concentrate the liquid removing the bulk of the THF and triethylamine. Dissolve the liquid residue in MTBE (1 L), wash with brine, and dry over sodium sulfate. Concentrate under reduced pressure to yield Intermediate 3 (412 g; 3.37 mol; 82% yield) as a yellow liquid. NMR ($CDCl_3$): 2.4 ppm (s). Intermediate 3 can be distilled without decomposition.

Step 4: Synthesis of Synthesis of S-Methyl 4-hydroxy-1-piperidinecarbothioate (Intermediate 4)

1027 g (8.42 mol) of S,S'-Dimethyl dithiocarbonate (DMDTC) was combined with 1020 g (10.10 mol) of 4-hydroxypiperidine in 1 L of methanol. A slight stream of nitrogen was introduced to the closed reaction vessel with a line for escaping methyl mercaptan to be bubbled through a solution of commercial bleach (8.25% aqueous sodium hypochlorite). The reaction mixture was stirred at 45° C. for 4 hours; the heat was turned off and the reaction was stirred overnight at room temp. HPLC the next day indicated ca. 90% consumption of DMDTC. The temperature was raised to 45° C. After 4 hours HPLC indicated complete reaction. The methanol was removed by rotary evaporation and the residue was dissolved in 6 L of DCM. The solution was washed with commercial bleach (8.25% aqueous sodium hypochlorite 2 L diluted with 4 L of water). Drying ($Na_2SO_4$) and evaporation yielded an amber oil that was placed on a column of silica gel (1 kg). Elution with THE yielded 1168 g (6.67 mol, 79% yield) of S-Methyl 4-hydroxypiperidine-1-carbothiolate Intermediate 4. HPLC and $^1$H NMR consistent with authentic sample. FTIR (KBr): $cm^{-1}$ 1620 (s, C=O); $^1$H NMR (400 MHz, $CD_3OD$): δ 3.7-4.1 (br s, 2H), 3.8 (m, 1H), 3.2 (m, 2H), 2.3 (s, 3H, S-Me), 1.85 (m, 2H), 1.4 (m, 2H). $^{13}$C NMR (100 MHz, $CD_3OD$): δ 168.1 (CO), 66.27 (CH), 41.98 ($CH_2$), 35.5 ($CH_2$), 11.57 ($SCH_3$). LC-MS: m/e 176.10 (M+H+), 128.2 (M-$SCH_3$).

Step 5: Synthesis of (4-hydroxypiperidin-1-yl)(methylsulfinyl)methanone (Example 1-11)

22.6 g (130 mmol) of S-Methyl 4-hydroxypiperidine-1-carbothioate was dissolved in 500 mL of DCM and placed in a 1 L round bottom flask equipped with a thermowell thermometer and addition funnel. The reaction vessel was placed in a methanol bath and dry ice was added in portions to maintain the temperature between −25° C. and −40° C. A 32% solution of peracetic acid in acetic acid (24 mL; 114 mmol) was added at a rate such that the reaction temperature did not go above −25° C. The reaction was allowed to warm to room temp overnight. HPLC indicated ca. 19% residual starting material. The reaction mixture was transferred to a 1 L round bottomed flask and the DCM was removed on a rotary evaporator. Heptane (200 mL) was added to the residue and evaporated to azeotropically remove acetic acid. (HPLC indicated 14% residual starting material at this point.) The resulting slurry was thoroughly triturated under sonication with 500 mL of MTBE, yielding 45.5 g (81% yield) of (4-hydroxypiperidin-1-yl)(methylsulfinyl)methanone Example 1-11 as a white powder. HPLC indicated 96% purity. FTIR (KBr): $cm^{-1}$ 1696 (s, C=O), 1085 (s, S=O); $^1$H NMR (400 MHz, $CD_3OD$): δ 4.82 (s, 1H, OH), 3.6-3.95 (m, 3H), 3.3-3.5 (m, 1H), 3.25 (m, 1H), 2.64, 2.66 (2s, 3H, S—$CH_3$), 1.85 (m, 2H), 2.5 (m, 2H). $^{13}$C NMR (100 MHz, $CD_3OD$): δ 167.3 (CO), 65.5 (CH), 41.5 ($CH_2$), 35.7 (S—$CH_3$), 33.0 ($CH_2$).

A 5 g sample of Example 1-11 prepared herein was recrystallized from THE (200 mL) yielding 2.6 g of crystalline material. M.P. 128.6-129.6° C. Combustion analysis confirmed the purity of Example 1-11 prepared herein as shown below.

| Combustion analysis | | |
|---|---|---|
| | Calculated | Found |
| C | 43.96 | 44.32 |
| H | 6.85 | 6.88 |
| N | 7.32 | 7.26 |
| S | 16.76 | 16.84 |

Separations of Enantiomers of Example 1-11A and Example 1-11B: (R)-(4-hydroxypiperidin-1-yl)(methylsulfinyl)methanone and (S)-(4-hydroxypiperidin-1-yl)(methylsulfinyl)methanone Racemate of (4-hydroxypiperidin-1-yl)(methylsulfinyl)methanone prepared according to the methods as provided and described herein were separated using chiral SFC conditions to give (R)-(4-hydroxypiperidin-1-yl)(methylsulfinyl)methanone (Example 1-11A, Peak 1) and (S)-(4-hydroxypiperidin-1-yl)(methylsulfinyl)methanone (Example 1-11B, Peak 2).

Figure 8:
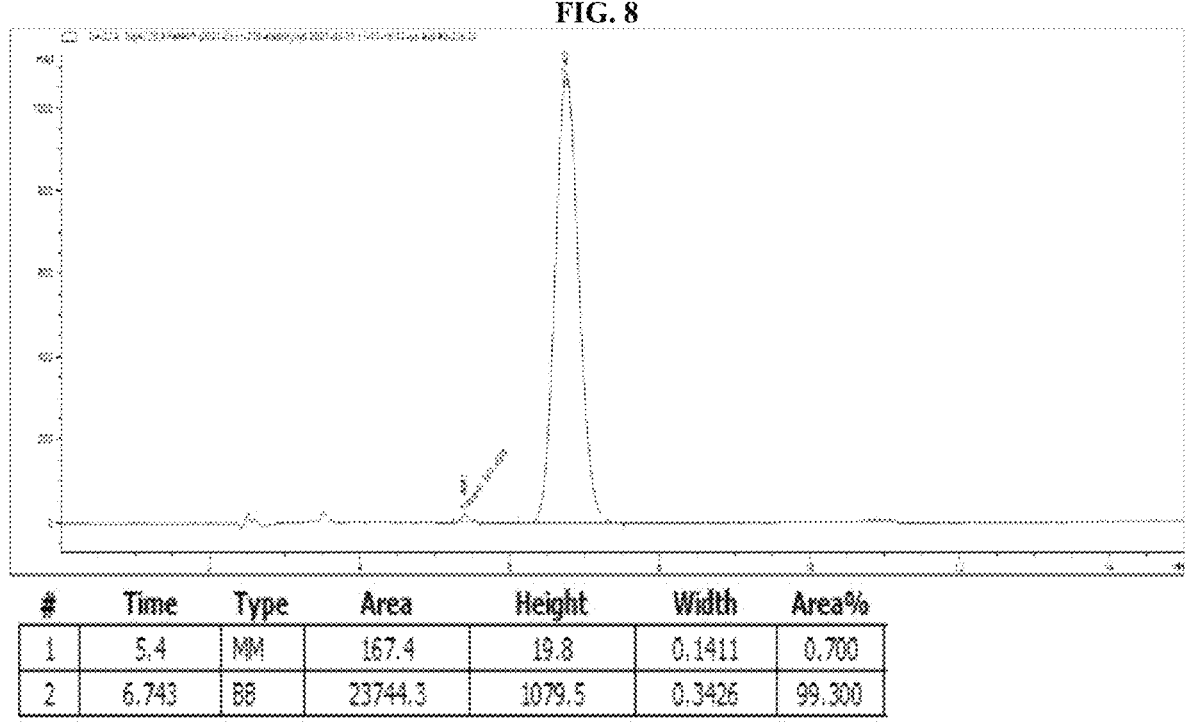
FIG. 8 illustrates the supercritical fluid chromatography (SFC) analysis of the enantiomer Example 1-11B on chiral column.

The preparative SFC method described here was used for the chiral resolution of 30 grams of the racemic mixture, Example 14-11. 13.5 grams of white solid particles of the desired enantiomer, Example 14-11B (Peak2), was obtained using SFC followed by solvent evaporation then lyophilization. To obtain solid particles, the product was freeze-dried in the mixture solvent of methanol, acetonitrile and dioxane at a ratio of 10:20:70 following solvent evaporation of the SFC peak fraction. The purified Example 1-11B was analyzed for enantiomeric excess using the chiral SFC method described herein below. The enantiomeric excess of the final product was determined to be 98.6% (with the enantiomeric ratio of 99.3/0.7) as shown in FIG. 8.

Method development and sample analyses were conducted using Agilent 1200 HPLC and Agilent Aurora-F5 Analytical SFC instruments. Preparative SFC was conducted using a Berger Multigram II SFC equipped with two SD-1 Varian pumps, a Knauer K-2501 Spectrophotometer, a 6-ton bulk CO2 tank with a built-in chiller and heater and G700 compressor. The conditions are as shown below.

Preparative SFC Conditions:
  Instrument: Berger Multigram II SFC
  Column: (R,R) Whelk-O 1 5 µm (2.1×25 cm), Regis Technologies, Inc.
  Temperature: 40° C.
  Mobile Phase: 15% (95% MeOH with 5% dichloromethane)/CO2
  Flow rate: 60 mL/min
  Injection volume: 1.6 mL of ∼'30 mg/mL solution in MeOH, with stacked injections
  Detection: 220 nm
  Backpressure: 100 bar Sample preparation: Dissolve the original solid material in methanol at ~'30 mg/mL, filter the solution with 0.2 μm Nylon membrane filter.

Figure 9:
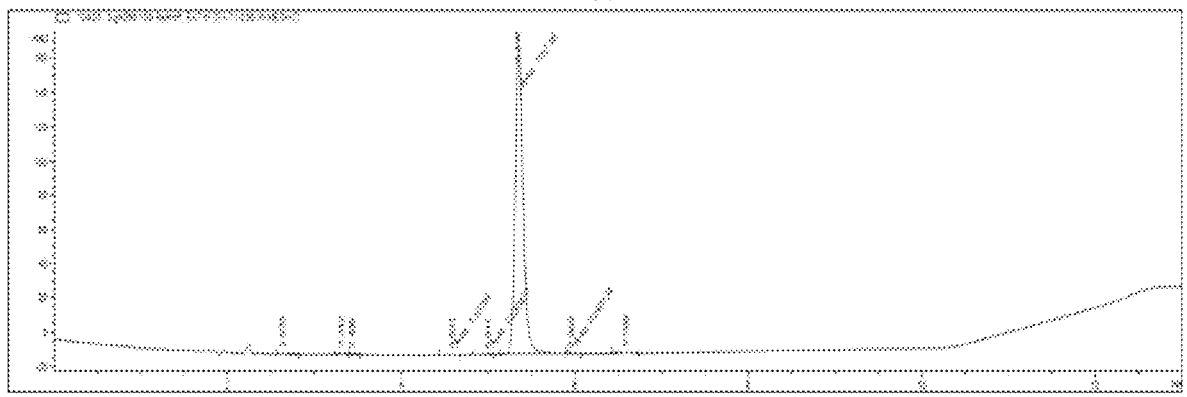
FIG. 9 illustrates the high-performance liquid chromatography (HPLC) analysis of the enantiomer Example 1-11B on chiral column.

Analytical SFC Conditions:
  Instrument: Agilent Aurora Analytical SFC
  Column: CHIRALPAK® IG 5p m (0.46×25 cm), Chiral Technologies, Inc.
  Temperature: Ambient
  Mobile Phase: 50% MeOH/CO2
  Flow rate: 2 mL/min
  Backpressure: 100 bar
  Detection: 220 nm
  Injection volume: 10 uL of ~'2 mg/mL solution of 1:1 MeOH/MeCN Analytical HPLC:
  Instrument: Agilent 1200 HPLC/UV/MS
  Column: Cogent UDC-Cholesterol, 4.6×150 mm 5 μm, MicroSolv Technology
  Temperature: Ambient (22° C.)
  Mobile Phase gradient: 0 min: 95% acetonitrile; 5% 0.1% acetic acid in water 8 min: 83% acetonitrile; 17% 0.1% acetic acid in water 10 min: 60% acetonitrile; 40% 0.1% acetic acid in water 12 min: 60% acetonitrile; 40% 0.1% acetic acid in water Equilibration time at the initial composition: 5 min
  Injection volume: 2 uL of ~'2 mg/mL solution of 1:1 MeOH/MeCN
  Flow rate: 1 mL/min
  Detection: 250 nm with a bandwidth of 100 nm Example 1-11B was analyzed for achiral chemical purity using the aqueous normal phase HPLC method described in the Experimental section. As shown in FIG. 9, the achiral chemical purity was determined to be 99.1% with no single impurity greater than 0.4% based on HPLC/UV peak area percent at 200-300 nm wavelength range.

Determination of the Absolute Configuration of Example 1-11B

The absolute configuration of Example 1-11B were determined to have a represented formula of

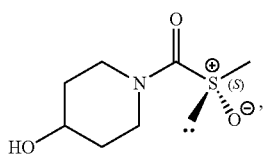

wherein the chirality of the Sulfur is (S) based on Vibrational circular dichroism (VCD) analysis. The conditions and procedures for the VCD analysis are described herein.

| GENERAL INFORMATION | |
| --- | --- |
| VCD-spectrometer | ChiralIR w/DualPEM |
| RESULTS | |
| Absolute Configuration of Example 1-11B is (S) | Confidence Level: 99%* |
| MEASUREMENT PARAMETERS | |
| Concentration | 9 mg/150 uL |
| Solvent | CDCl3 |
| Resolution | 4 cm$^{-1}$ |
| PEM setting | 1400 cm$^{-1}$ |
| Number of scans/ Measurement time | 24 hours enantiomer and racemic |
| Sample cell | BaF2 |
| Path length | 100 μm |
| CALCULATION DETAILS | |
| Molecular Mechanics Force Field | MMFF94 (Compute VOA) |
| DFT Software version | Gaussian '09 |
| Number of conformers used for Boltzmann sum | 12 (cc-pVQZ)/B3PW91) |
| Methodology and basis sets for DFT calculations | 6-31Gd, cc-pVTZ, cc-pVQZ/B3LYP, B3PW91/CPCM (cdcl3) |
| Enantiomer used for calculation | S |
| Total calculated conformers | 78 (6-31Gd)/24 (cc-pVTZ)/24 QZ |
| Number of low-energy conformations shown in report | 4 |

*The confidence level is a measure of the degree of congruence between a calculated and measured spectrum. It's a measure of quality or degree of agreement between calculated and measured spectra. If identical spectra are being compared, the confidence level is 100%.

Figure 10:
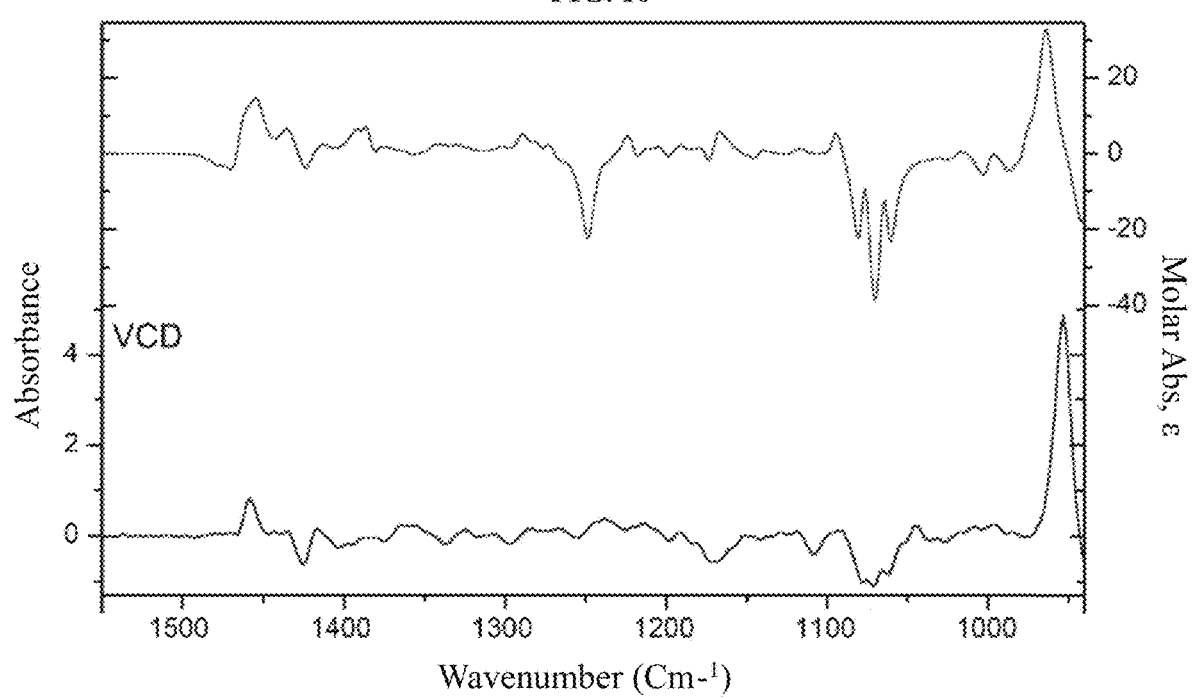
FIG. 10 illustrates the comparison of the experimental and theoretically calculated infrared spectra (IR) spectra of the enantiomer Example 1-11B.
Figure 11:
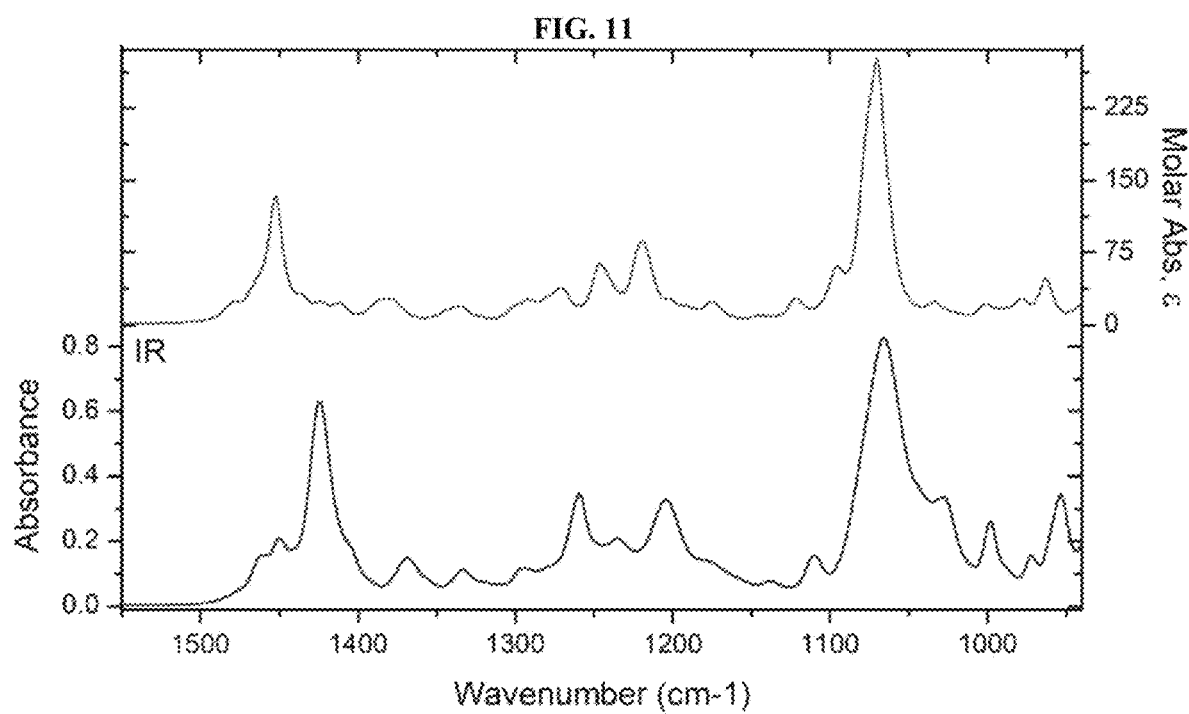
FIG. 11 illustrates the comparison of the experimental and theoretically calculated vibrational circular dichroism (VCD) spectra of the enantiomer Example 1-11B.

Vibrational circular dichroism (VCD) is a known and powerful technique used for the identification of absolute configurations of small molecules in solution from VCD spectra since VCD spectra of enantiomers can be simulated using ab initio calculations. As shown in the FIGS. 10 and 11, the IR and VCD spectra of Example 1-11B on the top are consistent with the corresponding theoretically calculated spectra at the bottom with a confidence level of 99%, which confirmed the absolute configuration of Example 1-11B as S configuration.

Optical Rotation of the Absolute Configuration of Example 1-11A and Example 1-11B The specific optical rotations of the enantiomers of Example 1-11A and Example 1-11B were determined, and the average specific rotations in chloroform are $[\alpha]^{22}_D=-13.2°$ (c=0.930, CHCl$_3$) for Example 1-11B, and $[\alpha]^{22}_D=+13.4°$ (c=1.00, CHCl$_3$) for Example 1-11A. 93.0 mg of the Example 1-11A and 100 mg of Example 1-11B were weighed and dissolved respectively in 10 mL chloroform. The solutions were transferred to a 100-mm cell. Ten specific rotation measurements were taken at ten-second intervals to obtain an average. The experiment was repeated three times, and the grand average was reported for both enantiomers.

Solubility of the Absolute Configuration of Example 1-11B

The solubility in chloroform (CHCl$_3$), dichloromethane (DCM) and dimethyl sulfoxide (DMSO) was determined at room temperature up to 50 mg/mL by measuring the concentrations of the solutions using SFC/UV. The solubility of Example 1-11B was found to be 12.4 mg/mL in CHCl$_3$, 12.3 mg/mL in DCM, and >50 mg/mL in DMSO. 200 mg Example 1-11B was weighed individually into three separate vials. 4 mL DMSO, 6 mL CHCl$_3$ and 6 mL DCM were pipetted into the three vials containing Example 1-11B. The solutions were mixed and sonicated for 10 minutes. The DMSO solution was clear, and an aliquot was taken and diluted 100 times using MeOH before being subjected to SFC analysis. The saturated CHCl$_3$ and DCM solutions were centrifuged, and the clear solution was diluted 100 times using MeOH before being subjected to SFC analysis:

Analytical SFC Conditions
  Instrument: Agilent Aurora SFC system
  Column: Chialpak IG (4.6×250 cm)
  Temperature: Ambient (22 □C)
  Mobile Phase: 50% MeOH/50% CO2, (100 bar)
  Flow rate: 2 mL/min
  Injection volume: 15 μL of 2 mg/mL solutions
  Detection: 220 nm Solubility measurement of up to 50 mg/mL in DMSO, CHCl3 and DCM was requested. In DMSO, Example 1-11B was found to be completely soluble at 50.0 mg/mL. At 50 mg/mL, Example 1-11B was not completely dissolved in CHCl$_3$ or DCM solutions. After mixing and sonication, a clear aliquot of each solution was taken, and the concentrations of Example 1-11B in CHCl$_3$ and DCM were measured by SFC/UV using the DMSO solution as a reference. The solubility of Example 1-11B was determined to be 12.4 mg/mL in CHCl3, 12.3 mg/mL in DCM, and >50 mg/mL in DMSO.

Example 1-15: 1,1'-(ethane-1,2-diyldisulfinyl)bis(N,N-diethylmethanamide)

Step 1: S,S'-ethane-1,2-diyl bis(diethylcarbamothioate)

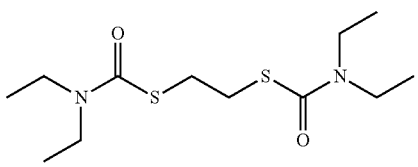 [SMILES: CCN(CC)C(=O)SCCSC(=O)N(CC)CC]

To a stirred solution of 1,2-ethanedithiol (5 mL, 59.5 mmol) and triethyl amine (17 mL, 122 mmol) in THF (50 mL) was added N,N-diethyl carbamoyl chloride (15.5 mL, 122 mmol) at room temperature. The resulting mixture was stirred at room temperature overnight, and the progress of the reaction was monitored by $^1$H NMR analysis. $^1$H NMR of the crude reaction mixture indicated complete consumption of ethane dithiol. The reaction mixture was partitioned between EtOAc (200 mL) and H$_2$O (200 mL). The aqueous layer was separated, and organic layer was concentrated on a rotary evaporator to obtain yellowish residue. To this residue was added Et$_2$O and placed in the refrigerator. The resulting precipitate was filtered to obtain 6.6 g (38% yield) of S,S'-ethane-1,2-diyl bis(diethylcarbamothioate) as a white crystalline solid. TLC: R$_f$ 0.1 (DCM); FTIR (KBr): cm$^{-1}$ 1646 (s, C=O); $^1$H NMR (400 MHz, CDCl$_3$): δ 3.37 (br s, 8H, 4×CH$_2$), 3.1 (s, 4H, 2×SCH$_2$), 1.15 (br s, 12H, 4×CH$_3$); $^{13}$C NMR (100 MHz, CDCl$_3$): δ 166.5 (CO), 42.2 (CH$_2$), 41.8 (CH$_2$), 30.8 (SCH$_2$) 13.7 (CH$_3$), 13.2 (CH$_3$).

Step 2: 1,1'-(ethane-1,2-diyldisulfinyl)bis(N,N-diethylmethanamide)

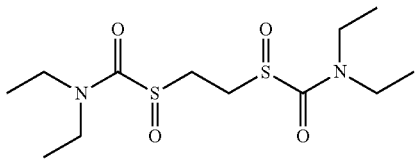 [SMILES: CCN(CC)C(=O)S(=O)CCS(=O)C(=O)N(CC)CC]

250 mL 3-neck flask equipped with thermocouple, magnetic stir bar, N$_2$ inlet and dropping funnel was charged with S,S'-ethane-1,2-diyl bis(diethylcarbamothioate) (4.0 g, 13.7 mmol) and DCM (40 mL). The resulting solution was stirred and cooled to −19° C. in a water ice-MeOH bath. A solution of mCPBA (6.3 g, 77% concentration, 27.4 mmol) in DCM (50 mL) provided a biphasic solution. The small upper layer (water present in commercial mCPBA) was discarded, and the lower layer was added dropwise over 20 min to the solution of S,S'-ethane-1,2-diyl bis(diethylcarbamothioate) while maintaining the internal temperature between −10 to −20° C. The reaction was complete upon complete addition of mCPBA as evidenced by TLC. The resulting slurry was diluted 1:1 with heptane (90 mL), stirred for 30 min at room temperature, and filtered to remove the byproduct m-chlorobenzoic acid. The clear filtrate was concentrated by rotary evaporation at 22° C. bath temperature to give a white solid, which was stirred vigorously with MTBE (125 mL) until fully liquefied. The upper phase was decanted from a small amount of viscous oily material, filtered immediately through a cotton plug to give a clear solution, stirred until crystals appeared, and cooled in an ice bath to 2° C. internal temperature over 45 min. The crystalline solid was filtered under N$_2$, washed with pre-chilled (~−20° C.) MTBE (2×15 mL) and dried under vacuum to afford 1.2 g (28% yield) of compound 1,1'-(ethane-1,2-diyldisulfinyl)bis(N,N-diethylmethanamide) Example 1-15 as a colorless crystalline powder as a mixture of diastereomers, mp 71.2-74.5° C. TLC: R$_f$ 0.1 (1:1 EtOAc/THF), 0.5 (5% MeOH/DCM); FTIR (KBr): cm$^{-1}$ 1699 (s, C=O), 1041 (s, S=O); $^1$H NMR (400 MHz, CDCl$_3$): δ 3.58-3.21 (m, 12H, 6×CH$_2$), 1.31-1.19 (m, 12H, 4×CH$_3$); $^{13}$C NMR (100 MHz, CDCl$_3$): δ 166.8 (CO), 166.7 (CO), 43.14 (CH$_2$), 43.12 (CH$_2$), 43.1 (CH$_2$), 42.6 (CH$_2$), 41.3 (CH$_2$), 41.3 (CH$_2$), 14.6 (d, CH$_3$), 14.5 (d, CH$_3$), 12.8 (s, CH$_3$), 12.78 (s, CH$_3$); HPLC-MS: m/e 347.5 (M+Na$^+$).

Example 1-16: 1,1'-(2,2-dimethylpropane-1,3-diyldisulfinyl)bis(N,N-diethylmethanamide)

Step 1: S,S'-(2,2-dimethylpropane-1,3-diyl)bis(diethylcarbamothioate)

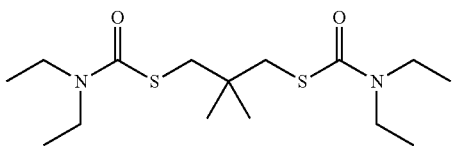 [SMILES: CCN(CC)C(=O)SCC(C)(C)CSC(=O)N(CC)CC]

The 2-(2,2-dimethyl)-1,3-propanedithiol (E. L. Eliel et al, J. Org. Chem. 1975, 40, 524) (2.6 g, 223.7 mmol) was dissolved in dry THF (25 mL) and the reaction was placed in an ice bath. N,N-diethyl carbamoyl chloride (6.16 mL, 2.05 equiv) was added to the reaction mixture, followed by dropwise addition of DBU (7.25 mL, 2.05 eqiuv). An almost immediate formation of a white solid was observed. The reaction mixture was stirred for 2 h at room temperature; the solvent was removed in vacuo; the residue was suspended in diethyl ether (150 mL) and washed with water. Drying and evaporation yielded 7.4 g (100% yield) of crude S,S'-(2,2-dimethylpropane-1,3-diyl)bis(diethylcarbamothioate) which was used in the next step without further purification. FTIR (KBr): cm$^{-1}$ 1650 (s, C=O); $^1$H NMR (400 MHz, CDCl$_3$): δ 3.4 (t, J=6.8 Hz, 8H), 3.03 (s, 4H), 1.1-1.3 (br s, 12H), 1.03 (s, 6H). $^{13}$C NMR (100 MHz, CDCl$_3$): δ 167.0 (CO), 44.2, 41.2, 35.5, 25.9, 13.8. The cited reference herein is incorporated by reference in its entirety.

Step 2: 1,1'-(2,2-dimethylpropane-1,3-diyldisulfinyl)bis(N,N-diethylmethanamide)

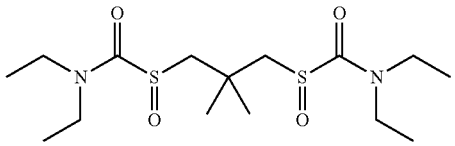 [SMILES: CCN(CC)C(=O)S(=O)CC(C)(C)CS(=O)C(=O)N(CC)CC]

S,S'-(2,2-dimethylpropane-1,3-diyl)bis(diethylcarbamothioate) (3.9 g, 12.75 mmol) was dissolved in 25 mL of dry DCM and the flask was placed in an ice/methanol bath. Resulting solution was stirred and cooled to −10° C. To this mixture was added a solution of mCPBA (5.14 g, 1.8 equiv; 0.9 equiv per sulfide) in DCM (50 mL) and added at a rate to maintain the reaction temperature below −10° C. After addition was complete (ca. 1 h) the bath was removed, the insoluble benzoic acid byproduct was filtered off and the filtrate was concentrated in vacuo. The crude product was chromatographed on a Teledyne ISCO CombiFlash Rf yielding 1.7 g (39.8%) of the product as a mixture of diastereomers. FTIR (KBr): cm$^{-1}$ 1700 (s, C=O), 1070 (s, S=O); $^1$H NMR (400 MHz CDCl$_3$): δ 3.52-3.40 (m, 8H, NCH$_2$CH$_3$), 3.23 (d, J=13.6 Hz; 1H of CH$_2$S), 3.07 (s, 2H, CH$_2$S), 2.96 (d, J=13.6 Hz; 1H of CH$_2$S), 1.46 (s, 3H, gem dimethyl), 1.42 (s, 3H, gem dimethyl), 1.27-1.18 (m, 12H, NCH$_2$CH$_3$). $^{13}$C NMR (100 MHz, CDCl$_3$): δ 167.9 (CO), 167.8 (CO), 63.5, 62.0, 43.1, 43.0, 41.2, 41.0, 35.6, 35.5, 29.1, 28.4, 27.9, 14.5, 14.47, 12.7, 12.65.

In some embodiments, the methods and synthesis as described here are expected to prepare the compound having a formula of Ho

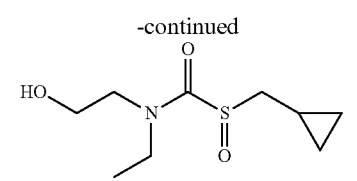

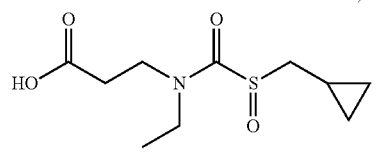

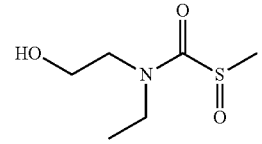

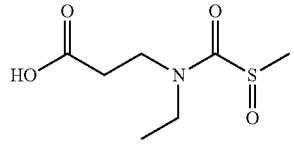

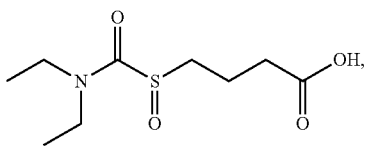

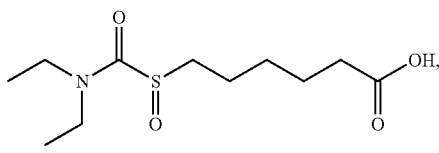

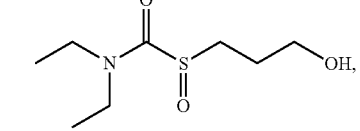

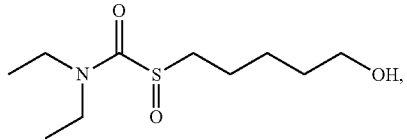

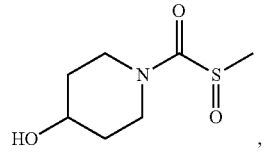

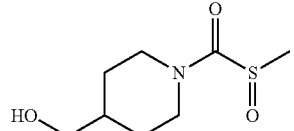

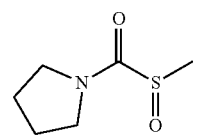

-continued
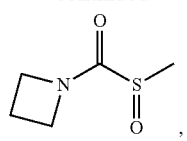,
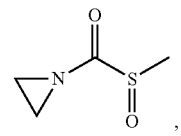,
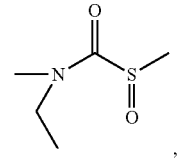,
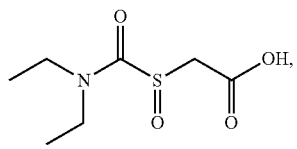,
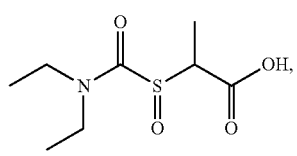,
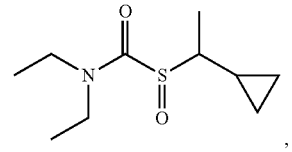,
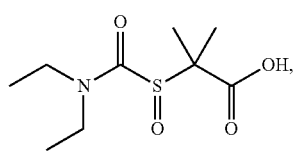,
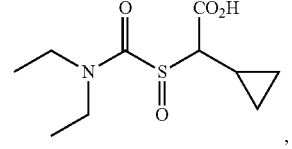,
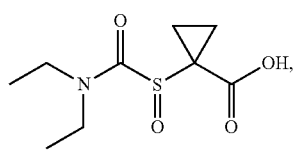,
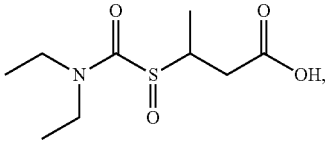,
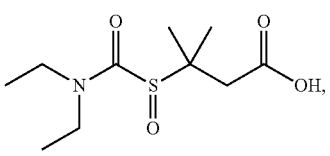,
-continued
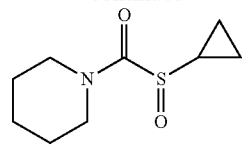,
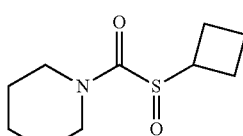,
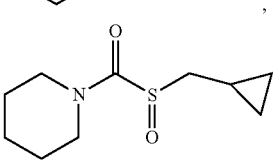,
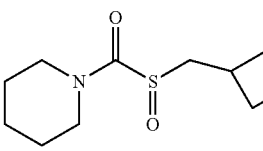,
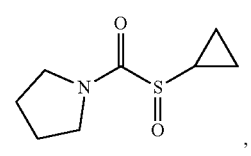,
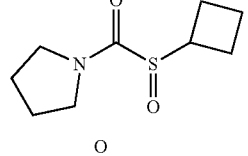,
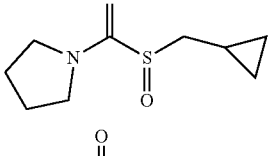,
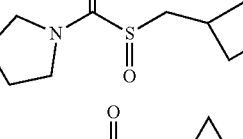,
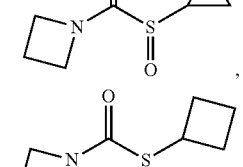,
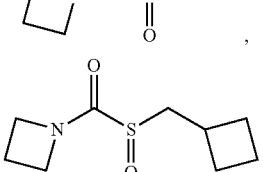,
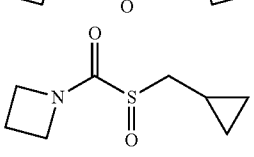, -continued

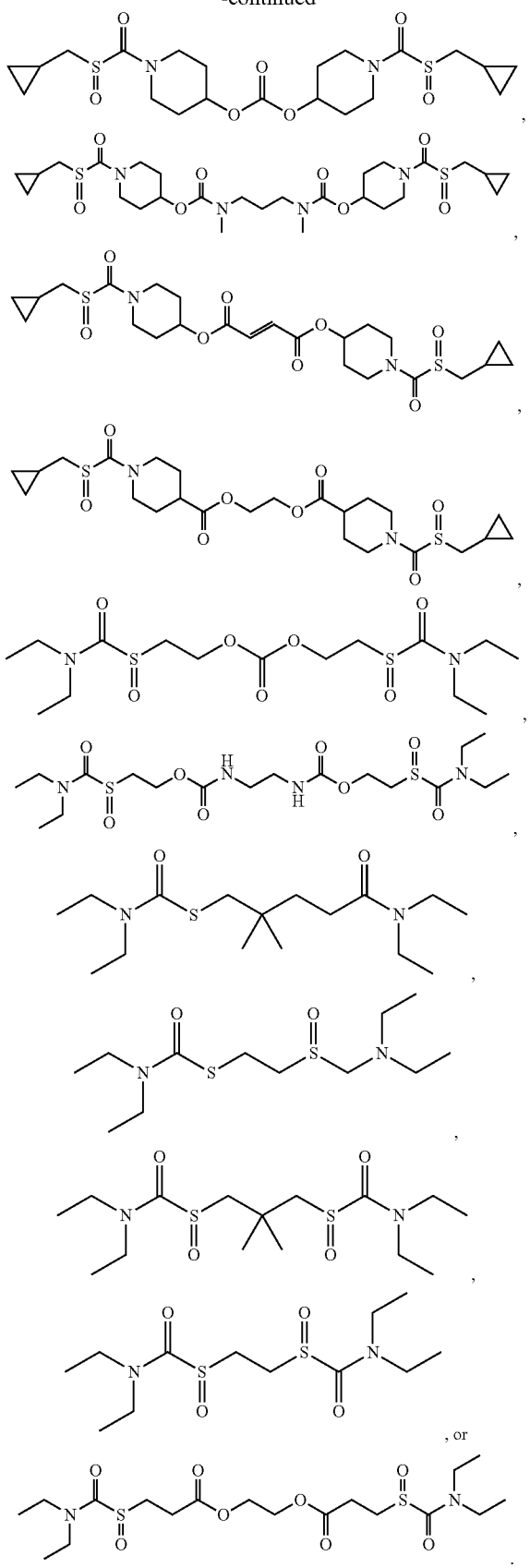

Biological Assays

Disulfiram (Antabuse©) was approved in 1949 for the treatment of alcoholism. Disulfiram works by permanently inhibiting the liver mitochondrial enzyme ALDH2, thus preventing the metabolism of acetaldehyde. The increased systemic concentrations of acetaldehyde, a toxic metabolite of ethanol, cause unpleasant symptoms, such as nausea and flushing of the skin. The anticipation of these effects can help some people avoid drinking alcohol while taking disulfiram.

Ethanol metabolism and the mechanism of action of Disulfiram, and its active metabolite, Example 1-2, as well as the proposed analogues are depicted below and as shown in FIG. 1.

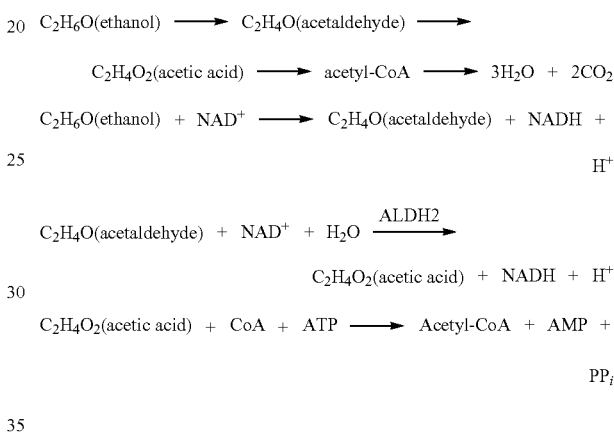

Example 2: In Vivo ALDH2 Enzymatic Activity Assay with Examples 1-2 and Example 1-15

Example 1-2 and Example 1-15 were tested on ALDH2 enzymatic activity assay following the protocol as described herein.

Materials and Methods Sixty (60) male and sixty (60) female Sprague Dawley (CD-IGS) were obtained from Charles River Laboratories. All animals were housed under controlled conditions of temperature (72±8° F.), relative humidity (30-70%) and a 12-hour light-dark cycle (light from 6:00 AM to 6:00 PM). All animals were allowed free access to standard rodent chow (PicoLab Rodent Diet 20) and water (reverse osmosis, 0.2 μM filtered). Animals had at least a 3-day acclimation period prior to study.

Example 1-2 was synthesized by PharmAgra Labs, Lot #489PAL97; and stored at 4° C. and protected from light upon receipt. Example 1-2 dosing solutions were prepared by dissolving in PBS (pH 7.0) and thoroughly mixing via vortexing and sonication.

Example 1-15 was synthesized by PharmAgra Labs, Lot #505PAL17; and stored at 4° C. and protected from light upon receipt. Example 1-15 dosing solution was prepared by dissolving in PBS (pH 7.0) and thoroughly mixing via vortexing and sonication. The dosing formulation at concentration of 20 mg/mL was a clear solution.

Ethanol challenge study design and dosing groups of Example 1-2 and Example 1-15 are as shown in Table 2.

Blood samples were centrifuged at 2,000 g (4,400 rpm, Eppendorf 5417R) for 10 minutes at room temperature.

TABLE 2

| Group # | Test Article | Dose (mg/kg) | Dose Concentration (mg/mL) | Dose Volume (mL/kg) | Dosing Schedule | Sample Size |
|---|---|---|---|---|---|---|
| 1 | Vehicle | N/A | N/A | 1 | QD, 1 Day | 4M/4F |
| 2 | Example 1-2 | 2 | 2 | 1 | | 4M/4F |
| 3 | | 6.5 | 6.5 | 1 | | 4M/4F |
| 4 | | 12 | 20 | 0.6 | | 4M/4F |
| 5 | Vehicle | N/A | N/A | 1 | QD, 3 Days | 4M/4F |
| 6 | Example 1-2 | 2 | 2 | 1 | | 4M/4F |
| 7 | | 6.5 | 6.5 | 1 | | 4M/4F |
| 8 | | 12 | 20 | 0.6 | | 4M/4F |
| 9 | Vehicle | N/A | N/A | 1 | QD, 5 Days | 4M/4F |
| 10 | Example 1-2 | 2 | 2 | 1 | | 4M/4F |
| 11 | | 6.5 | 6.5 | 1 | | 4M/4F |
| 12 | | 12 | 20 | 0.6 | | 4M/4F |
| 13 | Example 1-15 | 20 (Day 1) 12 (Days 2-5) | 20 or 12 | 1 or 0.6 | | 4M/4F |

QD: once per day

General Procedures

Body weights of the animals in Groups 1-4 were obtained on Day 1. Body weights of the animals in Groups 5-8 were obtained on Days 1-3 respectively. Body weights of the animals in Groups 9-13 were obtained on Days 1, 4 and 5 respectively.

Animals were respectively administered vehicle and Example 1-2 at dosages of 2, 6.5 or 12 mg/kg via tail vein injection, once daily for 1 day (Groups 1-4), once daily for 3 days (Groups 5-8), or once daily for 5 days (Groups 9-12). For Group 13, animals were administered 20 mg/kg (on Day 1) or 12 mg/kg (on Days 2-5) dose via tail vein injection, once daily for 5 days. In some studies, the animals were administered a compound described herein for 10 days. In some studies, the animals were administered a compound described herein for 12 days. In some studies, the study was carried out with administered the compounds described herein including Example 1-2 racemate, Example 1-2A, Example 1-21B, Example 1-11 racemate, Example 1-11A, and/or Example 1-11B at a dosage of about 0.5, 1, 2, 4, and 8 mg.

Dosing volume (1 or 0.6 mL/kg) was calculated based on the body weight of the individual animal obtained on Day 1 (all groups), Days 2-3 (Groups 5-8), and Days 4-5 (Groups 9-13).

Ethanol Challenge

Ethanol (200 PRF or 100% pure, non-denatured and no additives) was obtained from Fisher Scientific. The ethanol dosing solution was prepared fresh for each use. One (1) mL of ethanol was added to four (4) mL of saline (0.9% NaCl) in a glass vial and mixed by vortexing to create a uniform solution prior to administration. Animals were administered 20% ethanol at 1 g/kg (IP) 8 hours following the last dose of test article. Thirty (30) minutes following ethanol challenge, animals were euthanized with $CO_2$. About 7 mL of whole blood was rapidly collected via vena cava for generation of serum samples for assays (Acetaldehyde assay by GPL and ALDH2 activity and protein assay by Eurofins). Blood samples were placed into serum separator tubes and maintained at room temperature for at least 30 minutes to allow clot formation prior to processing.

The left lateral lobe of liver was harvested and rinsed in cold saline to render a sample that was snap frozen in liquid nitrogen. Samples were stored at −80° C. until shipment.

Each serum sample was divided into 3 aliquots (1 mL/aliquot) and transferred to Eppendorf micro-tubes. Samples were stored at −80° C. until analysis or shipment.

Enzyme Assays

The obtained serum samples as described herein were measured in singlicate for Acetaldehyde concentration using the Acetaldehyde Colorimetric Assay Kit (BioAssay Systems, #EACT-100), in accordance with manufacturer's instructions.

Figure 2:
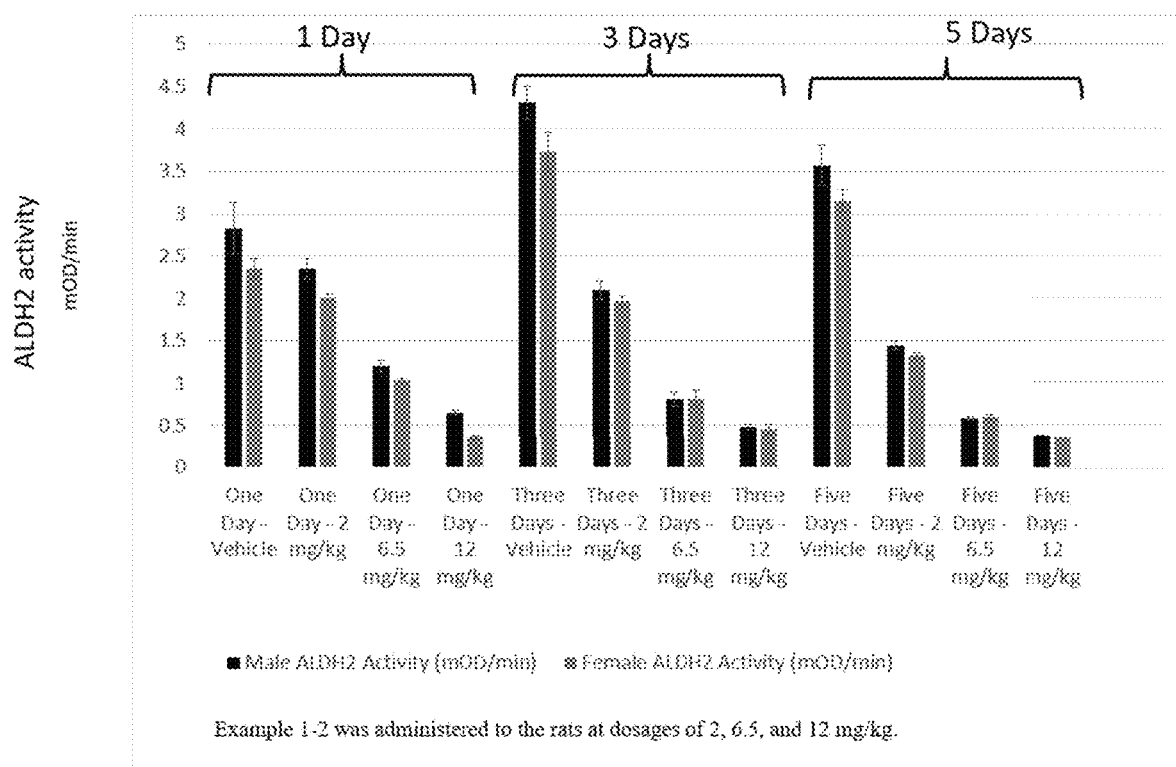
FIG. 2 illustrates the effect of Example 1-2 on liver ALDH2 activities of the rats following ethanol challenge based on treatment durations.

Liver lysate generation, protein concentration determination and assays for measurements of serum and liver ALDH2 protein (ELISA, MyBioSource, #MBS700110) and activity (Enzyme Capture, Abcam, #AB115348) levels were performed by Eurofins Panlabs, Inc. The results are shown in FIG. 2.

Results and Discussion

Figure 3:
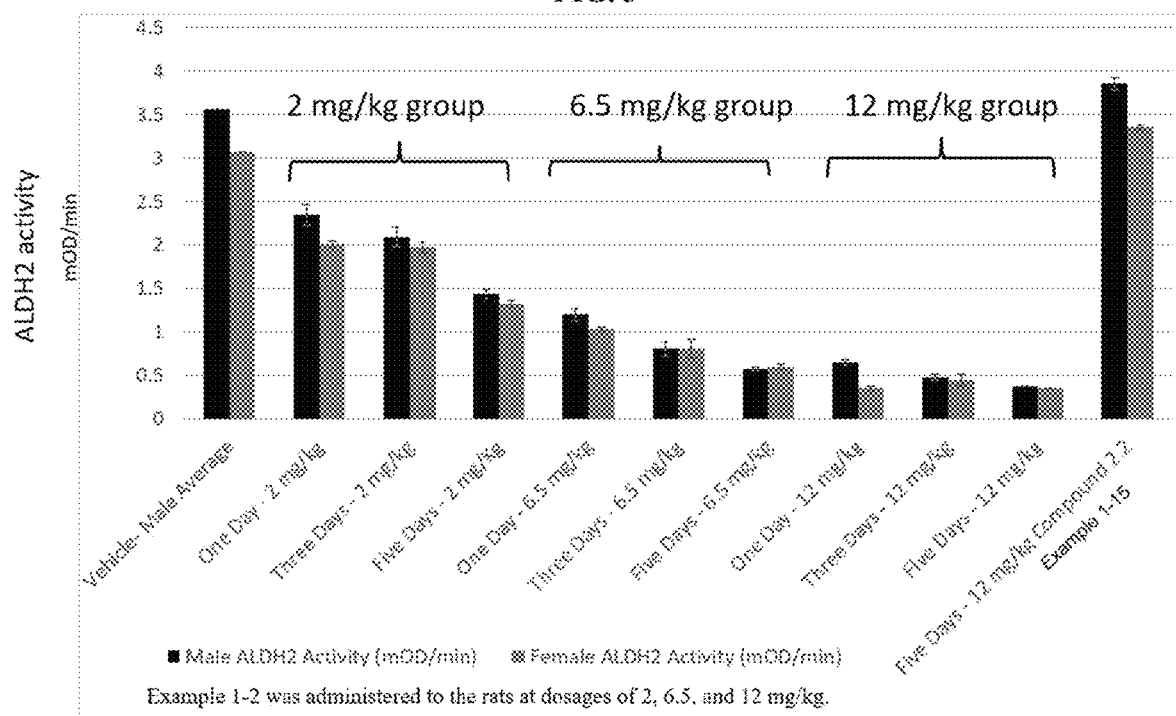
FIG. 3 illustrates the effect of Example 1-2 and Example 1-15 on liver ALDH2 activities of the rats following ethanol challenge based on treatment dosage levels.

A dose response and a treatment-duration response were observed for Example 1-2 in inhibiting ALDH2 activities, while Example 1-15 did not show any inhibition activity in comparison with the negative control group. As shown in FIGS. 2 and 3, Example 1-2 demonstrated statistically significant effectiveness in inhibiting liver ALDH2 activity at dosages of 2 mg/kg, 6.5 mg/kg, and 12 mg/kg. Example 1-2 demonstrated statistically significant ALDH2 inhibitions at all doses when given treatment for 3 and 5 days. Surprisingly and unexpectedly, statistically significant ALDH2 inhibitions were observed after only one (1) day administration for the 6.5 mg/kg and the 12 mg/kg.

Figure 12:
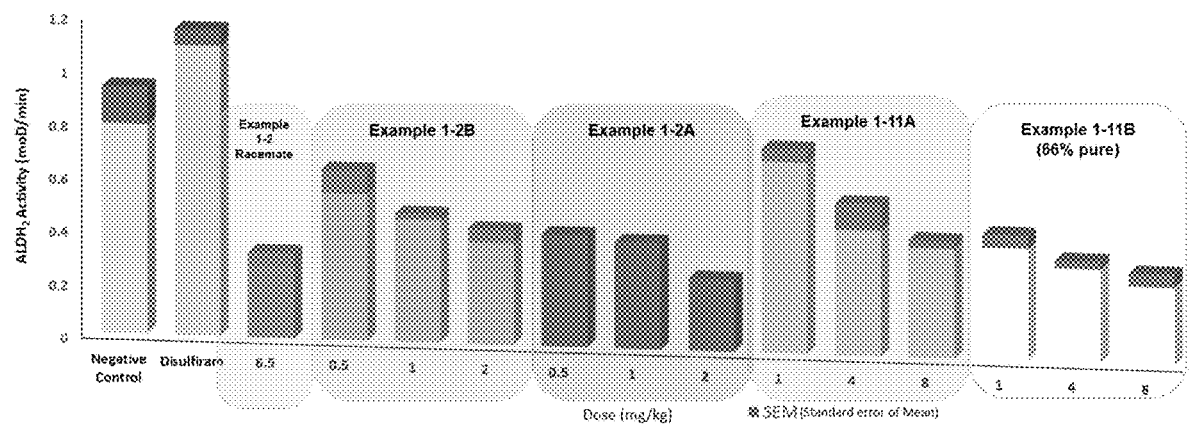
FIG. 12 illustrates the effect of Example 1-2, Example 1-2A, Example 1-2B, Example 1-11A, and Example 1-11B on liver ALDH2 activities of the rats following ethanol challenge based on treatment durations.

The results of the 10-day rat Pharmacology study carried out according to the general procedures described herein are shown in FIG. 12. Surprisingly and unexpectedly, the enantiomer Example 1-2A (Peak-1) showed a greater ALDH2 inhibition compared the other enantiomer Example 1-2B (Peak-2) after 10-day administration at the dosages of 0.5, 1, and 2 mg/kg. Additionally, the 2 mg/kg dosage of the enantiomer Example 1-2A (Peak-1) showed a similar or greater ALDH2 inhibition than that of the racemate Example 1-2 at 6.5 mg/kg for the 10-day administration. Also surprising and unexpectedly, the Example 1-11 racemate with 66 wt % of the enantiomer Example 1-11B showed a greater ALDH2 inhibition than the pure enantiomer Example 1-11A after 10 day administration at the dosages of 2, 4, and 8 mg/kg.

Example 3: In Vivo ALDH2 Enzymatic Activity Assay with Disulfiram and Examples 1-2, Example 1-4A, and Example 1-4B Examples 1-2, Example 1-4A, and Example 1-4B and disulfiram were tested on ALDH2 enzymatic activity assay following the protocol as described herein.

Materials and Methods

Eighty-eight (88) male Sprague Dawley (CD-IGS) were obtained from Charles River Laboratories. All animals were housed under controlled conditions of temperature (72±8° F.), relative humidity (30-70%) and a 12-hour light-dark cycle (light from 6:00 AM to 6:00 PM). All animals were allowed free access to standard rodent chow (PicoLab Rodent Diet 20) and water (reverse osmosis, 0.2 μM filtered). Animals had at least a 3-day acclimation period prior to study.

30 mL disulfiram formulation were prepared. 64.2 mg of disulfiram was completely dissolved in 6 mL of DMSO to render a mixture. 0.3 mL of Tween 80 was then slowly added to the mixture. To the resulting mixture, 23.7 mL of PBS (lx, pH 5.0) was slowly added while stirring to render a dosing formulation. The dosing formulation was a fine suspension at concentration of 2.14 mg/mL. The final concentrations for DMSO and Tween 90 were 20% v/v and 1% v/v, respectively.

Figure 4:
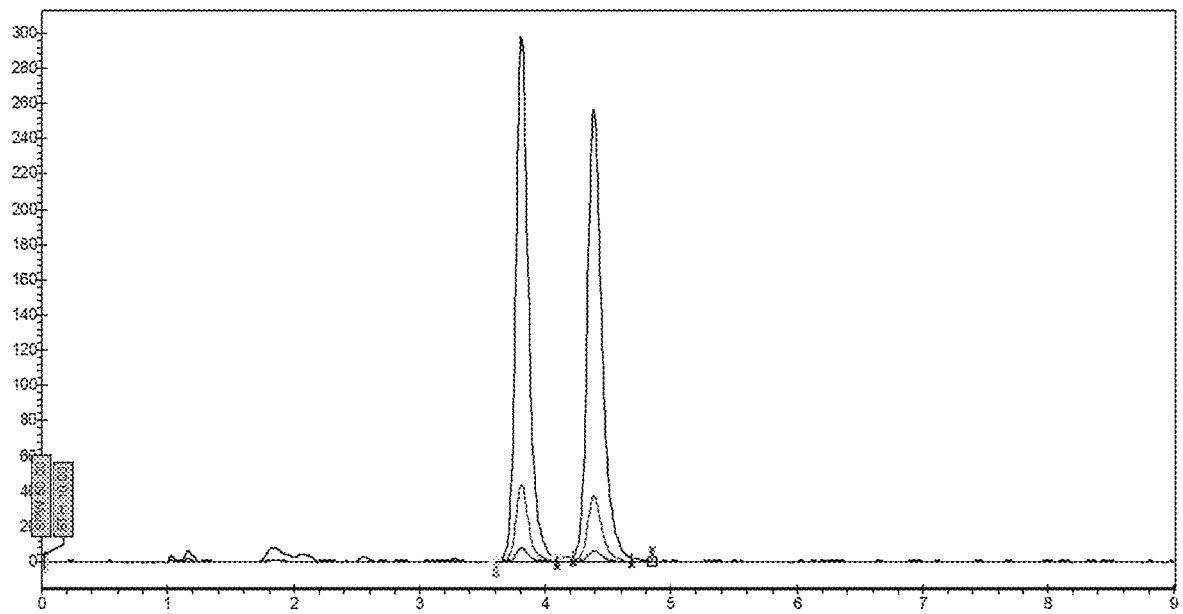
FIG. 4 illustrates the supercritical fluid chromatography (SFC) analysis of the racemate of Example 1-4 on chiral column.
Figure 5:
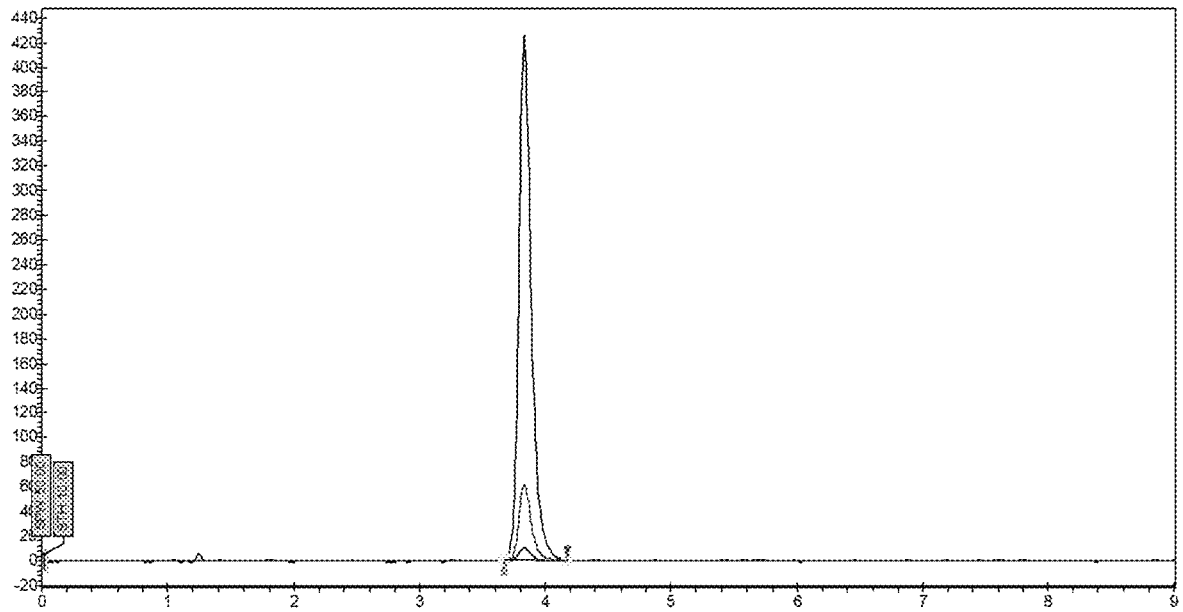
FIG. 5 illustrates the supercritical fluid chromatography (SFC) analysis of the enantiomer Example 1-4A on chiral column.
Figure 6:
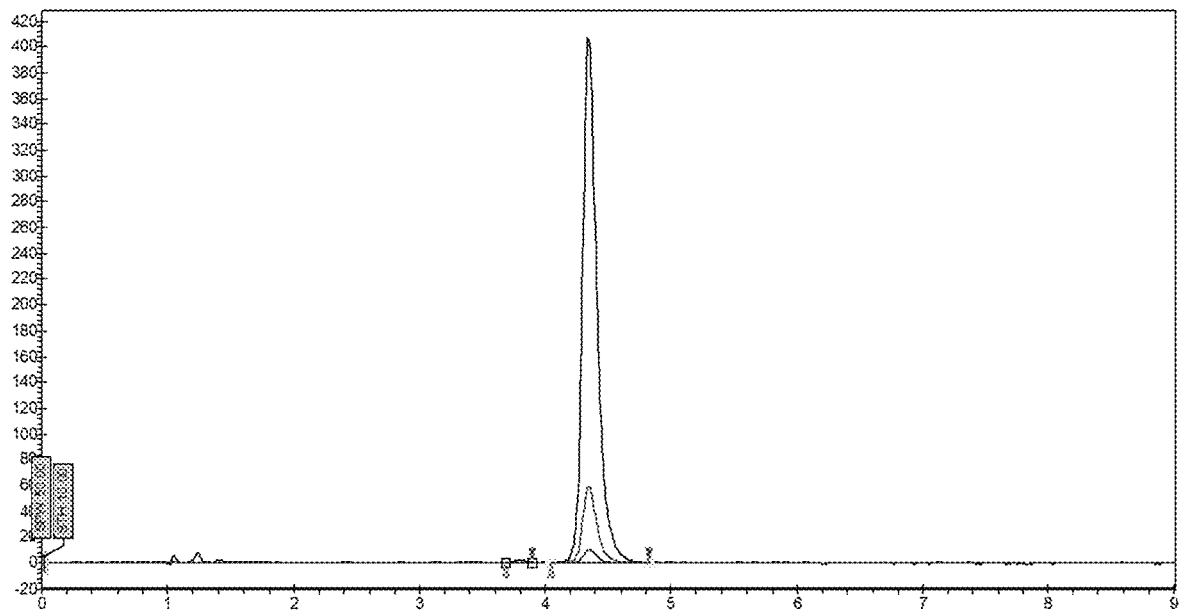
FIG. 6 illustrates the supercritical fluid chromatography (SFC) analysis of the enantiomer Example 1-4B on chiral column.

Example 1-4A is one of the enantiomers that were separated from the racemate Example 1-4 with chiral chromatographic separation by Lotus Separation LLC. The chiral separation of the racemate Example 1-4 resulted in two peaks. As shown in FIG. 4, a baseline separation between the two enantiomers of Example 1-4 was achieved. Both enantiomers were collected and reinjected and RT times confirmed good separation. Example 1-4A represents the first chromatographic peak with a shorter retention time (RT) at about 3.8 min as shown in FIGS. 4-6. Example 14A is the second chromatographic peak with a longer retention time (RT) at 4.4 min as shown in FIGS. 4-6. Example 1-4A has an enantiomeric excess (ee) of ≥99%0 and Example 1-41B an enantiomeric excess (ee) of ≥99%.

The dosing formulations of Example 1-4A, Example 1-41B, and Example 1-2 and difulfiram were prepared with PB S (pH 7.0) by thoroughly mixing via vortexing and sonication.

The dosing formulation was prepared with PBS (pH 7.0) by thoroughly mixing via vortexing and sonication.

Ethanol challenge study design and dosing groups of Example 14A, Example 14B, and Example 1-2 and difulfiram are as shown in Table 3.

General Procedures

Animals in Group 1 was administered vehicle (PBS) via tail vein injection, once daily for 3 days. Animals in Group 2 was administered vehicle (PBS) disulfiram at 3.57 mg/kg via oral gavage (PO) once daily for 3 days. Animals in Groups 3-11 were respectively administered Example 1-4A at 2, 6.5, and 12 mg/kg, Example 1-4B at 2, 6.5, and 12 mg/kg, or Example 1-2 at 2, 6.5, and 12 mg/kg via tail vein injection, once daily for 3 days.

Dosing volume (1 or 1.67 mL/kg) was calculated based on the individual body weight obtained prior to the first dose of test article.

Ethanol Challenge

Ethanol (200 PRF or 100% pure, non-denatured and no additives) was obtained from Fisher Scientific. Ethanol dosing solution (20% v/v in saline) was prepared by mixing one (1) part of ethanol and four (4) part of saline (0.9% NaCl) thoroughly to create a uniform solution prior to administration. Animals was administered 20% ethanol at 1 g/kg (IP) 8 hours following the third dose of test article. Thirty (30) minutes following ethanol challenge, animals were euthanized with $CO_2$. About 2 mL of whole blood was rapidly collected via vena cava for generation of plasma samples. Blood samples were placed into $K_2$ EDTA tubes and kept on wet ice prior to processing. Liver lysate generation, protein concentration determination, and ALDH2 activity assay were performed by Confluence Discovery Technologies (CDT). Protein concentrations were determined using the Pierce BCA Protein Assay Kit. ALDH2 Activity Assay using the Abcam assay kit #ab115348.

Results and Discussion

Figure 7:
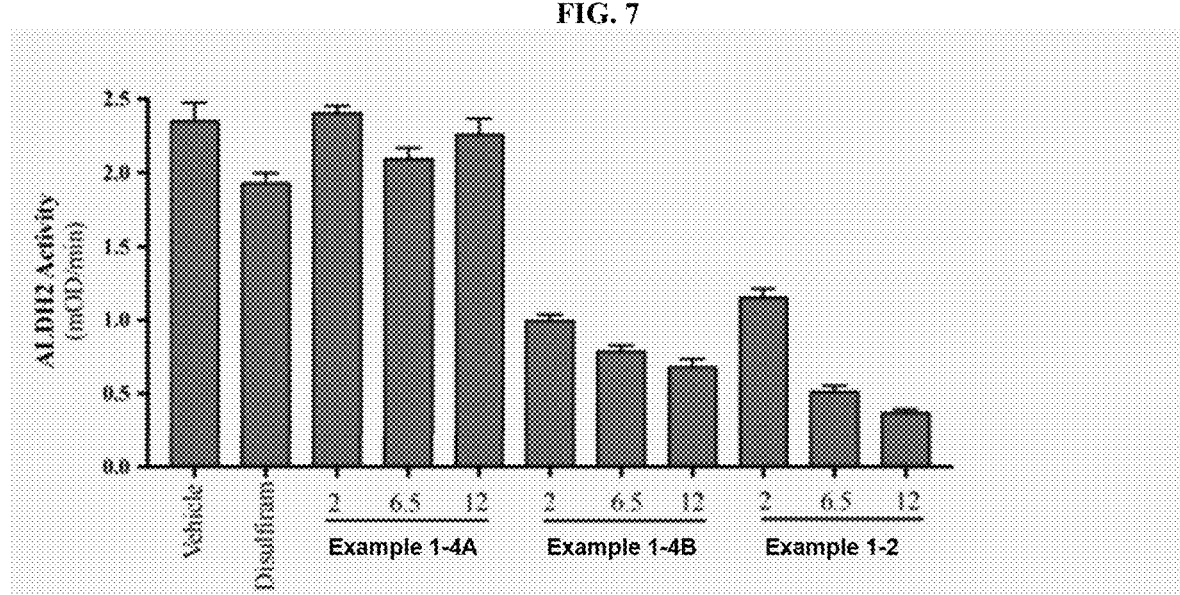
FIG. 7 illustrates the effects of Example 1-2, Example 1-4A, Example 1-4B, and disulfiram on liver ALDH2 activities of the rats following ethanol challenge based on treatment dosage levels.

As shown in FIG. 7, Example 1-2 and Example 1-4B both showed ALDH2 inhibitions at dosages of 2 mg/kg, 6.5 mg/kg, and 12 mg/kg respectively after 5 days. A dose-activity response was observed for both Example 1-2 and Example 1-4B. The ALDH2 inhibitions of Example 1-2 and Example 1-4B at dosages of 2 mg/kg, 6.5 mg/kg, and 12 mg/kg respectively are statistically significant. Surprisingly and unexpectedly, both Example 1-2 and Example 1-4B showed greater inhibition after three days at the dosage of 2 mg/kg/day than Disulfiram at the dosage of 3.57 mg/kg/day. The observation that both Example 1-2 and Example 1-4B achieved significant inhibition of ALDH2 activity after only 3-day administration is unexpected and surprising, which indicates a fast activity onset.

Example 4: Plasma Acetaldehyde Determination Assay

Compounds as described herein are tested on Plasma Acetaldehyde Determination Assay in rats. The Rats main-

TABLE 3

| Group # | Test Article | Dose (mg/kg) | Dose Concentration (mg/mL) | Dose Volume (mL/kg) | Route | Frequency & Duration | Sample Size |
|---|---|---|---|---|---|---|---|
| 1 | Vehicle | N/A | N/A | 1 | IV | QD, 3 Days | 8 |
| 2 | Disulfiram | 3.57 | 2.14 | 1.67 | PO | | 8 |
| 3 | Example 1-4A | 2 | 2 | 1 | IV | | 8 |
| 4 | | 6.5 | 6.5 | 1 | IV | | 8 |
| 5 | | 12 | 12 | 1 | IV | | 8 |
| 6 | Example 1-4B | 2 | 2 | 1 | IV | | 8 |
| 7 | | 6.5 | 6.5 | 1 | IV | | 8 |
| 8 | | 12 | 12 | 1 | IV | | 8 |
| 9 | Example 1-2 | 2 | 2 | 1 | IV | | 8 |
| 10 | | 6.5 | 6.5 | 1 | IV | | 8 |
| 11 | | 12 | 12 | 1 | IV | | 8 |

QD: once per day; PO: oral; IV: intravenous tained as described in Example 2, fasted for 18 hours, are given 2-10 mg/kg of Example 1-2 intravenously, dissolved in polyethylene glycol 200 and then challenged eight hours later with a dose of ethanol (1 g/kg; 20% v/v) also administered intravenously. The rats are anesthetized with phenobarbital 30 minutes after alcohol administration and blood are taken by aortic puncture, being drawn into heparinized syringe. Plasma acetaldehyde are determined by the method of C. O. P. Eriksson et al., Anal. Biochem., 80, 116 (1977)), which is hereby incorporated by reference in its entirety. Plasma concentrations are determined based on a standard curve obtained with known concentrations of acetaldehyde. Control rats were treated with 1 ml/kg of polyethylene glycol 200. Higher levels of plasma acetaldehyde indicate that the compounds inhibit ALDH2.

Animals administered compounds as described herein, such as

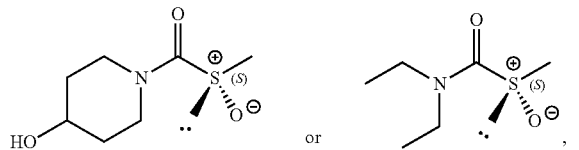

or a pharmaceutically acceptable salt of solvate thereof, have a higher level of the plasma acetaldehyde as compared to the controls, which indicates that the compounds are more effective in inhibiting ALDH2.

Example 5: Alcohol Preference Models

Compounds as described herein are tested for efficacy of suppressing the appetite for alcohol of rats on Alcohol Preference Models. In the alcohol-preferring rat model, the selectively-bred P line of rats are used for the study. The rats were offered a free choice between water and alcohol solutions of various concentrations. The rats with and without the administration of a compound as described herein are tested for the preference of the alcohol solution. The rats administered compounds as described herein, such as

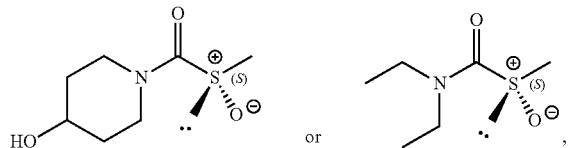

or a pharmaceutically acceptable salt of solvate thereof, show a reduced preference for the alcohol solution.

Example 6: Reinstatement Model

Compounds as described herein are tested for efficacy of suppressing craving and relapse behaviors for alcohol of rats on Reinstatement Model. In the reinstatement mode, rats are trained over several months to press a lever in order to receive alcohol. After stable lever pressing is obtained, the rats are tested in extinction, receiving water instead of alcohol following lever pressing. After 8 to 10 extinction sessions, administration of a small quantity of alcohol reinstates previously extinguished alcohol-seeking behavior. The rats in extinction with and without the administration of a compound as described herein before the administration of a small quantity of alcohol and their alcohol-seeking behaviors are measured. The animals administered compounds as provided herein, such as

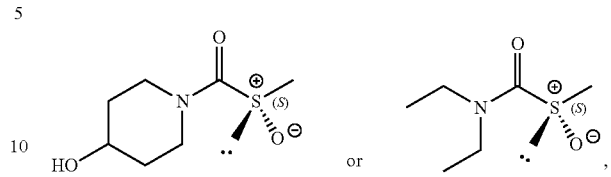

or a pharmaceutically acceptable salt of solvate thereof, are found not to have the behavior reinstated.

Example 7: Long-Term Alcohol Self-Administration with Repeated Alcohol Deprivation Phases Model Compounds as described herein are tested for efficacy of changing rat's alcohol intake patterns on Long-Term Alcohol Self Administration with Repeated Alcohol Deprivation Phases Model. In this model, male Wistar rats have free access to food, water, and three alcohol solutions of 5, 10, and 20 percent (volume/volume) in their cage. After two months of continuous alcohol access, the rats are deprived of alcohol for several days before again being offered all alcohol solutions. This procedure is repeated monthly for the following year. The renewed availability of the alcohol solutions following a deprivation phase leads to a pronounced but temporary rise in alcohol intake and preference, the alcohol deprivation effect (ADE). Rats with and without administration of a compound as described herein are tested for the alcohol intake and preference over several weeks.

Animals administered compounds as described herein, such as

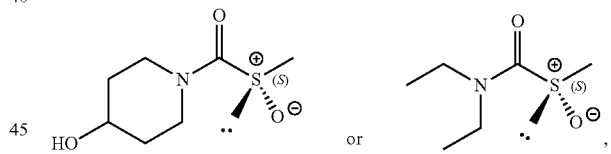

or a pharmaceutically acceptable salt of solvate thereof, are found to have a reduced preference for alcohol.

Example 8: Point-of-no-Return Model

Compounds as described herein are tested for deterring the development of "loss of control" of drinking alcohol on rats in Point-of-no-Return Model. In this model, rats are offered free access to water and to alcohol solutions with concentrations of 5, 10, and 20 percent. The rats had access to alcohol for 9 months, followed by a long-term abstinence period of 9 months. After approximately 6 months of continuous access to alcohol, the rats gradually exhibit increasing alcohol consumption over the next few months. After the abstinence period, the rats again had access to the alcohol solutions. Rats with and without administration of a compound as described herein are tested for the alcohol intake and preference over several weeks. Animals administered compounds as described herein, such as

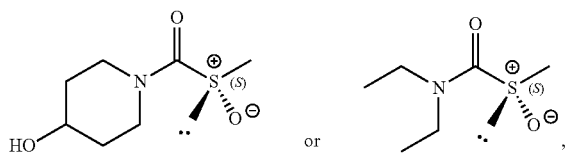

or a pharmaceutically acceptable salt of solvate thereof, are found to have a reduced preference for alcohol and reduce alcohol intake.

The present examples and embodiments provided for herein demonstrate the surprising and unexpected results that the compounds can be used to treat alcohol use disorder as well as other conditions associated with significant and unwanted alcohol consumption or alcohol use disorder.

This specification contains numerous citations to patents, patent applications, and publications. Each is hereby incorporated by reference for all purposes, including as context dictates.

What is claimed is:

1. A pharmaceutical composition comprising a compound having a formula of

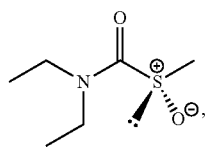

or a pharmaceutically acceptable salt solvate thereof, in an enantiomeric excess of at least 95%.

2. The pharmaceutical composition of claim 1, wherein the pharmaceutical composition comprises the compound having the formula of

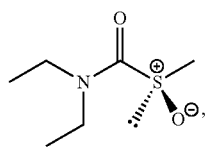

or a pharmaceutically acceptable salt solvate thereof, in an enantiomeric excess of at least 96%.

3. The pharmaceutical composition of claim 1, wherein the pharmaceutical composition comprises the compound having the formula of

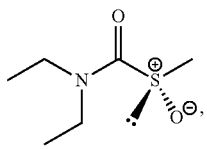

or a pharmaceutically acceptable salt solvate thereof, in an enantiomeric excess of at least 97%.

4. The pharmaceutical composition of claim 1, wherein the pharmaceutical composition comprises the compound having the formula of

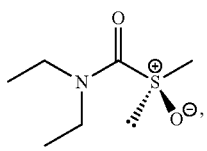

or a pharmaceutically acceptable salt solvate thereof, in an enantiomeric excess of at least 98%.

5. The pharmaceutical composition of claim 1, wherein the pharmaceutical composition comprises the compound having the formula of

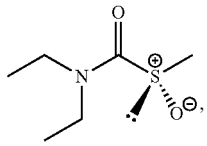

or a pharmaceutically acceptable salt solvate thereof, in an enantiomeric excess of at least 99%.

6. A method of treating alcohol use disorder in a subject, the method comprising administering to the subject the pharmaceutical composition of claim 1.

7. A method of treating alcohol use disorder in a subject, the method comprising administering to the subject the pharmaceutical composition of claim 2.

8. A method of treating alcohol use disorder in a subject, the method comprising administering to the subject the pharmaceutical composition of claim 3.

9. A method of treating alcohol use disorder in a subject, the method comprising administering to the subject the pharmaceutical composition of claim 4.

10. A method of treating alcohol use disorder in a subject, the method comprising administering to the subject the pharmaceutical composition of claim 5.

* * * * *